(12) United States Patent
Boss et al.

(10) Patent No.: US 9,534,007 B2
(45) Date of Patent: Jan. 3, 2017

(54) METHODS AND COMPOSITIONS FOR TREATMENT OF CYANIDE AND HYDROGEN SULFIDE TOXICITY

(71) Applicants: The Regents of the University of California, Oakland, CA (US); The United States of America as represented by The Secretary of the Air Force, Washington, DC (US)

(72) Inventors: Gerry Boss, La Jolla, CA (US); Adriano Chan, La Jolla, CA (US); Matthew Brenner, Irvine, CA (US); Sari Brenner-Mahon, Irvine, CA (US); Vikhyat S. Bebarta, San Antonio, TX (US); Jingjing Jiang, La Jolla, CA (US); Karen Christman, La Jolla, CA (US); Jean Wang Wassenaar, La Jolla, CA (US)

(73) Assignees: THE REGENTS OF THE UNIVERSITY OF CALIFORNIA, Oakland, CA (US); THE UNITED STATES OF AMERICA as represented by THE SECRETARY OF THE AIR FORCE, Washington, DC (US)

( * ) Notice: Subject to any disclaimer, the term of this patent is extended or adjusted under 35 U.S.C. 154(b) by 0 days.

(21) Appl. No.: 14/654,438

(22) PCT Filed: Dec. 23, 2013

(86) PCT No.: PCT/US2013/077632
§ 371 (c)(1),
(2) Date: Jun. 19, 2015

(87) PCT Pub. No.: WO2014/100834
PCT Pub. Date: Jun. 26, 2014

(65) Prior Publication Data
US 2015/0353590 A1      Dec. 10, 2015

Related U.S. Application Data

(60) Provisional application No. 61/740,740, filed on Dec. 21, 2012, provisional application No. 61/883,930, filed on Sep. 27, 2013.

(51) Int. Cl.
*C07F 15/06* (2006.01)
*G01N 33/52* (2006.01)

(52) U.S. Cl.
CPC ............ *C07F 15/065* (2013.01); *G01N 33/52* (2013.01)

(58) Field of Classification Search
CPC .................................................. A61K 31/555
See application file for complete search history.

(56) References Cited

U.S. PATENT DOCUMENTS

2010/0152153 A1\* 6/2010 Boss .................... A61K 31/555
                                                                    514/184

FOREIGN PATENT DOCUMENTS

EA        200700876 A1    10/2007
WO     2010/124122 A1    10/2010

OTHER PUBLICATIONS

International Application No. PCT/US2013/077632, International Search Report and Written Opinion, mailed Jun. 5, 2014.
Fujita, Yuji et al., "A Fatal Case of Acute Hydrogen Sulfide Poisoning Caused by Hydrogen Sulfide: Hydroxocobalamin Therapy for Acute Hydrogen Sulfide Poisoning", Journal of Analytical Toxicology, 2011, vol. 35, pp. 119-123.
Chan, Adriano et al., "Cobinamide is superior to other treatments in a mouse model of cyanide poisoning", Clin. Toxicol. (Phila), 2010, 48(7), pp. 709-717.

\* cited by examiner

*Primary Examiner* — Paul V Ward
(74) *Attorney, Agent, or Firm* — Kilpatrick Townsend & Stockton LLP

(57) ABSTRACT

A composition and method for treating excess cyanide and hydrogen sulfide comprising administering a cobinamide. Further a method for determining extent of binding by an agent to an extracellular matrix.

19 Claims, 34 Drawing Sheets

METHODS AND COMPOSITIONS FOR TREATMENT OF CYANIDE AND HYDROGEN SULFIDE TOXICITY

CROSS REFERENCE TO RELATED APPLICATIONS

This application claims the benefit of U.S. Provisional Applications 61/740,740 filed Dec. 21, 2012 and 61/883,930 filed Sep. 27, 2013, both of which are hereby incorporated by reference in their entirety for all purposes.

STATEMENT REGARDING FEDERALLY SPONSORED RESEARCH OR DEVELOPMENT

This invention was made with government support under Grant Nos: R21NS072105 and U01NS058030 awarded by the National Institutes of Health. The government has certain rights in the invention.

FIELD

This application generally relates to cobinamide and biologically active derivatives and analogs of cobinamide that modulate excess cyanide and hydrogen sulfide levels in patients.

BACKGROUND

Cyanide is a highly toxic agent which inhibits mitochondrial cytochrome c oxidase, thereby depleting cellular ATP. It contributes to smoke inhalation deaths in fires, and could be used as a weapon of mass destruction. Cyanide is generated in household fires due to the high amount of plastic material that is usually present.

Hydrogen sulfide is an extremely toxic gas for which no treatment is available. Workers in a variety of industries are exposed to hydrogen sulfide—most notably the petroleum industry, where one-third of workers are exposed to sufficient gas to have symptoms, with 8% having experienced loss of consciousness. Moreover, inhalation of hydrogen sulfide gas is a common mode of suicide and the gas could be used by terrorists as a weapon of mass destruction.

Cobinamide has been disclosed as a treatment for cyanide toxicity. In its aqueous state, cobinamide takes the form of aquohydroxocobinamide at neutral pH and is effective when administered intravenously. However, intravenous administration of antidotes is not preferred in mass casualty situations because of the additional skill required to inject intravenously and the time it takes to do such an injection. In a disaster situation, such as a terrorist attack, every second counts and thus a form of cobinamide that can be administered more simply than intravenously is needed.

SUMMARY

Disclosed herein is a compound having formula I:

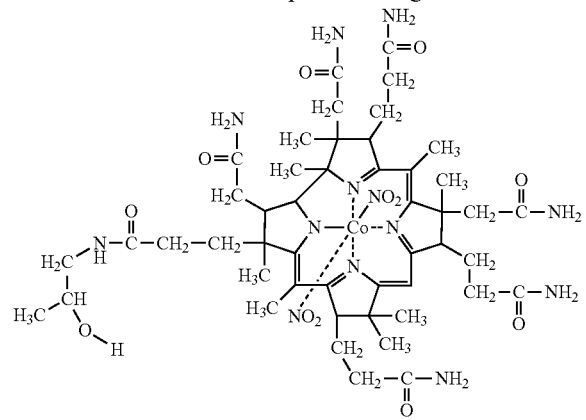

or pharmaceutically acceptable salts thereof. Also provided is a pharmaceutical composition comprising the disclosed compound. In some embodiments, the pharmaceutical composition further comprises nitrite ion. In some embodiments, the molar ratio of the compound and nitrite ion is between 1:1 and 1:2. Also provided is a method for treating a disease state in a subject caused or exacerbated by the presence of excess cyanide in the subject comprising administering a therapeutically effective amount of the compound of formula I. In some embodiments the subject is a human. In some embodiments the cobinamide is administered intravenously or intramuscularly. In some embodiments, the cobinamide is administered at a dose of between 2 mg/kg and 25 mg/kg, between 2 mg/kg and 17 mg/kg, between 2 mg/kg and 15 mg/kg or between 15 mg/kg and 17 mg/kg.

Also provided is a method for treating a disease state in a subject caused or exacerbated by the presence of excess hydrogen sulfide ($H_2S$) in the subject comprising administering a pharmaceutically effective amount of cobinamide to the subject. Cobinamide includes compounds similar to formula I with different ligands attached at the positions occupied by $NO_2$. In some embodiments, those ligands are sulfite, water or hydroxyl. In some embodiments, the cobinamide is aquohydroxocobinamide, dinitrocobinamide or sulfitocobinamide. In some embodiments the subject is a human. In some embodiments the cobinamide is administered intravenously or intramuscularly. In some embodiments, the cobinamide is administered at a dose of between 2 mg/kg and 25 mg/kg, between 2 mg/kg and 17 mg/kg, between 2 mg/kg and 15 mg/kg or between 15 mg/kg and 17 mg/kg.

Also provided is a method of determining an extent of binding of an agent to extracellular matrix, the method comprising: providing a sample of mammalian extracellular matrix; contacting the sample with a solution comprising a known concentration of the agent; allowing binding to occur; and determining a second concentration of the agent remaining in the solution. In some embodiments the extracellular matrix is from muscle tissue. In some embodiments the extracellular matrix comprises decellularized skeletal muscle extracellular matrix. In some embodiments the agent is a cobinamide. In some embodiments, spectrophotometric methods are used to determine the concentration of the agent remaining.

DETAILED DESCRIPTION

Figure 1:
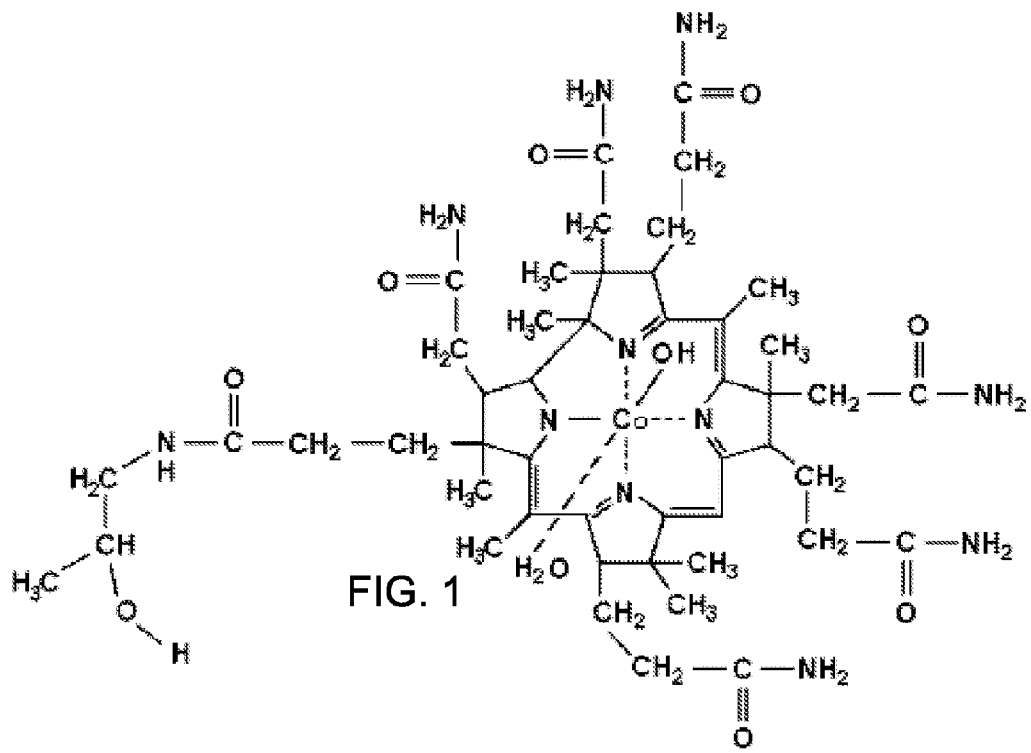
FIG. 1 illustrates cobinamide in the form aquohydroxocobinamide.

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a cell" includes one or a plurality of such cells, and so forth. The term "or" refers to a single element of stated alternative elements or a combination of two or more elements, unless the context clearly indicates otherwise.

"Patient" refers to mammals such as human patients and non-human primates, as well as experimental animals such as rabbits, rats, and mice, and other animals Animals include all vertebrates, e.g., mammals and non-mammals, such as sheep, dogs, cows, chickens, amphibians, and reptiles.

"Treating" refers to any indicia of success in the treatment or amelioration or prevention of the disease, condition, or disorder, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with a disease, condition or disorder as described herein. The term "therapeutic effect" refers to the reduction, elimination, or prevention of the disease, symptoms of the disease, or side effects of the disease in the subject. "Treating" or "treatment" using the methods of the present invention includes preventing the onset of symptoms in a subject that can be at increased risk of a disease or disorder associated with a disease, condition or disorder as described herein, but does not yet experience or exhibit symptoms, inhibiting the symptoms of a disease or disorder (slowing or arresting its development), providing relief from the symptoms or side-effects of a disease (including palliative treatment), and relieving the symptoms of a disease (causing regression). Treatment can be prophylactic (to prevent or delay the onset of the disease, or to prevent the manifestation of clinical or subclinical symptoms thereof) or therapeutic suppression or alleviation of symptoms after the manifestation of the disease or condition. The term "treatment," as used herein, includes preventative (e.g., prophylactic), curative or palliative treatment.

The term "administering," as used herein, means either directly administering a compound or composition of the present invention, or administering a prodrug, derivative or analog which will form an equivalent amount of the active compound or substance within the body. The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention can be present in more than one stereoisomeric form, and the naming of such compounds is intended to include all single stereoisomers and all mixtures (whether racemic or otherwise) of such stereoisomers.

"Pharmaceutically acceptable carrier (or medium)", which can be used interchangeably with "biologically compatible carrier or medium", refers to reagents, cells, compounds, materials, compositions, and/or dosage forms which are, within the scope of sound medical judgment, suitable for use in contact with the tissues of human beings and animals without excessive toxicity, irritation, allergic response, or other complication commensurate with a reasonable benefit/risk ratio. As described in greater detail herein, pharmaceutically acceptable carriers suitable for use in the present invention include liquids, semi-solid (e.g., gels) and solid materials (e.g., cell scaffolds). As used herein, the term biodegradable describes the ability of a material to be broken down (e.g., degraded, eroded, dissolved) in vivo. The term includes degradation in vivo with or without elimination (e.g., by resorption) from the body. The semi-solid and solid materials can be designed to resist degradation within the body (non-biodegradable) or they can be designed to degrade within the body (biodegradable, bioerodable). A biodegradable material can further be bioresorbable or bioabsorbable, i.e., it can be dissolved and absorbed into bodily fluids (water-soluble implants are one example), or degraded and ultimately eliminated from the body, either by conversion into other materials or breakdown and elimination through natural pathways.

A "therapeutically effective amount", "effective amount" and gramatical variations thereof, as they refer to pharmaceutical compositions of the invention, are used interchangeably and represent the amount that, when administered to a subject for treating a disease or condition, is sufficient to effect treatment for that disease or condition. "Therapeutically effective amount," as used herein, refers to an amount effective, at dosages, and for periods of time necessary, to achieve the desired result. In particular, "therapeutically effective amount" refers to the amount of compound or composition of compounds that would treat a disease state in a subject caused or exacerbated by the present of excess nitric oxide or cyanide toxicity in a subject.

It will be appreciated that the effective amount of components of the present invention will vary from patient to patient not only with the particular compound, component or composition selected, the route of administration, and the ability of the components (alone or in combination with one or more combination drugs) to elicit a desired response in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage ultimately being at the discretion of the attendant physician. Dosage regimens can be adjusted to provide the improved therapeutic response. A therapeutically effective amount is also one in which any toxic or detrimental effects of the components are outweighed by the therapeutically beneficial effects.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

All publications disclosed herein are incorporated by reference in their entirety for all purposes.

FIG. 1 illustrates the structure of cobinamide in the form aquohydroxocobinamide. This is the form of cobinamide in aqueous solution at neutral pH. At pH>11, cobinamide exists as dihydroxocobinamide. The water molecule attached to the cobalt in FIG. 1 is replaced by an OH. At acidic pH, cobinamide exists as diaquocobinamide in which the hydroxyl group attached to cobalt in FIG. 1 is replaced by a second water molecule. Cobinamide can be produced by base hydrolysis of hydroxocobalamin at pH 9.5 using cerium hydroxide. This results in cobinamide with water and hydroxyl ligands. In this application, the term "cobinamide" refers to the compound in FIG. 1 without specifying the particular ligands attached to cobalt that are water and hydroxyl in FIG. 1. Thus cobinamide encompasses aquohydroxocobinamide, diaquocobinamide, dihydroxocobinamide, dinitrocobinamide, hydroxonitrocobinamide, etc. The term "cobinamide derivative" refers to cobinamide having a ligand other than hydroxyl or water. Dinitrocobinamde and hydroxonitrocobinamide are examples of cobinamide derivatives.

Figure 2:
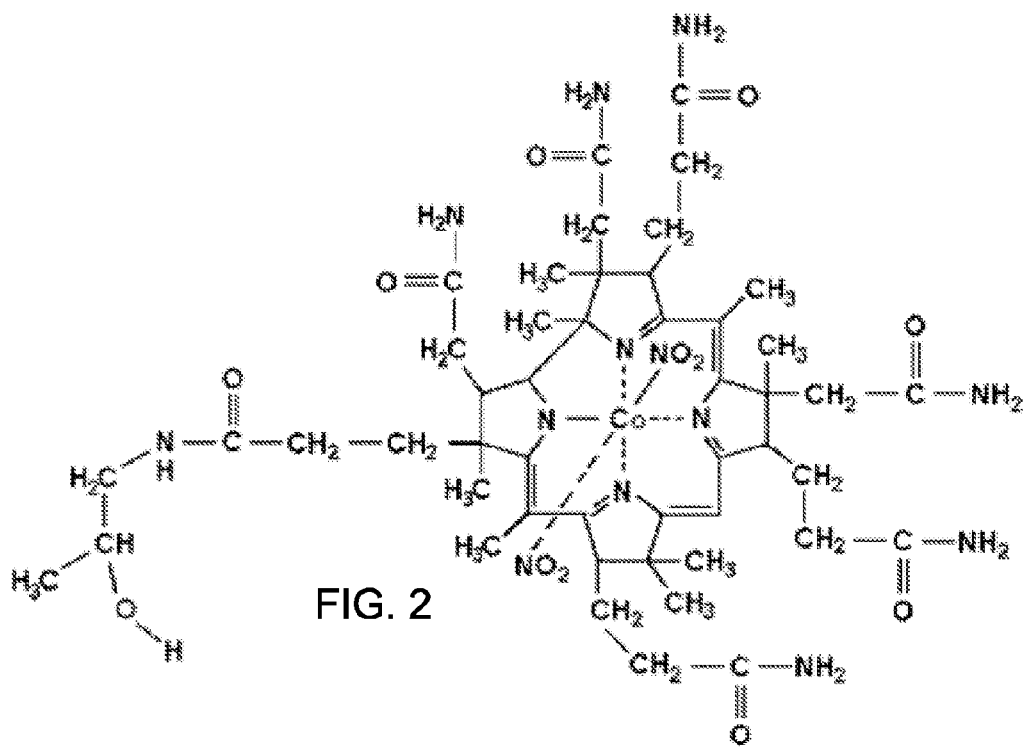
FIG. 2 illustrates cobinamide in the form dinitrocobinamide.

Additional ligands can also bind cobinamide. Disclosed herein is cobinamide having nitrite bound to the cobalt as shown in FIG. 2. FIG. 2 illustrates dinitrocobinamide. When there are fewer than two, but more than one, molar equivalent nitrite ion in the solution with cobinamide, some cobinamide will be in the form of aquonitrocobinamide—namely one water bound to cobalt and one nitrite bound to cobalt. Dinitrocobinamide is formed by the addition of a nitrite salt, for example sodium nitrite ($NaNO_2$) to the aqueous solution of cobinamide. As cobinamide has two binding sites for nitrite, converting aquohydroxocobinamide to dinitrocobinamide requires a molar ratio of at least 2 $NO_2^-$ to 1 cobinamide.

Cobinamide can be produced either by acid or base hydrolysis. Base hydrolysis of hydroxocobalamin to produce cobinamide is disclosed by Renz. (*Methods Enzymol.* 1971, 18c, 82-86) Acid hydrolysis of cobalamin to obtain cobinamide is disclosed in Broderick et al (*J Biol. Chem.*, 2005, 280, 8678-8685). In aqueous solution, the resulting cobinamide has water and hydroxyl ligands.

As described below in Example 1, dinitrocobinamide, an agent being developed as a cyanide antidote, was as effective as hydroxocobalamin, an established cyanide antidote, in rescuing pigs from a lethal injection of cyanide. The time to spontaneous breathing after cyanide induced apnea was similar between the two treated groups. In addition, both groups were similar in mortality, lacticemia, acidosis, and clearance of cyanide. Mean arterial pressure was significantly higher in the hydroxocobalamin group but by the conclusion of the study, this difference had abated.

For intramuscular injection, cobinamide bound to nitrite is absorbed more readily than hydroxoaquocobinamide. This disclosure includes compositions for intramuscular administration of cobinamide for treatment of cyanide and hydrogen sulfide toxicity. It has been found that a composition comprising dinitrocobinamide with excess nitrite in solution is absorbed more readily after intramuscular injection. Thus provided herein is a composition comprising dinitrocobinamide with a source of nitrite, such as sodium nitrite, in a molar ratio of 1 dinitrocobinamide to up to 2 nitrite. In practice, such a composition is obtained by combining nitrite and aquohydroxocobinamide in a molar ratio of 4 nitrite to 1 aquohydroxocobinamide.

Although dinitrocobinamide and hydroxocobalamin were both efficacious, dinitrocobinamide was considerably more potent, because five times more hydroxocobalamin than cobinamide (on a milligram per kilogram basis) was required to rescue swine. Similar results in mice and rabbits where cobinamide is three to 10 times more potent than hydroxocobalamin as a cyanide antidote, depending on the cyanide exposure model. (See Brenner, M., et al. *Ann Emerg Med* 2010; 55:352-63; Chan, A., et al. *Clin Toxicol* (Phila) 2010; 48:709-17)

EXAMPLES

Example 1

Dinitrocobinamide Compared to Hydroxocobalamin in Treating Cyanide Exposure

Yorkshire swine (*Sus scrofa*) (N=33, weighing 45-55 kg, female) were premedicated with intramuscular ketamine 10 mg/kg. General anesthesia was induced with isoflurane via nose cone. Following endotracheal intubation, the animals were mechanically ventilated with a volume-limited, time-cycled ventilator (Drager-Siemens, Fabius G S anesthesia machine, New York City, N.Y.), and maintained with inhaled isoflurane (1-3%) and oxygen ($FiO_2$ of 0.4-0.45). The tidal volume was initially 8-10 ml/kg and respiratory rate was 12 breaths per minute. The minute ventilation was adjusted to maintain an end tidal $CO_2$ of 38-42 mm Hg as measured by inline capnography. Lead II of the surface electrocardiogram was monitored continuously. Animal body temperature was maintained at 37.5-39.0° C. Baseline biochemical variables (arterial blood gas, hemoglobin, and electrolytes) were measured.

Invasive hemodynamic variables were measured with an eight-French Swan-Ganz CCOmbo pulmonary artery catheter (Model 746HF8) and the Edwards Vigilance II monitor (Edwards Lifesciences, Irvine, Calif.). Measurements included continuous cardiac output, systemic vascular resistance, mixed venous oxygen saturation, central venous pressure, pulmonary artery pressure, and core temperature. Catheter ports were flushed with saline and the catheter was placed via cutdown in the right external jugular. Aortic pressure was measured continuously through the femoral artery. An 8.5 French introducer (Arrow, Reading, Pa.) was placed in the carotid artery for laboratory sampling and another was placed in the femoral vein for medication administration. The animals received a warmed saline intravenous bolus (15 ml/kg) during procedure setup. Heparin (100 units per kilogram) was administered intravenously after catheters were inserted. The Fabius GS anesthesia data collection software embedded in the ventilator's computer was used for data acquisition at one-minute intervals.

Baseline biochemical measurements included oxygen saturation, $PaCO_2$, $PaO_2$, and pH (ABL 800 Flex blood gas analyzer, Radiometer America, Westlake, Ohio), and hemoglobin (OSM3 Hemoximeter, Radiometer, Westlake Ohio), and electrolytes (Piccolo Chemistry Analyzer, Abaxis, Union City, Calif.). Ventilation and oxygenation variables were also collected and included tidal volume, respiratory rate, minute volume, and pulse oximetry.

After a 10 min acclimation period, the isoflurane was reduced to 1-1.5%, the $FIO_2$ was adjusted to room air (0.21), and the ventilator was turned off. Thus, the animals breathed spontaneously for the remainder of the experiment. The animals were then randomized to one of three arms: dinitrocobinamide (12.5 mg/kg), hydroxocobalamin (65 mg/kg), or saline (10 ml of 0.9% normal saline). A 4% potassium cyanide solution (potassium cyanide, Sigma Aldrich; normal saline) was infused continuously until apnea occurred. One minute post apnea (Time Zero), animals were administered the antidote or saline intravenously as a bolus injection. Animals received equal volumes of 90 ml during the infusion with 10 milliliters of saline given before and after each drug administration. The dose and infusion duration for dinitrocobinamide and hydroxocobalamin were based on previous published animal models and preliminary experiments. (Bebarta, V. S., et al. *Ann Emerg Med* 2012; 59:532-9; Brenner, M., et al. *Ann Emerg Med* 2010; 55:352-63; Borron, S. W., et al. *Clin Toxicol* (*Phila*) 2006; 44 Suppl 1:5-15; Bebarta, V. S., et al *Ann Emerg Med* 2010; 55:345-51; Broderick, K. E., et al. *Exp Biol Med* (Maywood) 2006; 231:641-9)

The animals were monitored for 60 minutes after treatment. Death was defined as a mean arterial pressure (MAP) less than 20 mm Hg for 5 min. Animals that died were observed for an additional 20 min or until the end of the experiment to evaluate for a possible delayed therapeutic effect. At death or the conclusion of the study, animals were euthanized with intravenous sodium pentobarbital 100 mg/kg.

Whole blood cyanide levels were measured spectrophotometrically at a referral laboratory (Michigan State University, Diagnostic Center for Population and Animal Health, Lansing, Mich.). (Hughes, C. et al. *Toxicology Mechanisms and Methods* 2003; 13:129-38) This method generates hydrogen cyanide gas, converts it to a cyanogen chloride, and measures a barbituric acid complex. (Id.; Bebarta, V. S., et al *Ann Emerg Med* 2010; 55:345-51) Plasma hydroxocobalamin and cyanocobalamin concentrations were measured using liquid chromatography and tandem mass spectrometry (LC/MS/MS). (Schwertner, H. A., et al. *J Chromatogr B Analyt Technol Biomed Life Sci* 2012; 905:10-6). Inflammatory markers of Tumor necrosis factor (TNF) alpha, interleukin (IL) 1b, IL-6, IL-8, and IL-10 were measured with ELISA (R&D Systems, Minneapolis, Minn.).

The average time (min:sec) to spontaneous breathing after one minute of cyanide induced apnea was compared between the three groups with the Kruskal-Wallis Test. Animals that died before 60 min from hypotension were excluded from this analysis. Before beginning the study, we defined apnea>1 min as clinically significant.

Secondary outcome variables (cardiac output, heart rate, systemic vascular resistance, respiratory rate, mean arterial blood pressure, and mixed venous oxygenation) were modeled using a repeated measures analysis of variance (RMANOVA) with adjustment for treatment, time, and the interaction of treatment by time with an auto-regressive covariance structure assumed. Post hoc analysis was performed on all variables that showed a significant treatment by time interaction, for which treatment contrasts were measured at each post treatment time-point with a Bonferroni adjustment for multiple testing applied. Values for arterial blood pH, lactate, cyanide, bicarbonate, base excess, and potassium concentrations were compared between groups using RMANOVA for times zero—60 min Tumor necrosis factor alpha (TNF-a), interleukin (IL) 1B, IL-6, IL-8, and IL-10 were measured at baseline, time zero, 30 min after drug infusion, and 60 min after drug infusion.

Additional analysis was performed to assess the differences in time to death between groups using Kaplan Meier estimation methods of the survival distribution, and log-rank testing to compare survival between the treatment groups.

All statistical testing was two sided with a signficiant level of alpha—0.05 and completed using SAS version 9.3 (Cary, N.C., USA). All graphical presentations were made using R version 2.15.1.

Sample size calculations were based on our previous animal experiments of acute cyanide toxicity. A sample size of 10 animals per group was determined to be sufficient was based on obtaining a power of 80%, an alpha of 0.05, and a standard deviation of 0.17 in mean time to detect a 20% difference in time to spontaneous breathing Sample size calculation was performed using PASS 12 (NCSS, LLC. Kaysville, Utah, USA. www.ncss.com.)

At baseline and at apnea, the groups had similar vital signs and biochemical variables (Tables 1 and 2). At time zero, predefined as apnea of one minute, there were no significant differences among groups (Table 3). Reduction in mean arterial blood pressure from baseline was also similar among groups (29%, 38%, 36% decrease, p=0.35).

TABLE 1

Baseline characteristics of animals in each group before receiving cyanide infusion
(wherein [1]Kruskal-Wallis Test; Data are presented as Mean (SD)

|  | Hydroxocobalamin (65 mg/kg IV) (N = 10) | Dinitrocobinamide (12.5 mg/kg IV) (N = 10) | Control (saline) (N = 11) | P-value[1] |
|---|---|---|---|---|
| Weight, kg | 49.9 (3.9) | 52.7 (3.09) | 51 (2.86) | 0.21 |
| Heart Rate, beats/min | 76.7 (10.69) | 84.9 (14.72) | 85.55 (23.56) | 0.47 |
| Systolic Blood Pressure, mm Hg | 122.9 (12.42) | 120.7 (16.46) | 119.36 (16.75) | 0.87 |
| Mean Arterial Pressure, mm Hg | 99.2 (12.35) | 97.9 (13.86) | 96.09 (17) | 0.83 |
| Cardiac Output, L/min | 4.97 (0.98) | 6.03 (1.13) | 5.13 (1.28) | 0.07 |
| Systemic vascular resistance, dynes-sec/cm$^5$ | 1564.2 (464.9) | 1244.9 (221.32) | 1418.9 (303.27) | 0.15 |
| pH, mEq/L | 7.46 (0.02) | 7.47 (0.03) | 7.47 (0.02) | 0.68 |
| Bicarbonate, mEq/L | 27.81 (1.26) | 27.56 (2) | 28.43 (2.24) | 0.63 |
| Lactate, mmol/L | 1.06 (0.38) | 1.1 (0.46) | 0.89 (0.31) | 0.51 |

TABLE 2

Characteristics for each group at apnea of the cyanide-poisoned animals
(wherein [1]Kruskal-Wallis Test; Data are presented as Mean (SD))

| Characteristics at Apnea | Hydroxcobalamin (65 mg/kg IV) (N = 10) | Dinitrocobinamide (12.5 mg/kg IV) (N = 10) | Control (saline) (N = 11) | P-value[1] |
|---|---|---|---|---|
| Cyanide dose, mg/kg | 1.91 (0.7) | 1.85 (0.53) | 1.67 (0.53) | 0.64 |
| Time to Apnea, min:sec | 11:12 (04:04) | 10:54 (03:07) | 09:49 (03:05) | 0.59 |

TABLE 3

Characteristics for each group at Time Zero (1 minute of apnea) of the cyanide-poisoned animals
(wherein [1]Kruskal-Wallis Test; Data are presented as Mean (SD))

| Characteristics at one minute of apnea | Hydroxocobalamin (65 mg/kg IV) (N = 10) | Dinitrocobinamide (12.5 mg/kg IV) (N = 10) | Control (saline) (N = 11) | P-value[1] |
|---|---|---|---|---|
| MAP at Apnea, mm Hg | 70 (17) | 61 (20) | 58 (27) | 0.12 |
| Lactate, mmol/L | 3.42 (1.34) | 3.69 (0.85) | 3.1 (1.1) | 0.17 |
| Cyanide level, ug/mL | 1.83 (0.51) | 1.68 (0.36) | 1.76 (0.59) | 0.8 |
| pH | 7.38 (0.05) | 7.36 (0.05) | 7.38 (0.07) | 0.32 |

Figure 3:
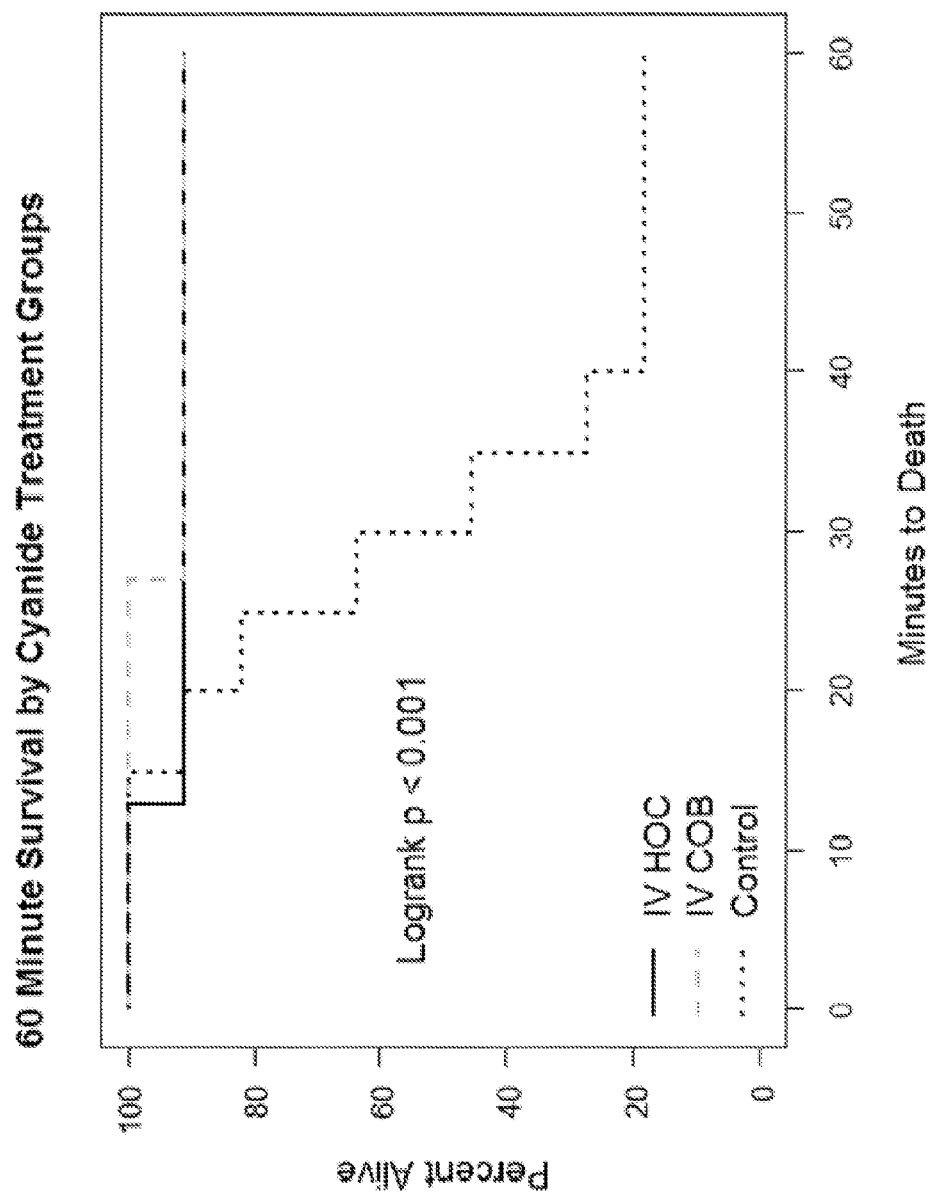
FIG. 3 illustrates survival analysis using a Kaplan Meier curse plot estimate comparing all the groups of cyanide-poisoned animals.

One animal in the hydroxocobalamin group, one animal in the dinitrocobinamide group, and nine animals in the control group died before completion of the experiment, i.e. between when receiving the antidote or saline at one min after onset of apnea and 60 min later (FIG. 3). Treatment groups showed a difference in survival (90% survival in treated animals, 10% in control) and time to death as compared to controls (p<0.001). The time to spontaneous breathing between the two treatment groups was similar: hydroxocobalamin group (1 min 48 seconds [SD 29 sec]), and dinitrocobinamide group (1 min 49 seconds [SD 31 sec]). This was significantly different from the control group (5 of 11 animals had spontaneous breathing, 4 min 5 seconds [SD 40 sec], p=0.005). Outcomes for the control group were reported and graphed until more than half of the animals died, which occurred at 30 min after time zero. As a control for nitrite administration, a group of five animals received sodium nitrite only, given at the same amount as present in the dinitrocobinamide. None of these animals survived, indicating that the effect of the dinitrocobinamide was from the cobinamide component and not the nitrite component.

Figure 4A:
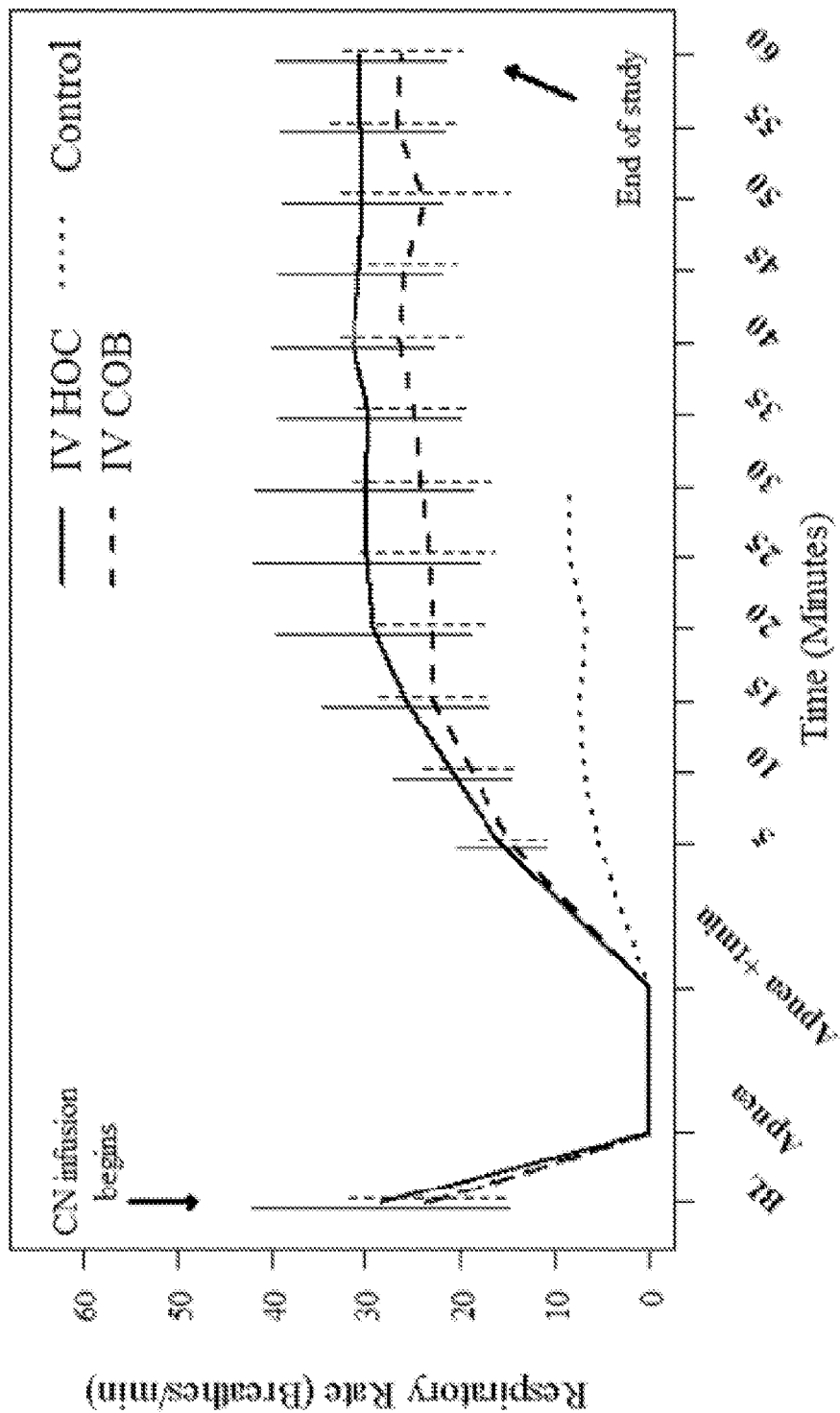
FIGS. 4A-E illustrate hemodynamic variables and vital signs (respiratory rate, mean arterial pressure [MAP], heart rate [HR], cardiac output, and mixed venous oxygenation [SVO2] saturation) in cyanide-poisoned animals over time.
Figure 4B:
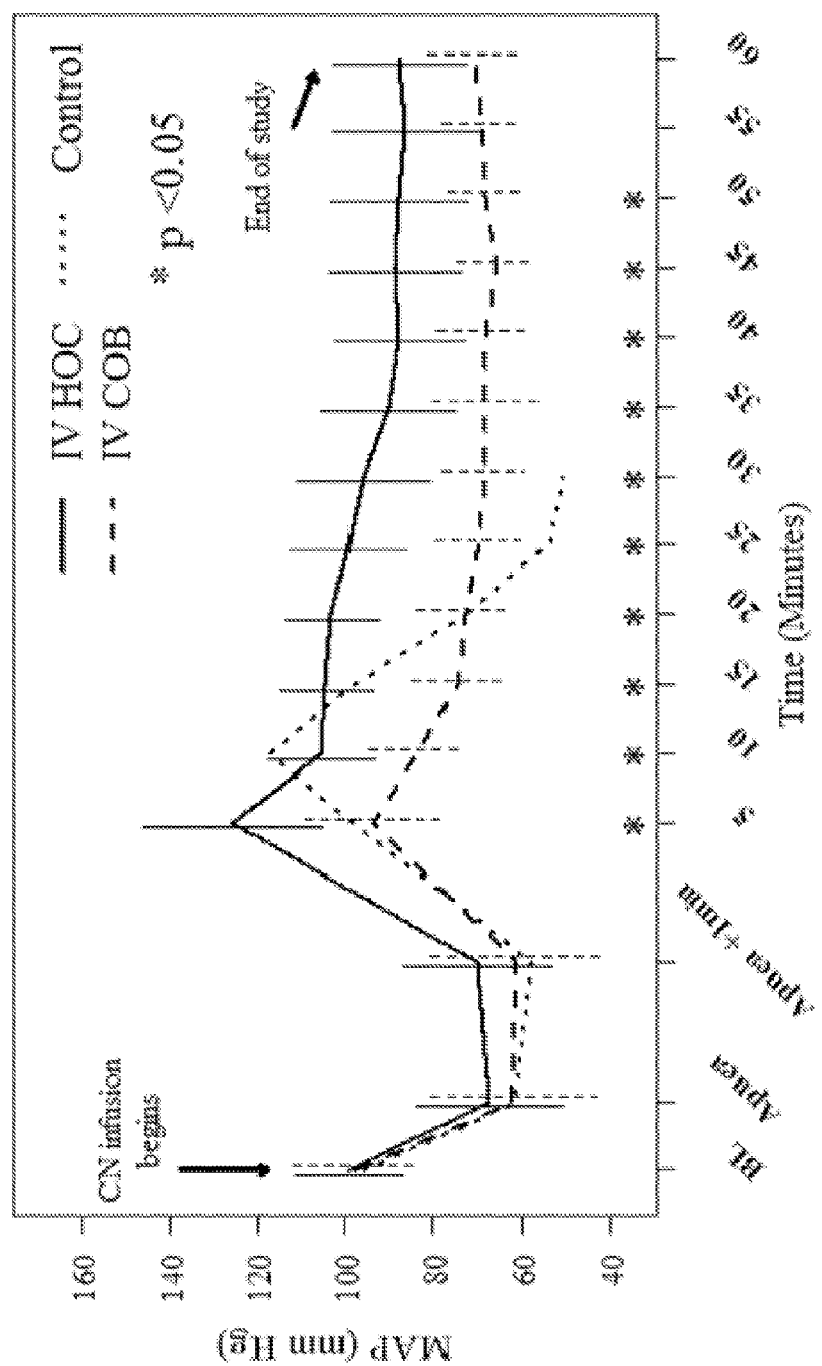
Figure 4C:
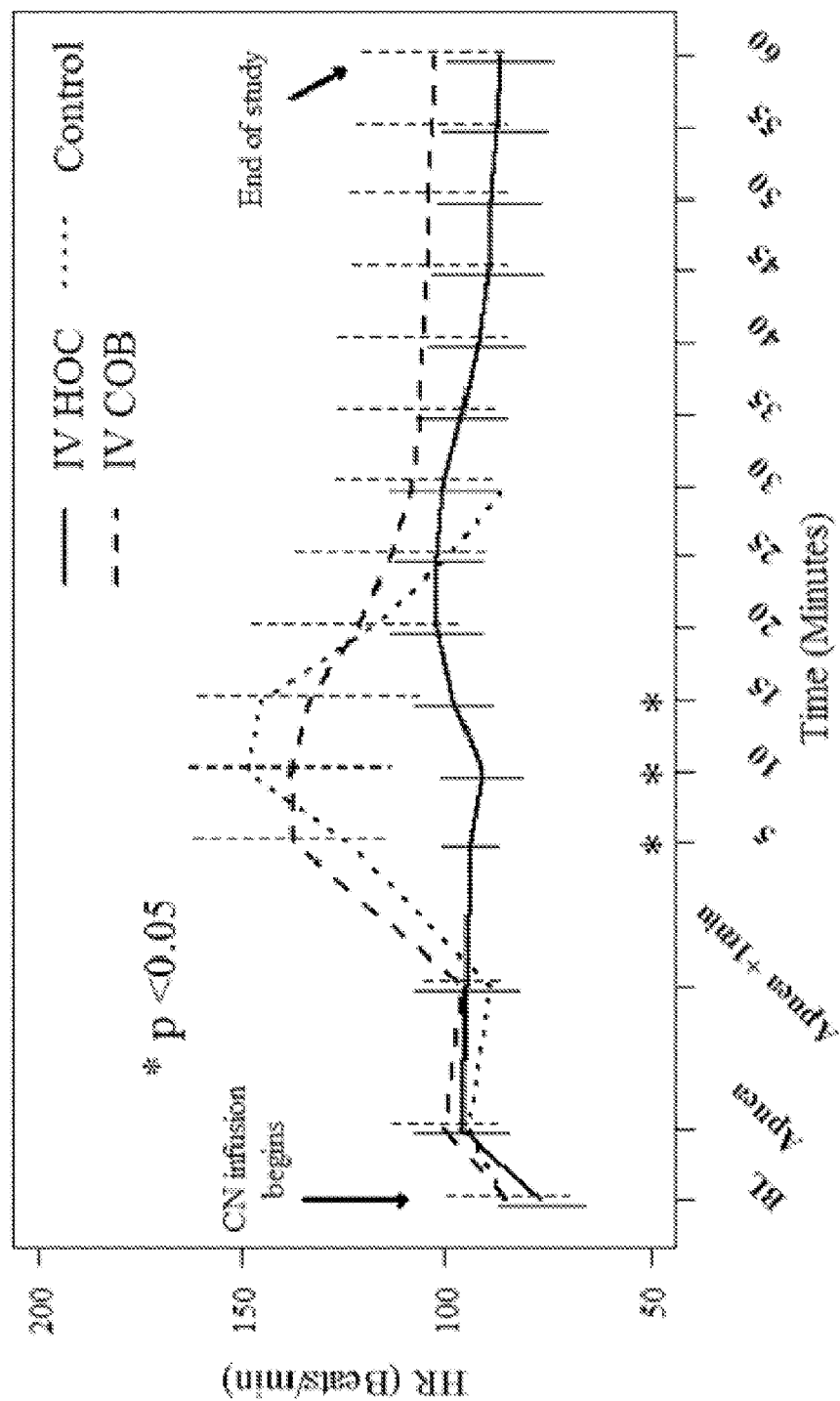
Figure 4D:
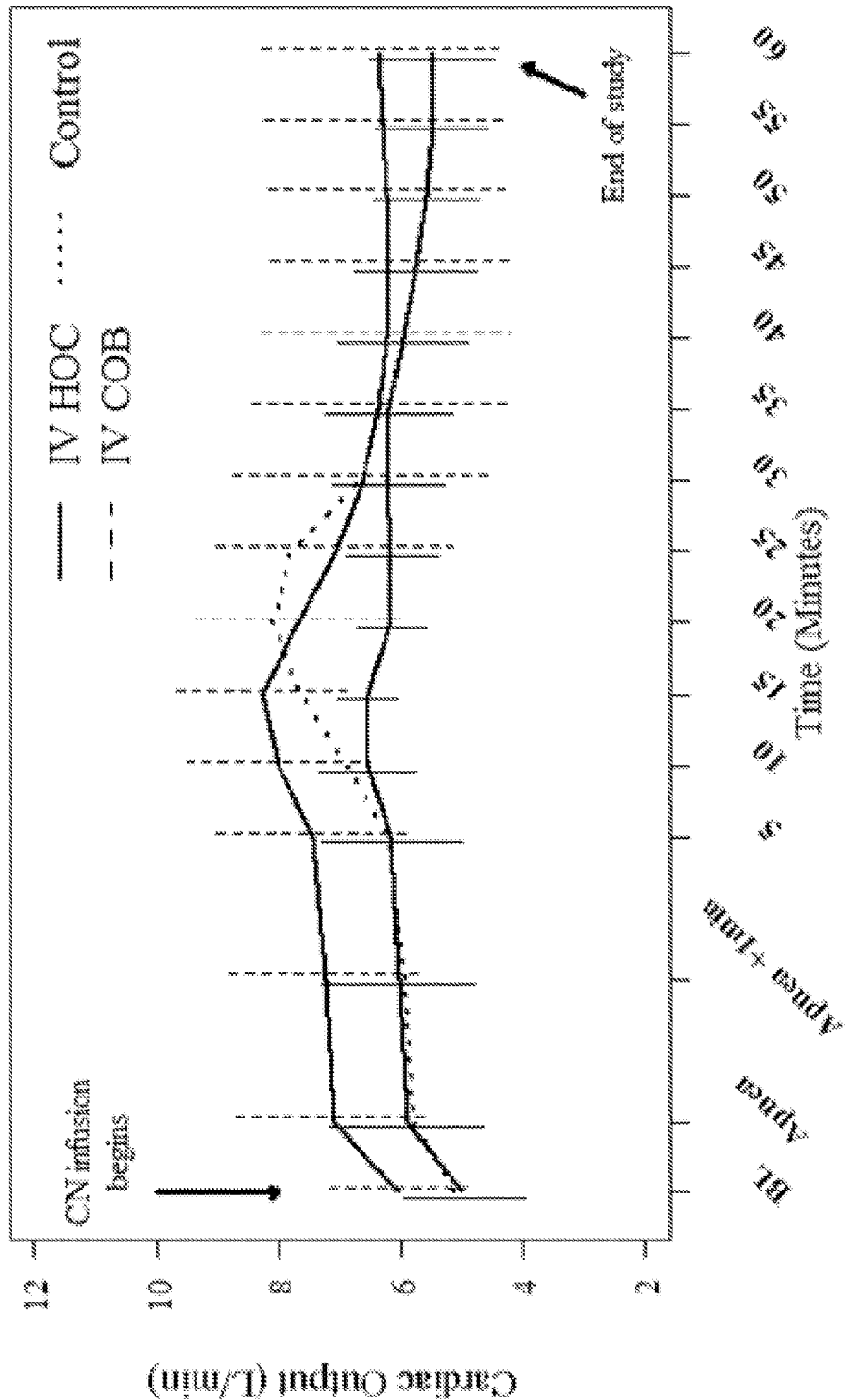
Figure 4E:
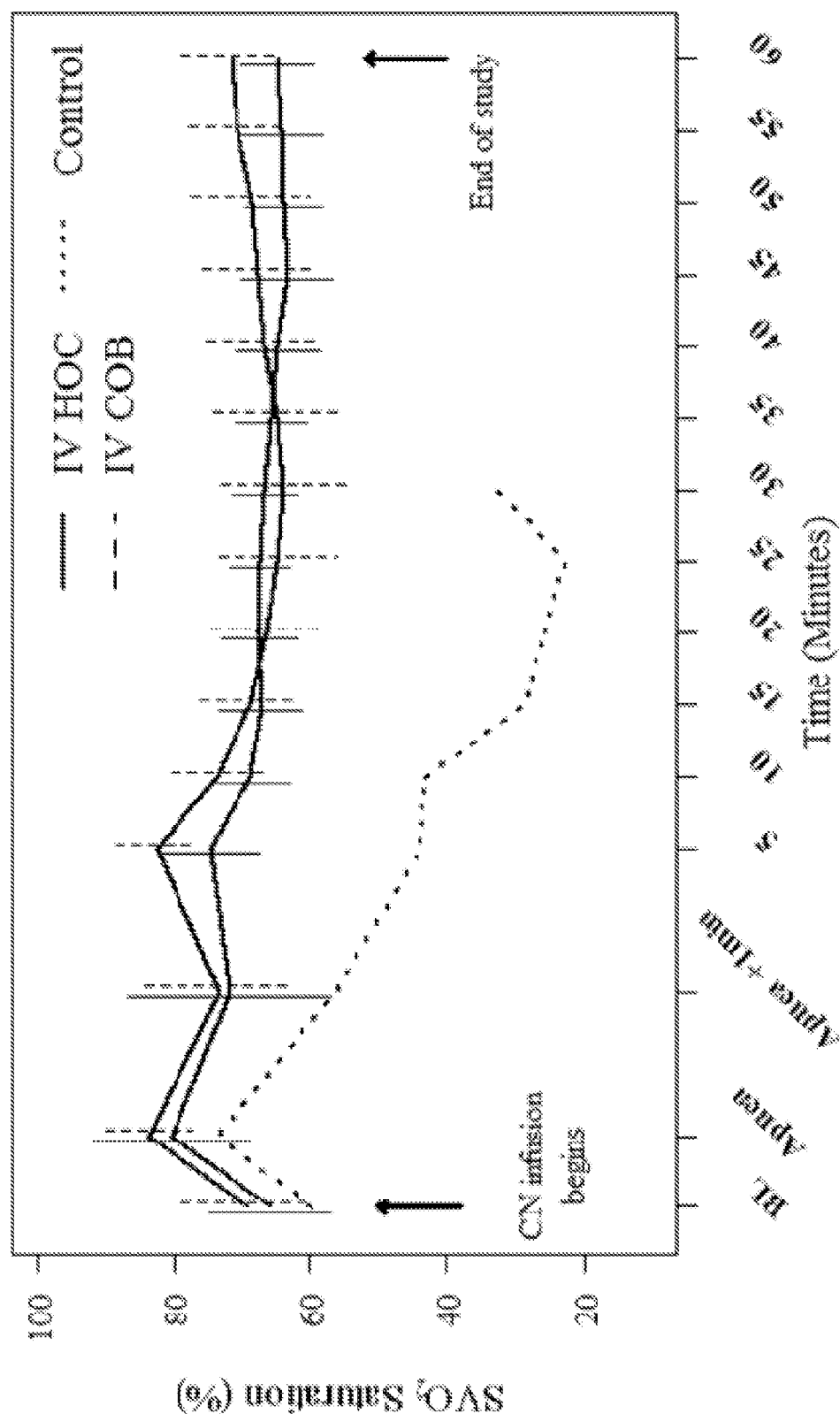

Of the treated animals that survived, respiratory rate, mean arterial pressure, heart rate, cardiac output, and central mixed venous oxygenation all trended towards baseline after treatment (FIGS. 4A, B, C, D, E). The antidote was administered at "apnea+ one minute". Values for the control arms were plotted until >50% of the animals died (30 minutes). There were no differences in respiratory rate, heart rate, cardiac output, or mixed venous oxygenation between treatment groups from time zero to 60 minutes. Mean arterial pressure (MAP) was significantly different between the two treated groups (p<0.05) but post hoc analysis at the individual time points revealed no statistical difference by the end of the experiment (88±15.2 mm Hg hydroxocobalamin, 71±10 mm Hg dinitrocobinamide). The systolic blood pressure was also different between groups (p<0.05) but similar at the end of the experiment (112 mm±14.2 mm Hg IV hydroxocobalamin, 91±15.1 mm Hg IV dinitrocobinamide).

Figure 5A:
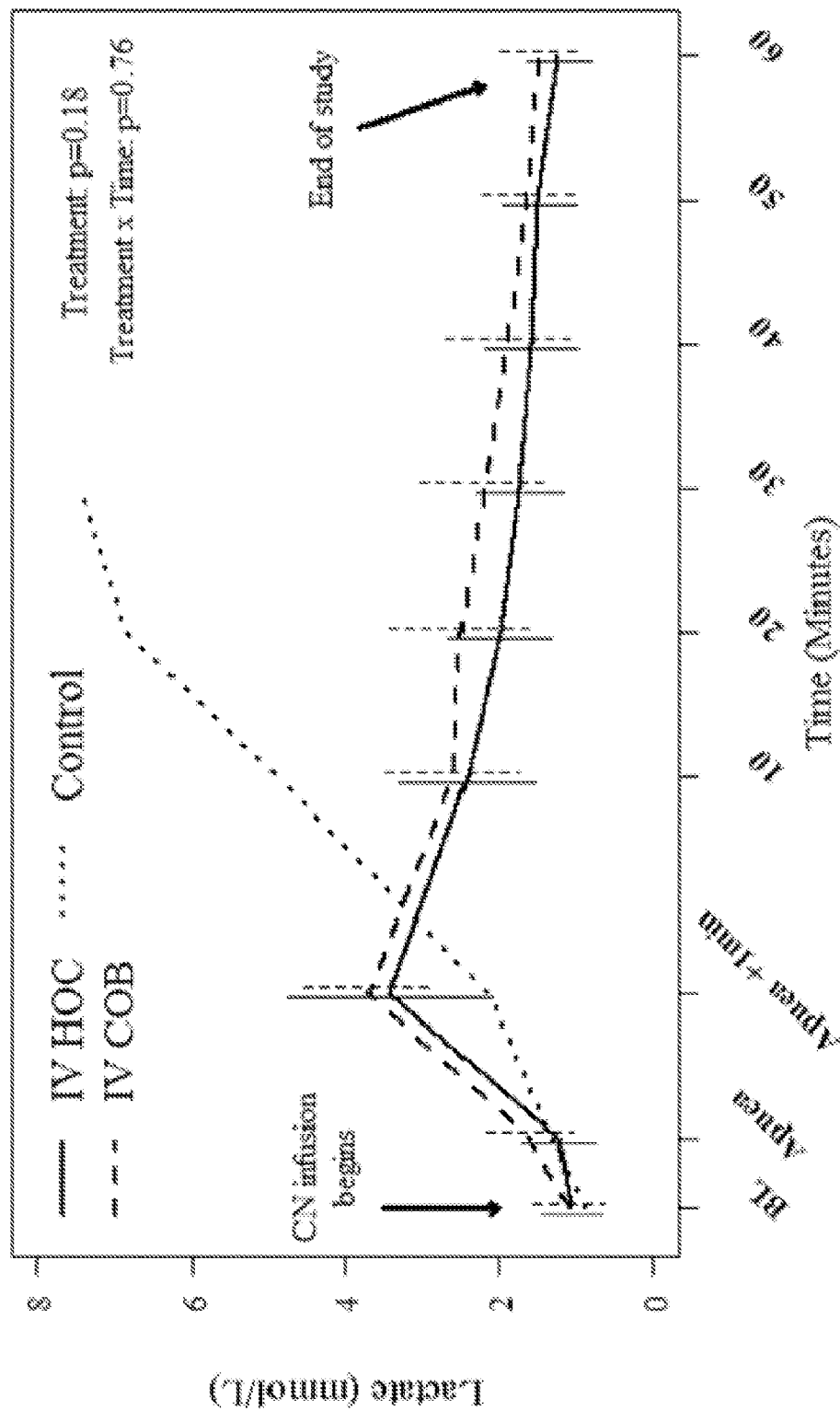
FIGS. 5A-D illustrate serum markers (lactate, bicarbonate, pH, and cyanide concentrations) of cyanide-poisoned animals over time.
Figure 5B:
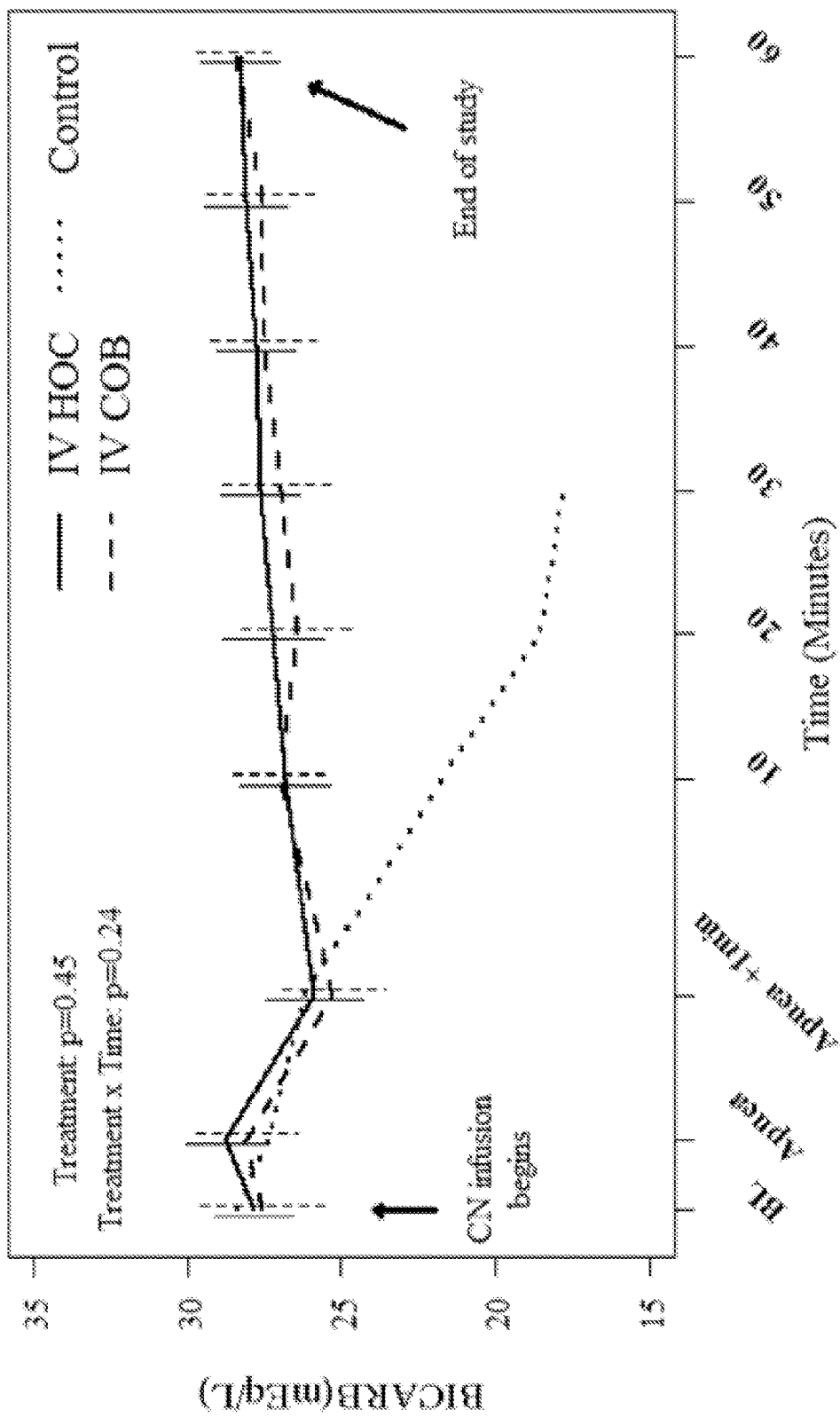
Figure 5C:
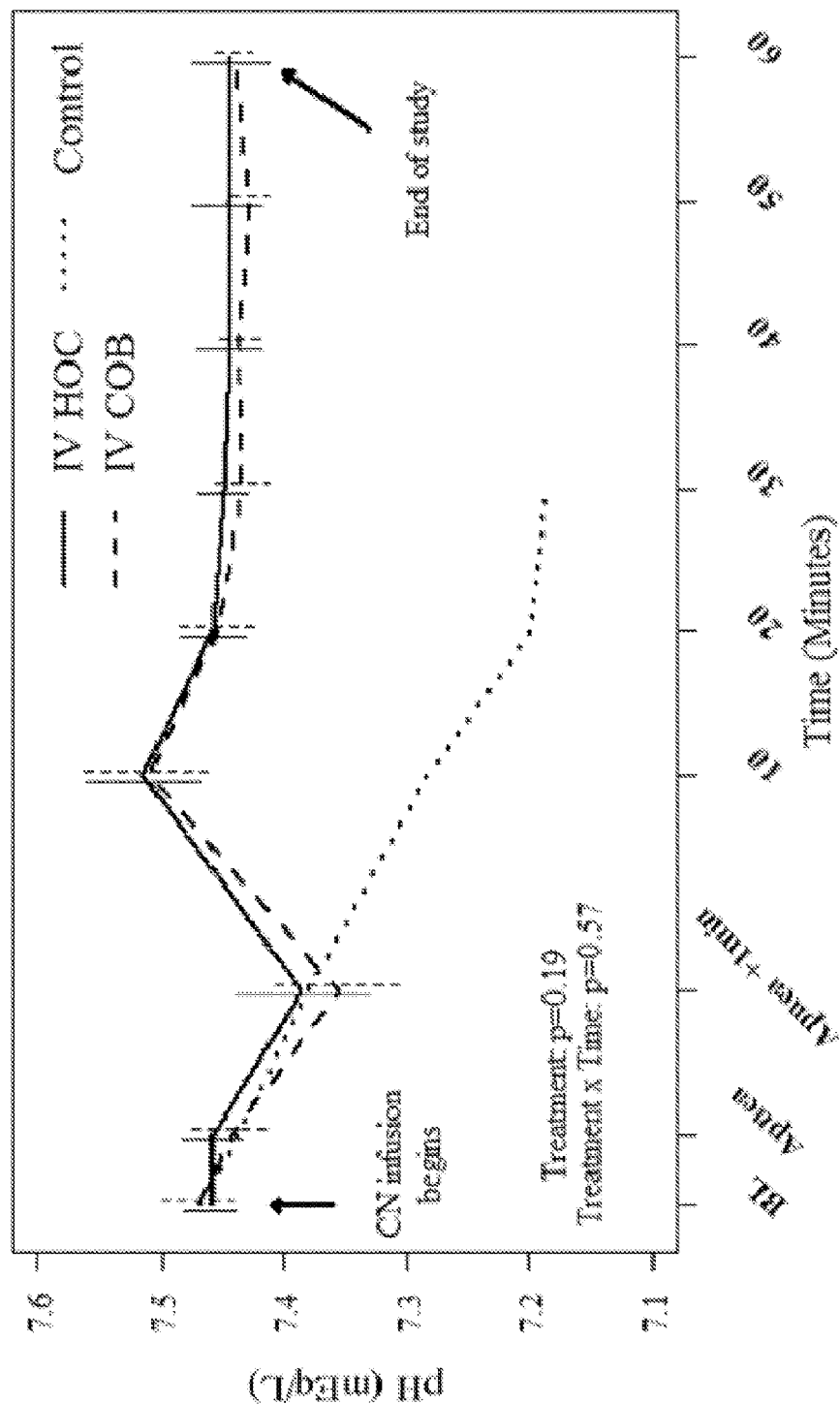
Figure 5D:
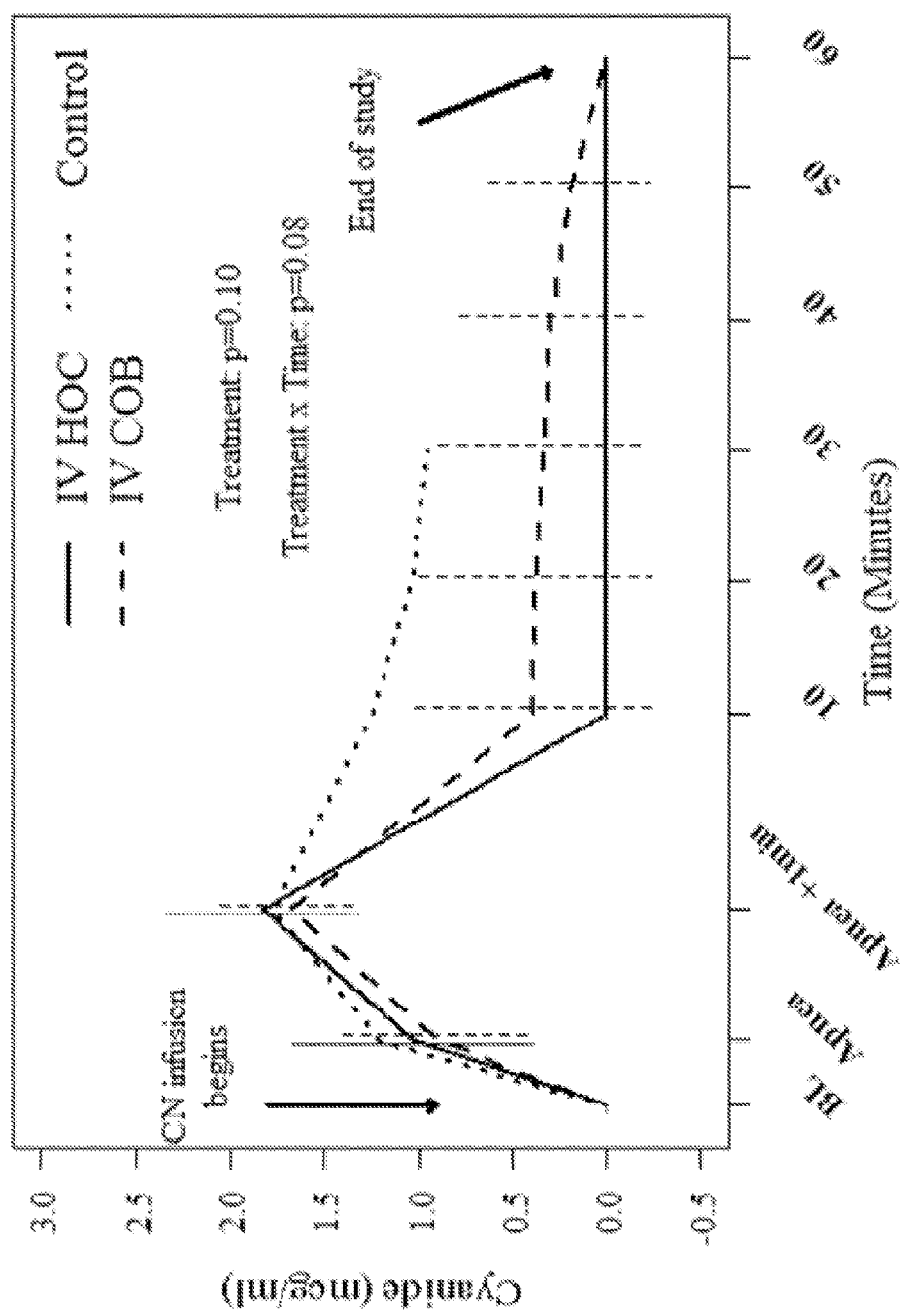

No difference was detected between treated groups in regards to lactate, bicarbonate, pH, or cyanide concentration levels from time zero through the end of the study (FIGS. 5A, B, C and D). The antidote was administered at "apnea+ one minute". Values for the control arms were plotted until >50% of the animals died (30 minutes). Lactate (1.2 vs. 1.5 mmol/L), pH (7.44 vs. 7.44) and bicarbonate (28 vs. 28 mEq/L) at 60 min were similar in the treated groups. Immediately after treatment, cyanide was not detected in 10/10 hydroxocobalamin-treated animals and 7/10 dinitrocobinamide-treated animals. Cyanide was not detectable in all of the treated animals at the end of the study.

Figure 6:
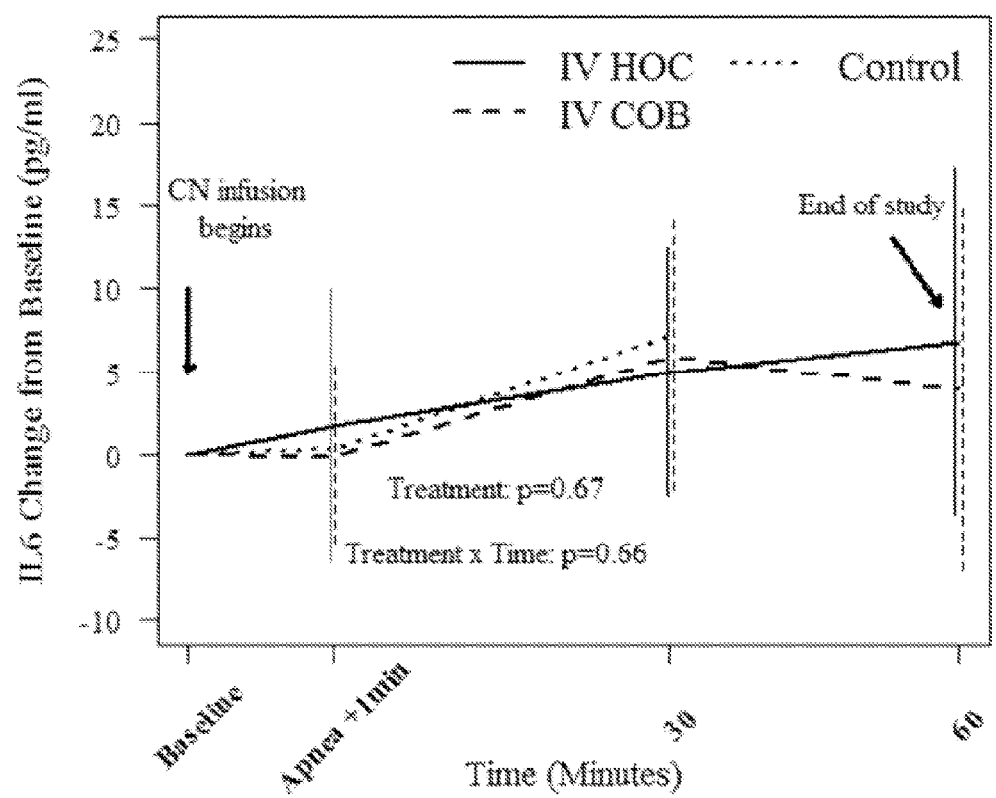
FIG. 6 illustrates serum interleukin (IL)-6 for cyanide toxic animals over time.

Inflammatory markers (TNF-a, IL-1B, IL-6, IL-8, and IL-10) increased in all groups over time compared to baseline (FIG. 6). The antidote was administered at "apnea+ one minute". Values for the control arms were plotted until >50% of the animals died (30 minutes). No differences were detected among the three groups during the experiment.

Example 2

Figure 7:
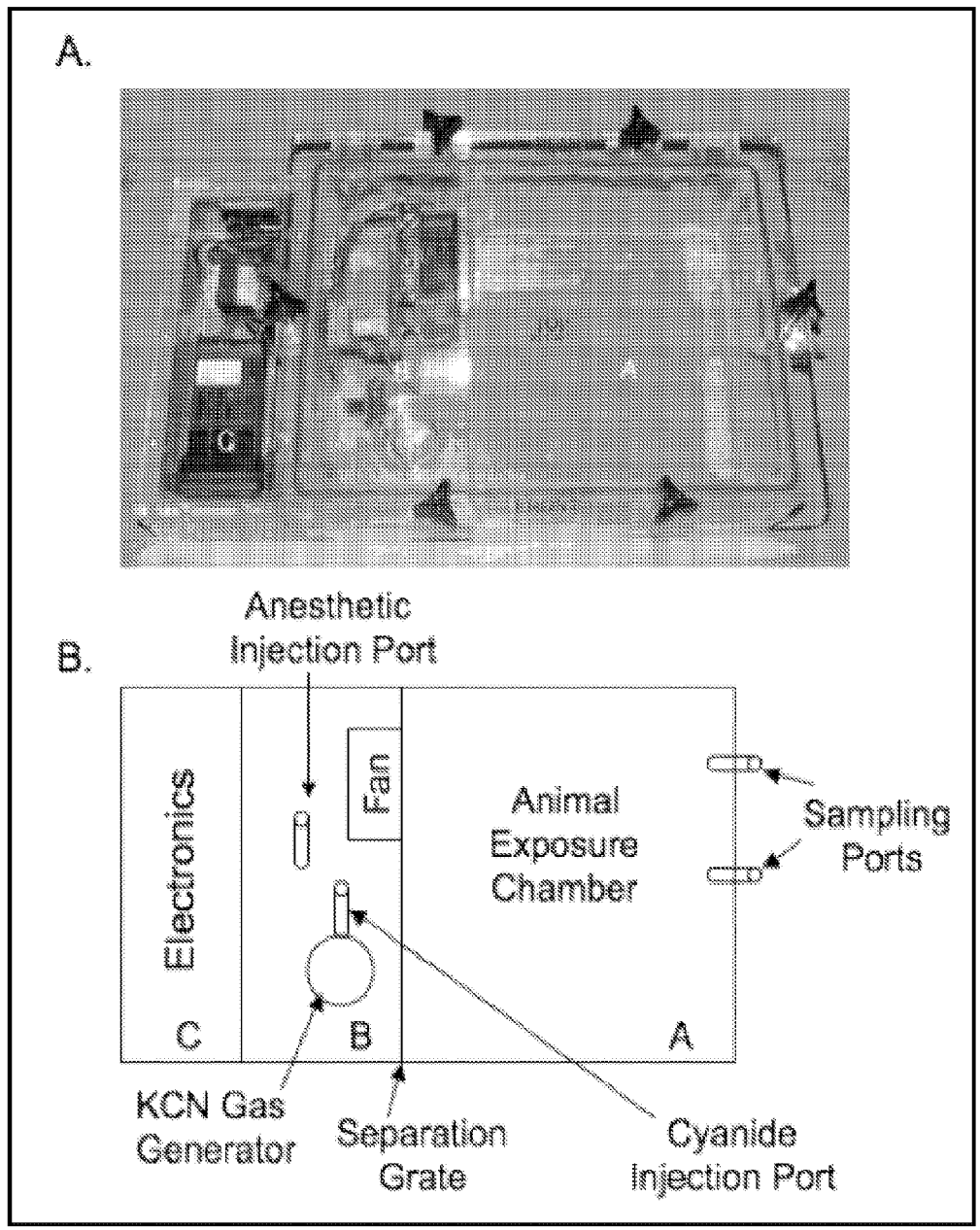
FIG. 7 illustrates a gas chamber for varying gas exposure periods.
Figure 8:
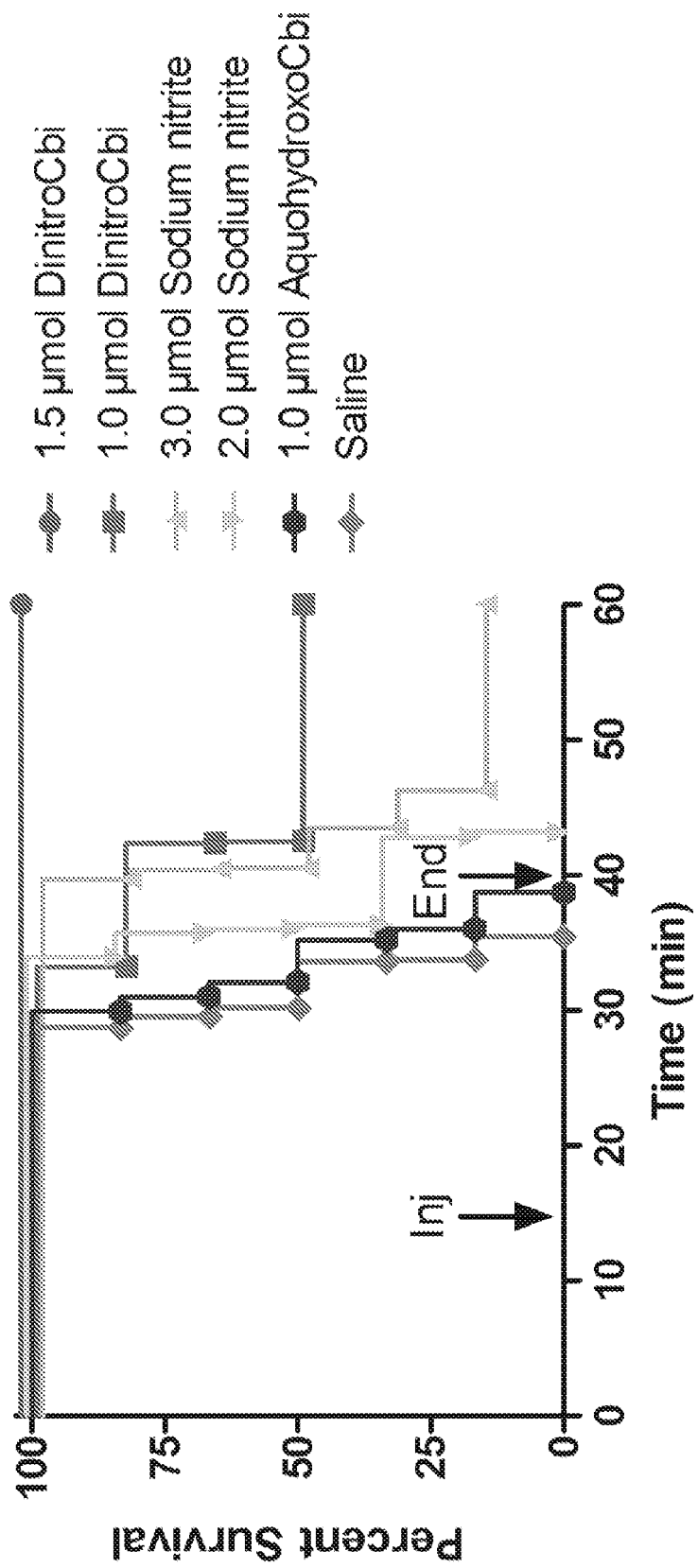
FIG. 8 illustrates efficacy of dinitrocobinamide versus aquohydroxocobinamide in lethal mouse model of cyanide poisoning.

Intramuscular Dinitrocobinamide Compared to Intramuscular Aquohydroxocobinamide in Treating Cyanide Exposure C57/Bl mice (6 animals/condition) were exposed to 587 ppm of cyanide gas for a total of 40 min in a sealed Plexiglas chamber. FIG. 7 illustrates a custom made gas chamber that allows for varying the gas exposure periods. FIG. 7A illustrates a photograph of the chamber. FIG. 7B illustrates a schematic of the chamber. The chamber is 4.3 L in volume, and maintains a constant cyanide gas concentration at a controlled temperature using a rapid circulation system. It is composed of Plexiglas and is sealed airtight by an O-ring under the lid held in place by six rapid release clasps. Section A of the chamber is the animal compartment, which holds up to four mice. It is separated from Section B by a fine plastic grate. Near the rear of the box along the grate is a circulating fan with a heater connected to a power supply in Section C. A thermistor in Section B monitors temperature, maintaining temperature at 30±0.5° C. Section C is a sealed separate container that houses all electronics. Separate ports are used for (i) injecting liquid isoflurane; (ii) injecting cyanide precursor materials; and (iii) gas sampling. After 15 min of exposure, they were removed from the chamber, and injected (Inj) intramuscularly with either 1.5 µmol dinitrocobinamide (red circles), 1.0 µmol dinitrocobinamide (green squares), 3.0 µmol sodium nitrite (salmon-colored triangles), 2.0 µmol sodium nitrite (inverted light green triangles), 1.0 µmol aquohydroxocobinamide (purple hexagons), or saline (pink diamonds). They were then placed back in the chamber for 25 min. This is referred to as the 15-25 model. This model simulates a real-life situation of people being exposed to cyanide with 15 min required for emergency medical personnel to arrive, and another 25 min required to treat and evacuate the victims from the cyanide-contaminated area. Mice that received aquohydroxocobinamide showed no better improvement in survival than mice receiving saline. However, mice that received an equal amount of dinitrocobinamide as aquohydroxocobinamide, i.e., 1 µmol, had a 50% survival rate, and mice that received 1.5 µmol of dinitrocobinamide all survived. When given by itself at amounts corresponding to that in dinitrocobinamide, sodium nitrite either had no effect (at 2 µmol corresponding to 1 µmol dinitrocobinamide) or a small effect (at 3 µmol corresponding to that in 1.5 µmol of dinitrocobinamide). The results are shown in FIG. 8.

Example 3

Analysis of Dinitrocobinamide and Aquohydroxocobinamide in Muscle Tissue

Figure 9:
FIG. 9 illustrates rabbit muscle after injection with aquohydroxocobinamide.

A New Zealand white rabbit was injected with 1 ml of a 100 mM solution of aquohydroxocobinamide in the thigh muscle. At 1 h after the injection, the site was opened, and, as shown in FIG. 9, a large gelatinous mass of dark red material (cobinamide) extruded from the opening.

Figure 10:
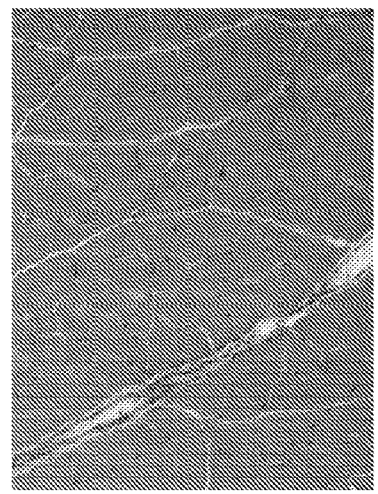
FIG. 10 illustrates mouse muscle tissue after injection with various forms of cobinamide.
Figure 10:
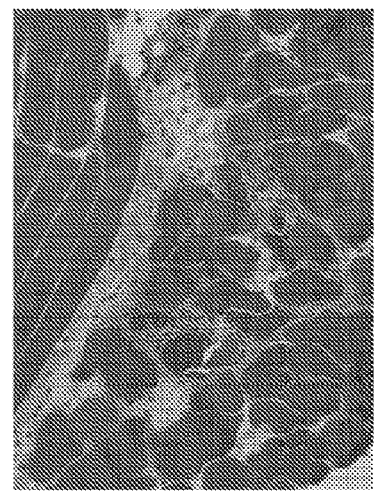
Figure 10:

Mice were injected in the thigh muscle with 50 µl of saline (FIG. 10A), 50 µl of 80 mM dinitrocobinamide (FIG. 10B), or 50 µl of 80 mM aquohydroxocobinamide (FIG. 10C). At 24 h after the injection, the mice were euthanized, their thigh muscle harvested, and frozen sections were fixed and stained. Representative areas are shown in FIG. 10. The muscle injected with dinitrocobinamide shows some infiltration of granulocytes and lymphocytes, but the muscle architecture is largely preserved and no myocyte necrosis is present. However, the muscle from the mouse injected with aquohydroxocobinamide shows severe disruption of the muscle architecture with diffuse myocyte necrosis. When harvested 7 d after injection, muscles from dinitrocobinamide-injected mice were completely normal.

Example 4

Binding of Cobinamide to the Extracellular Matrix of Skeletal Muscle

Figure 11:
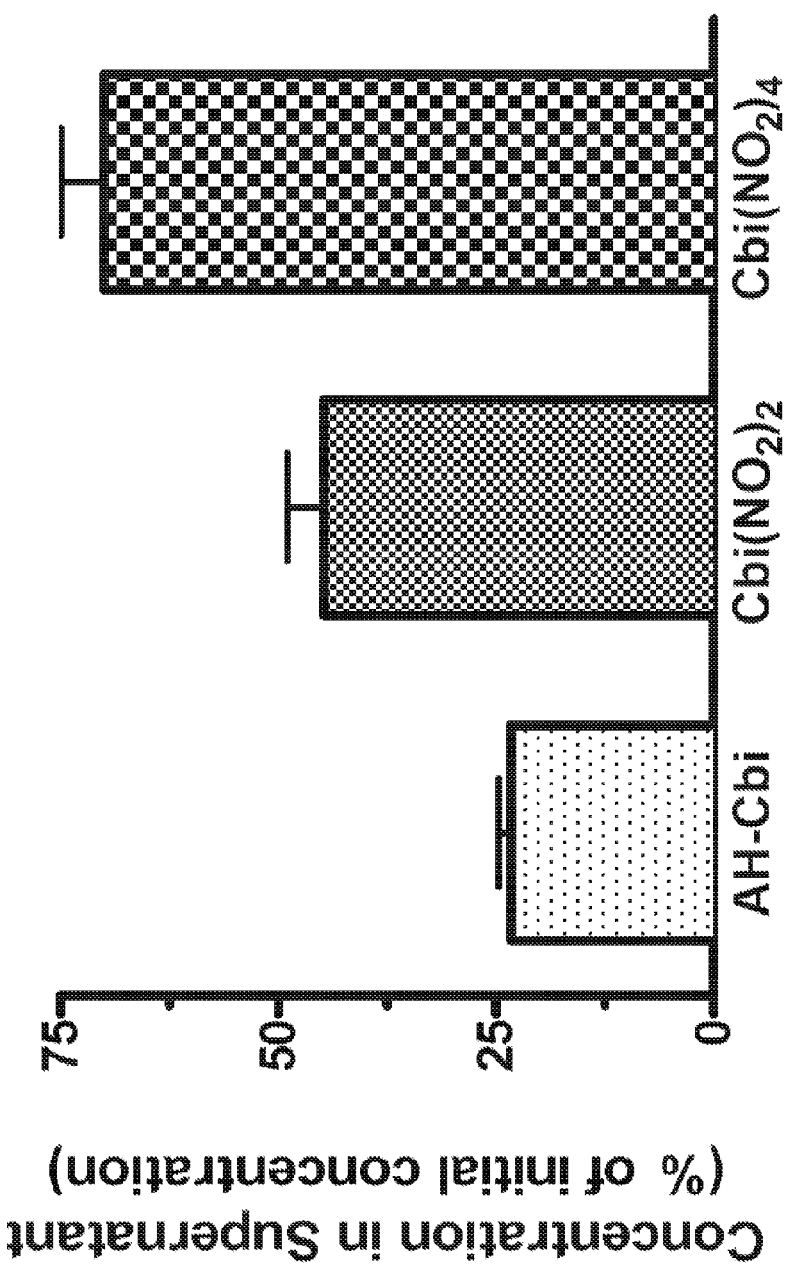
FIG. 11 illustrates binding of cobinamide to the extracellular matrix of skeletal muscle.

Extracellular matrix (ECM) of porcine skeletal muscle was generated by incubating 1 gram slices of freshly-harvested muscle with 1% Triton X-100; the solid ECM was separated from the lysed cells by centrifugation, washed three times with phosphate-buffered saline (PBS), and re-suspended in PBS. Aquohydroxocobinamide (AH-Cbi), dinitrocobinamide [Cbi(NO$_2$)$_2$], and a dinitrocobinamide solution with two added molar equivalents of sodium nitrite [Cbi(NO$_2$)$_4$] were added to the ECM at a final concentration of 1 mM. After a 30 min incubation with gentle shaking, the ECM was removed, and the concentration of the cobinamide derivative in the supernatant was measured. FIG. 11 illustrates the data which are expressed as a percent of the initial 1 mM cobinamide concentration. Thus, only 24% of the aquohydroxocobinamide was recovered in the supernatant (76% bound to the ECM), while 45% of dinitrocobinamide remained in the supernatant (55% bound to the extracellular matrix), and 71% of dinitrocobinamide with two added molar equivalents of sodium nitrite remained in the supernatant (only 14% bound to the extracellular matrix). The data are the mean±SEM of three independent experiments. Thus, dinitrocobinamide binds much less to the ECM of muscle than aquohydroxocobinamide. Sulfitocobinamide was similarly tested and only ~10% bound to the matrix.

Figure 12:
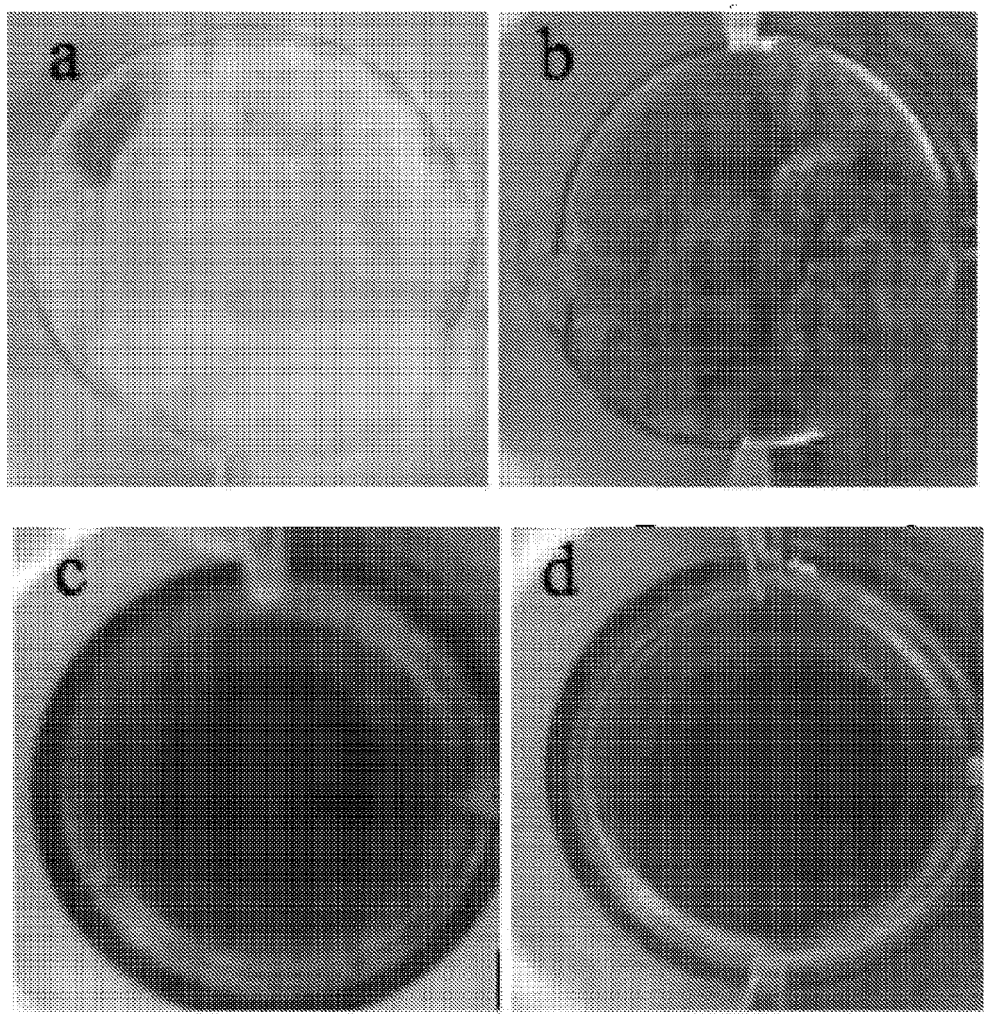
FIG. 12 illustrates ECM pieces for use in assay to identify binding of cobinamide to ECM.

Porcine skeletal muscle ECM was prepared as described by Brenner M. in *J Biomed Opt.* 2010; 15(1):017001. After decellularization, 0.5 g of ECM pieces were placed in 24-well plates, and cobinamide solutions of known concentration were added. FIG. 12 illustrates a) decellularized skeletal muscle ECM pieces, b) ECM pieces removed after 8 hours in c) 1 mM AH-Cbi solution, d) AH-Cbi solution after ECM is removed. Dicyanocobinamide (CN-Cbi) was hypothesized not to interact with the ECM, and thus was used as a negative control. At various time points, samples of the solution were taken to measure cobinamide concentration using a NanoDrop 2000c Spectrophotometer (Thermo Scientific). Peak absorbance for AH-Cbi, NN-Cbi, and CN-Cbi were 346 nm, 349 nm, and 364 nm respectively. ECM water content was determined by lyophilizing ECM pieces and calculating the change in weight attributed to water loss. Triton (0.5%), NaCl (1 kEq), and NaNO$_2$ (2 Eq) were added to determine the nature of the cobinamide-ECM interaction.

Figure 13:
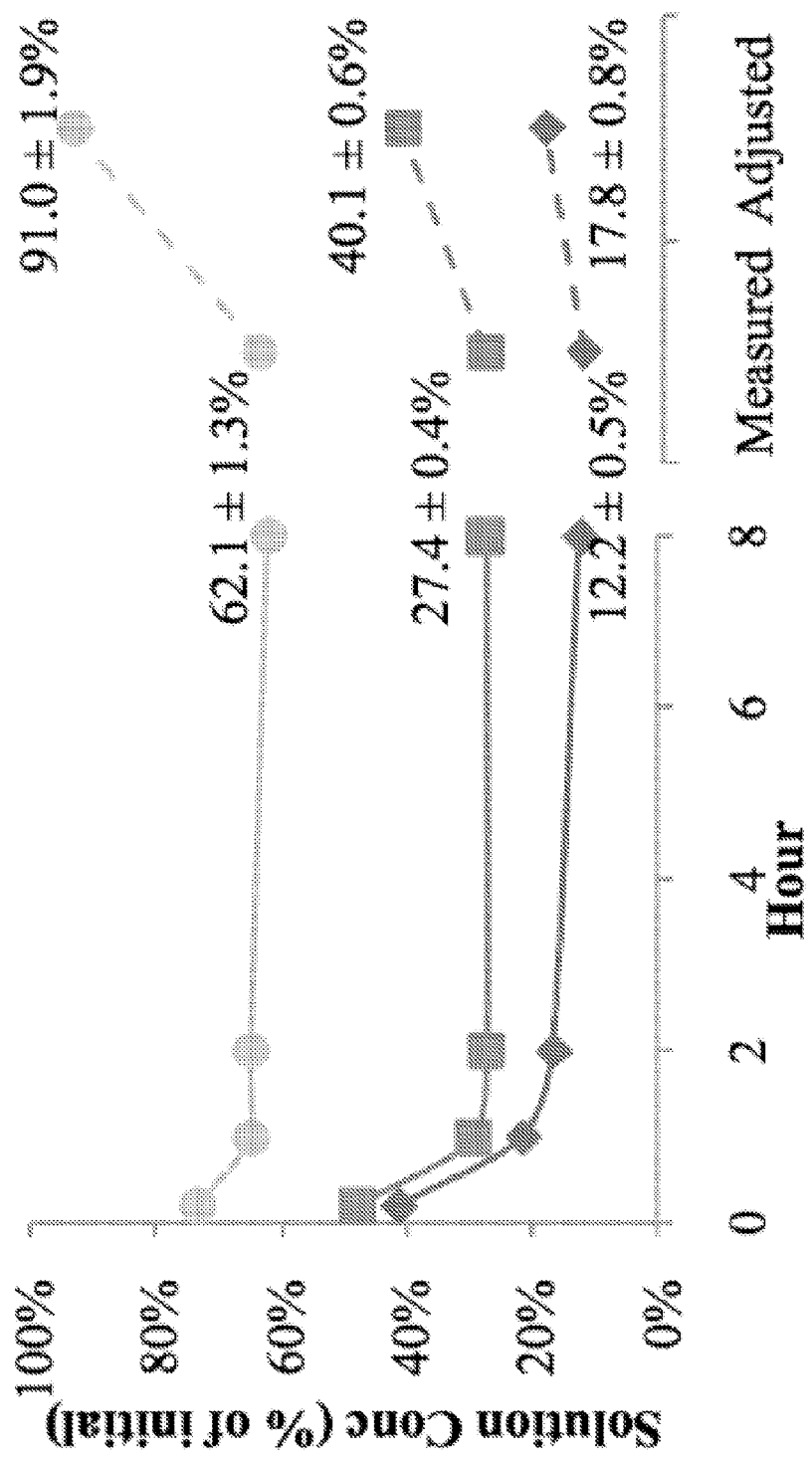
FIG. 13 shows the change in concentration of cobinamides in solution after contact with ECM.

After 4-8 h, less AH-Cbi remained in solution compared to NN-Cbi (FIG. 13), indicating a greater degree of sequestration by skeletal muscle ECM. CN-Cbi concentration was 60-65% of the initial concentration. The loss of cobinamide was hypothesized to be due to its distribution into the interstitial fluid of the highly hydrated ECM pieces. To account for this additional fluid, the water content of ECM pieces was determined and found to be 94%. After correcting for this effect, CN-Cbi was shown to interact minimally with ECM, and the difference between AH-Cbi and NN-Cbi is greater. FIG. 13 illustrates the concentration of AH-Cbi (diamonds), NN-Cbi (squares), and CN-Cbi (circles) when 1 mL of 1 mM solution is added to 0.5 g of skeletal muscle ECM after 12 min, 1 h, 2 h, and 8 h. Values are reported as a percentage of the initial concentration, where a lower percentage suggests stronger ECM interaction. Dashed lines show adjustments for ECM water content. Adding Triton or NaCl to the solution did not affect AH-Cbi or NN-Cbi binding to ECM, suggesting the interaction was neither hydrophobic nor ionic. However, adding NaNO$_2$ increased the concentration of NN-Cbi remaining in solution significantly (25.6% to 50.0%), indicating that NN-Cbi improves IM absorption by competition of the nitrite group with an ECM moiety.

Example 5

Reaction of Sulfide with Cobinamide

Figure 14:
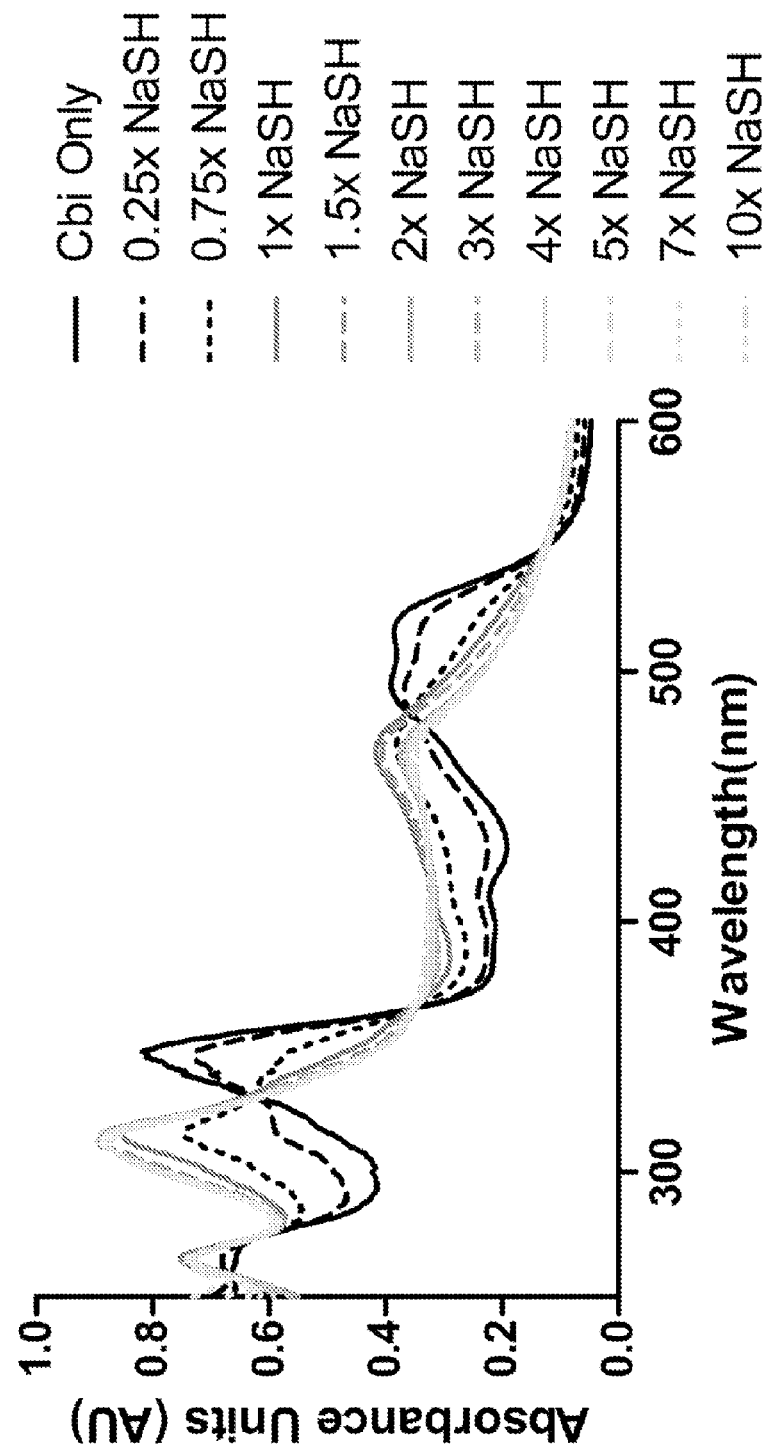
FIG. 14 is a UV-Vis spectrum of cobinamide's reaction with sulfide.

To a 25 µM cobinamide with water and hydroxyl ligands solution, increasing concentrations of sodium hydrogen sulfide (NaSH) were added from 6.25 µM to 250 µM. The UV-vis spectrum from 250 to 600 nM was recorded after each addition. Note no change in spectrum after 50 µM NaSH (2×) was added. The results are shown in FIG. 14. The ultraviolet-visible (UV-vis) spectrum of cobinamide is distinctive, and molecules that react with cobinamide change the spectrum. Sulfide caused a marked change in the UV-vis spectrum of cobinamide at concentrations as low as one-fourth that of cobinamide, and, at sulfide concentrations twice that of cobinamide, no further change in the spectrum occurred. This suggested that two sulfide molecules were reacting with cobinamide, and, based on the spectral changes, it appeared that sulfide was reducing cobinamide from the +3 to the +2 valency state, i.e., from cobinamide (III) to cobinamide(II). A detailed kinetic and structural analysis of cobinamide's reaction with sulfide was performed. The reaction proceeds in three steps: (i) formation of three different complexes between cobinamide and sulfide, i.e., (HO-)(HS-)cobinamide(III), (H2O)(HS-)cobinamide(III), and (HS-)2cobinamide(III); (ii) inner-sphere electron transfer in the two complexes with one coordinated HS- to form the reduced cobinamide complex [(H)S]cobinamide (II); and (iii) addition of a second molecule of HS- to the reduced cobinamide. The final product of the reaction is a complex of cobinamide(II) with the anion-radical SSH$_2^-$. Thus, cobinamide is reduced by sulfide, and, in the process, consumes and binds two sulfide molecules.

Figure 15:
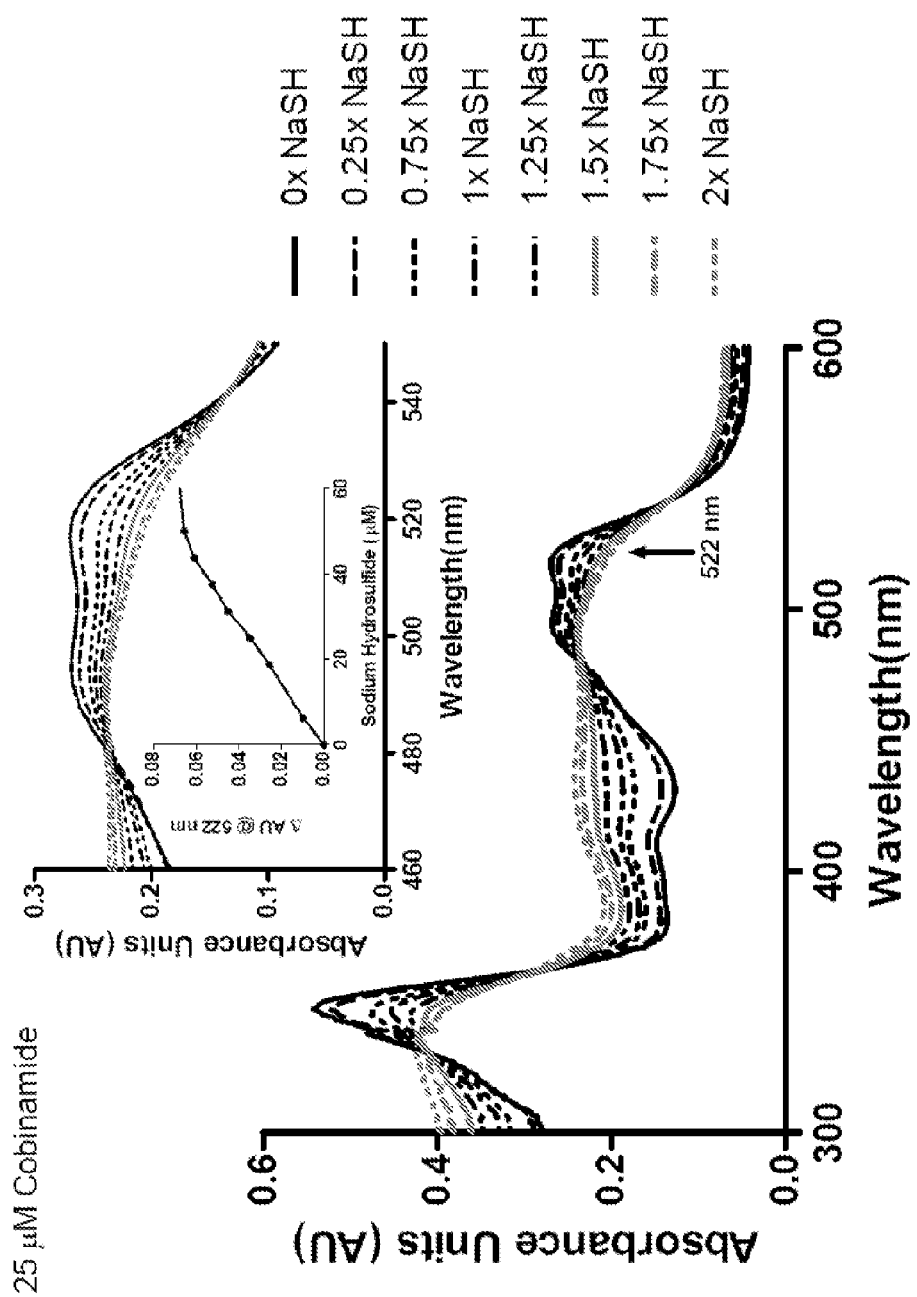
FIG. 15 illustrates binding data of cobinamide with sulfide.
Figure 16:
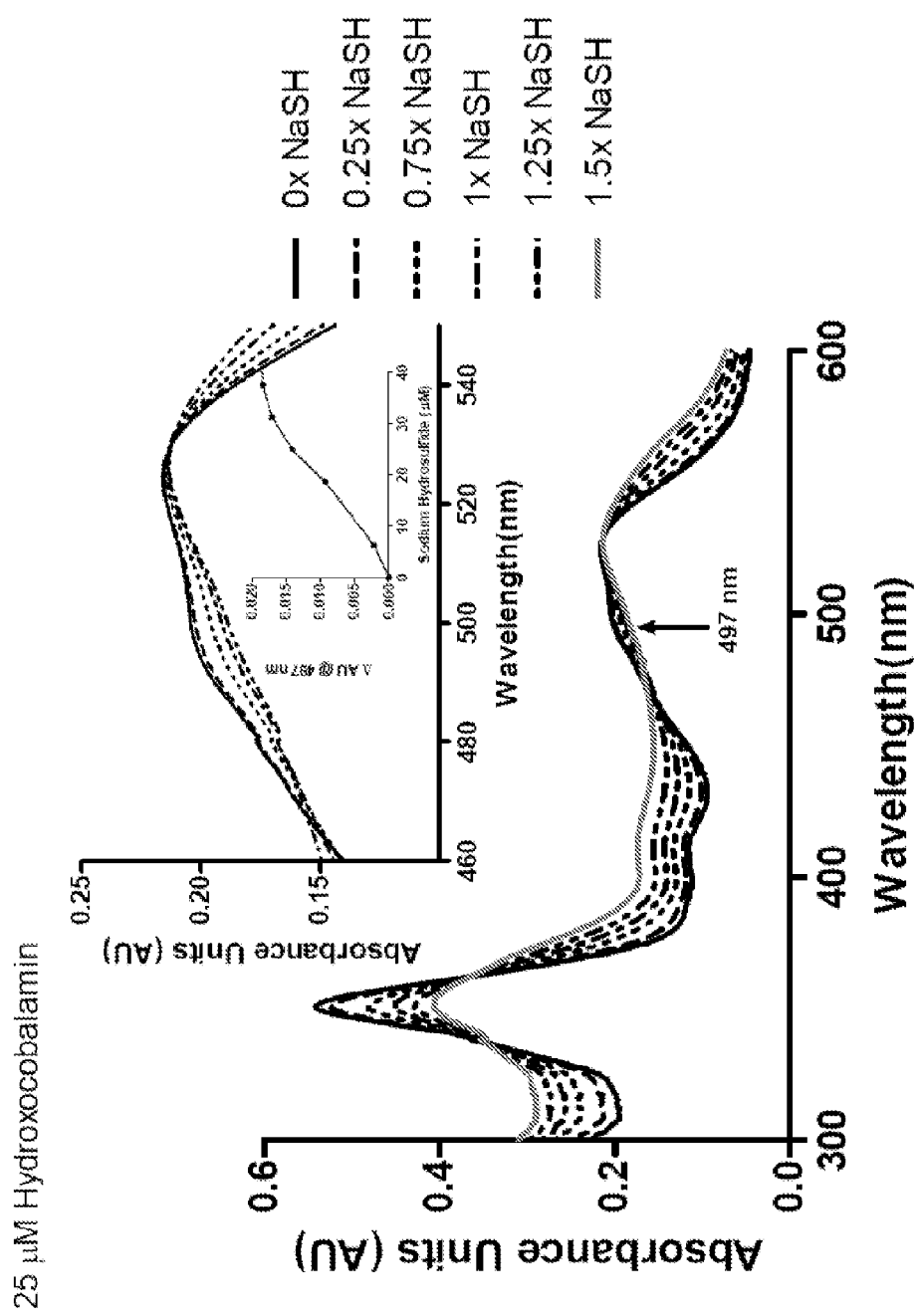
FIG. 16 illustrates binding data of hydroxocobalamin with sulfide.

FIGS. 15 and 16 illustrate binding data of cobinamide (in aqueous solution such that cobalt in cobinamide is bound to a combination of water and hydroxide) as well as hydroxocobalamin. Increasing amount of NaSH was added to 25 µM cobinamide (FIG. 15) or hydroxocobalamin (FIG. 16) solution at pH 7. Large Inset. The spectrum between 460 nm and 550 nm of cobinamide (FIG. 15) or hydroxocobalamin (FIG. 16). Small Inset. The absorbance change of cobinamide solution at 522 nm (FIG. 15) or hydroxocobalamin solution at 497 nm (FIG. 16) was plotted against NaSH concentrations.

Example 6

Cobinamide Rescue of Cells from Sulfide Poisoning

Figure 17:
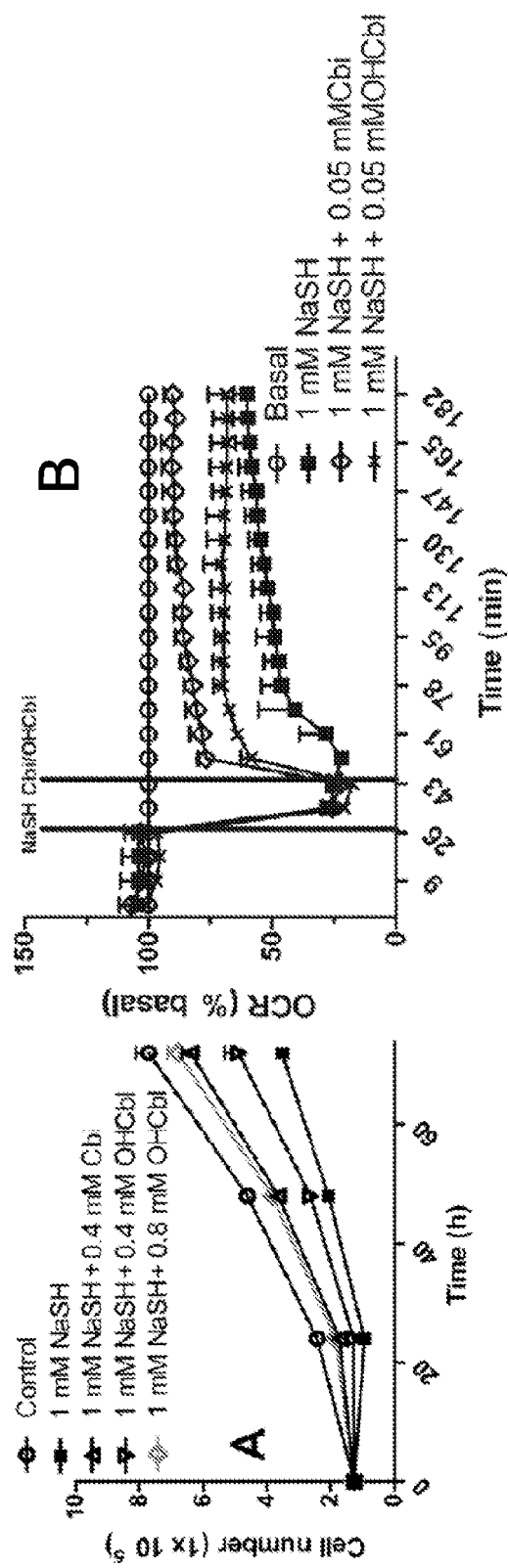
FIG. 17 illustrates cobinamide rescue of cells from sulfide poisoning.

COS-7 monkey kidney fibroblasts were treated with 1 mM sodium hydrogen sulfide (NaSH) for two hours; during the second hour either cobinamide (Cbi) or hydroxocobalamin (OHCbl) were added at the indicated concentrations. Cell growth was measured over the next 72 h. The exposure markedly inhibited the cells subsequent growth (FIG. 17A). Adding 0.4 mM cobinamide (in aqueous solution such that cobalt in cobinamide is bound to a combination of water and hydroxide) to the cells during the second hour of sulfide exposure almost returned the cell's growth rate to that of control cells. Hydroxocobalamin was also tested and it was found that a concentration of 0.4 mM had a small effect, while 0.8 mM yielded similar results as 0.4 mM cobinamide. Thus, in these experiments, cobinamide was twice as potent as hydroxocobalamin.

Because sulfide is known to inhibit mitochondrial cytochrome c oxidase and because mitochondrial respiration accounts for >90% of cellular oxygen consumption, the effects of sulfide on cellular oxygen consumption using an XF Extracellular Flux Analyzer (Seahorse Bioscience) was studied. This instrument allows real-time measurement of oxygen consumption without disturbing cells, and it allows drugs to be added sequentially to the cells. Adding 1 mM NaSH to COS-7 cells rapidly and markedly reduced the cells' oxygen consumption rate (FIG. 17B). Adding as little as 50 μM cobinamide quickly and almost completely reversed the effect of sulfide. Adding 50 μM hydroxocobalamin to sulfide-treated cells also quickly increased oxygen consumption, but, the effect was of significantly lower magnitude than with cobinamide, and, by the end of the experiment, the cells treated with NaSH alone had the same oxygen consumption rate as those that had received hydroxocobalamin. The partial reversal in the cells treated with NaSH only was likely due to NaSH coming out of the medium as $H_2S$ gas, and thus hydroxocobalamin's effect is hard to evaluate. FIG. 17B demonstrates oxygen consumption rate (OCR) of the COS-7 cells which was measured continuously. At the indicated time 1 mM sodium hydrogen sulfide (NaSH) was added, followed by either 50 μM cobinamide (Cbi) or 50 μM hydroxocobalamin (OHCbi). Cells shown as "basal" received no additions.

Figure 18:
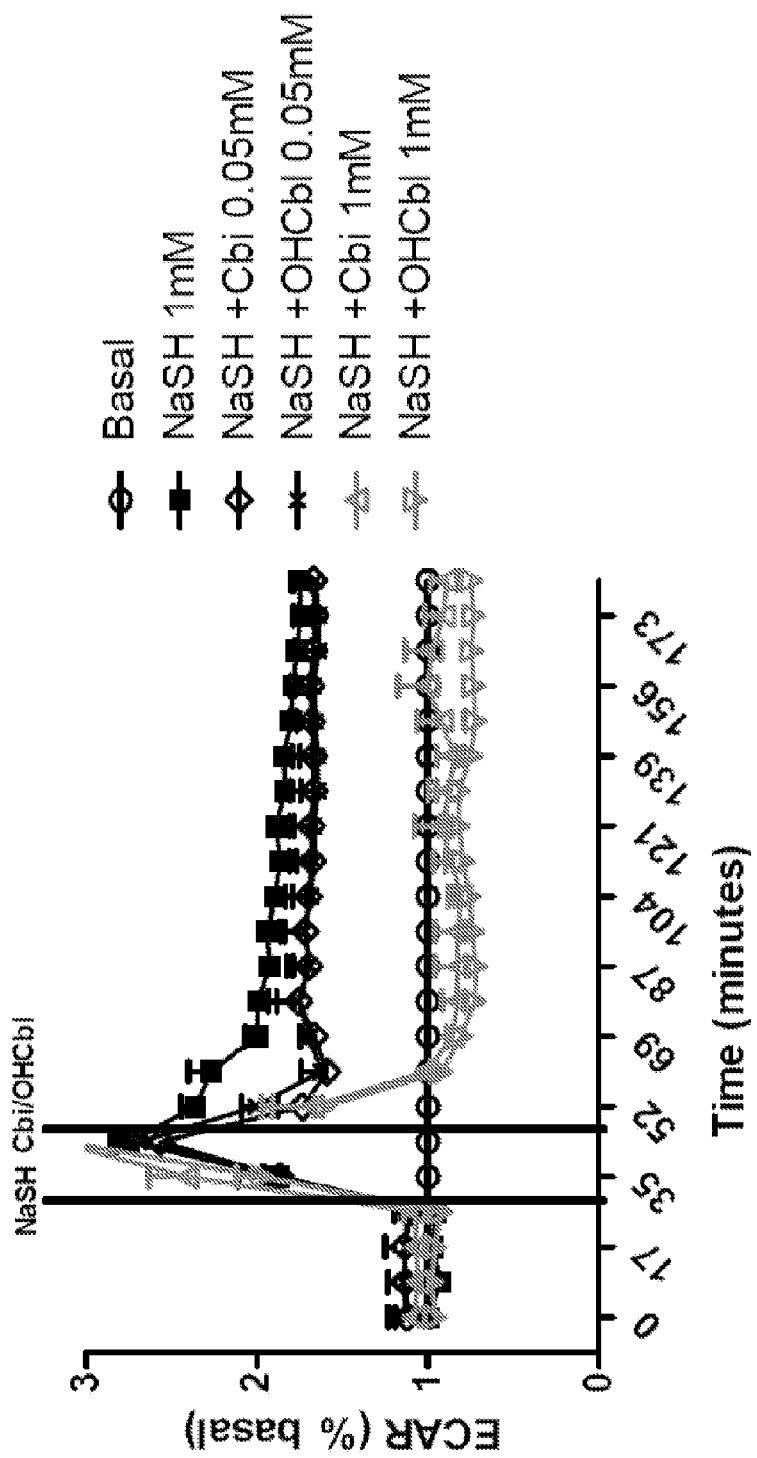
FIG. 18 illustrates extracellular acidification rates of cells.

FIG. 18 illustrates extracellular acidification rates.

Figure 19:
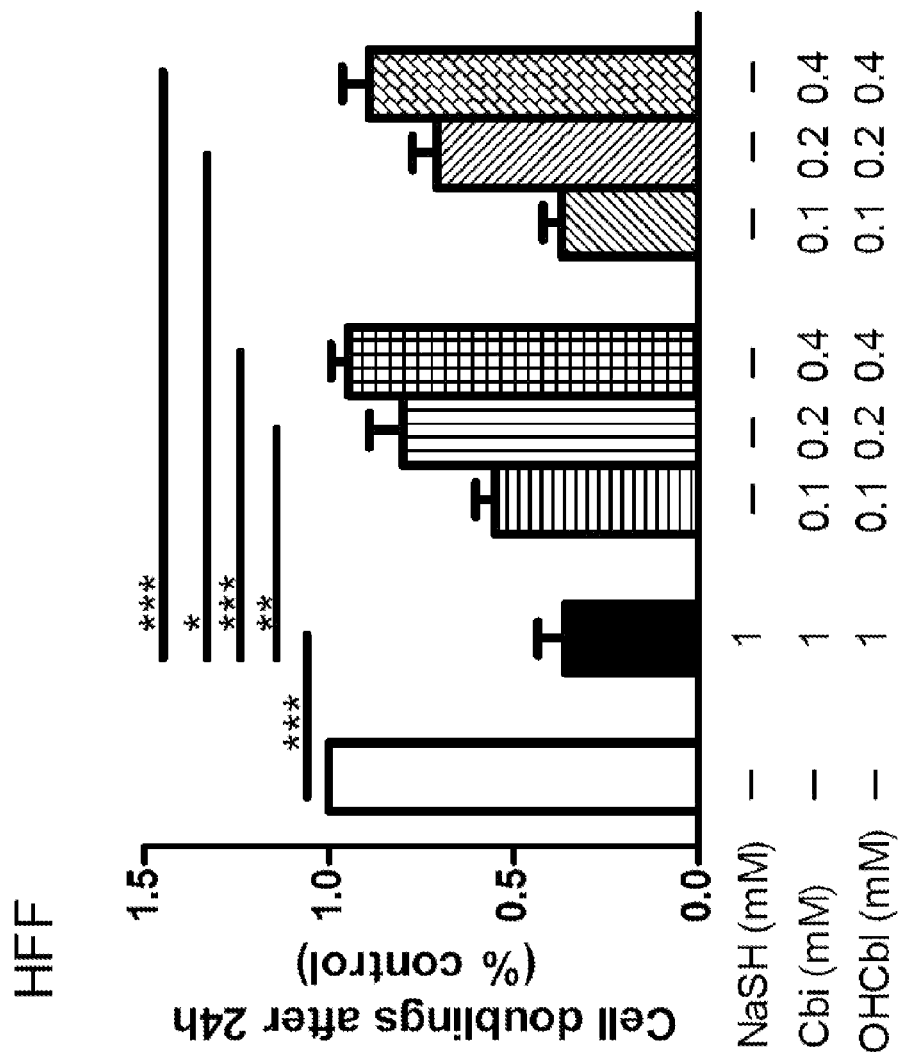
FIG. 19 illustrates normalized cell doublings in HFF calculated at 24 hours after exposure to NaSH.

Human foreskin fibroblasts (HFF) were grown in MEM supplemented with 10% fetal bovine serum. Cells were plated in 24-well plate at the density of 40000 cells/well 24 hrs before NaSH exposure. At t=2 h, cells were washed with phosphate buffered saline (PBS) and fresh medium was added. Cells then were counted at 24, 48 and 72 hrs using a TC20 Automatic Cell Counter (Bio-Rad, Hercules, Calif.). HFF were exposed to 1 mM NaSH for 1 hour before treated with cobinaminde (Cbi) or hydroxocobalamin (OHCbl) for another hours. FIG. 19 illustrates normalized cell doublings in HFF calculated at 24 hours after exposure. All data shown are the means±SEM; n>3 per group.

Example 7

Cobinamide Rescue of *D. melanogaster* from Sulfide Poisoning

Figure 20:
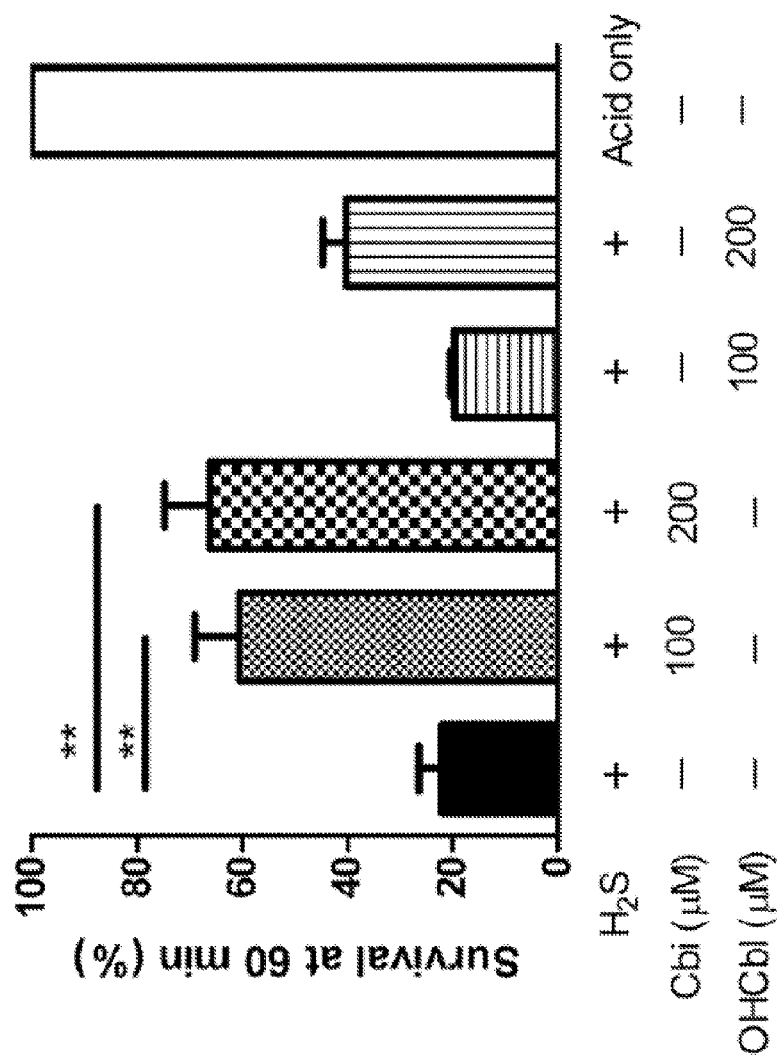
FIG. 20 illustrates cobinamide rescue of flies from sulfide poisoning.

Hydrogen sulfide gas was generated in small tightly-capped vials by placing a small amount of a NaSH solution on 0.5×0.5 cm squares of paper that had been soaked previously in acid. The acid converted the NaSH to $H_2S$, which is fully volatile at room temperature. The flies were exposed to $H_2S$ gas for 5 min, which results in the flies falling unconscious. The flies were transferred to new vials and observed their recovery over the next 60 min. Since it is technically difficult to inject flies, cobinamide and hydroxocobalamin were administered to the flies by having had the flies feed on food containing the drugs for one week prior to the sulfide exposure. About 20% of the flies that had not received antidote recovered, while ~60% and 70% of the flies that ate food containing 100 and 200 μM cobinamide, respectively, recovered (FIG. 20). In contrast, no improvement in recovery occurred in flies that ate food containing 100 μM hydroxocobalamin and only a 40% recovery rate occurred in flies that ate food containing 200 μM hydroxocobalamin. Cobinamide was more effective at rescuing flies than hydroxocobalamin. The difference in potency between the two agents was not due to differences in drug absorption, because HPLC analyses showed that the cobinamide and hydroxocobalamin concentrations in the flies were similar at each of the two drug concentrations.

Figure 21:
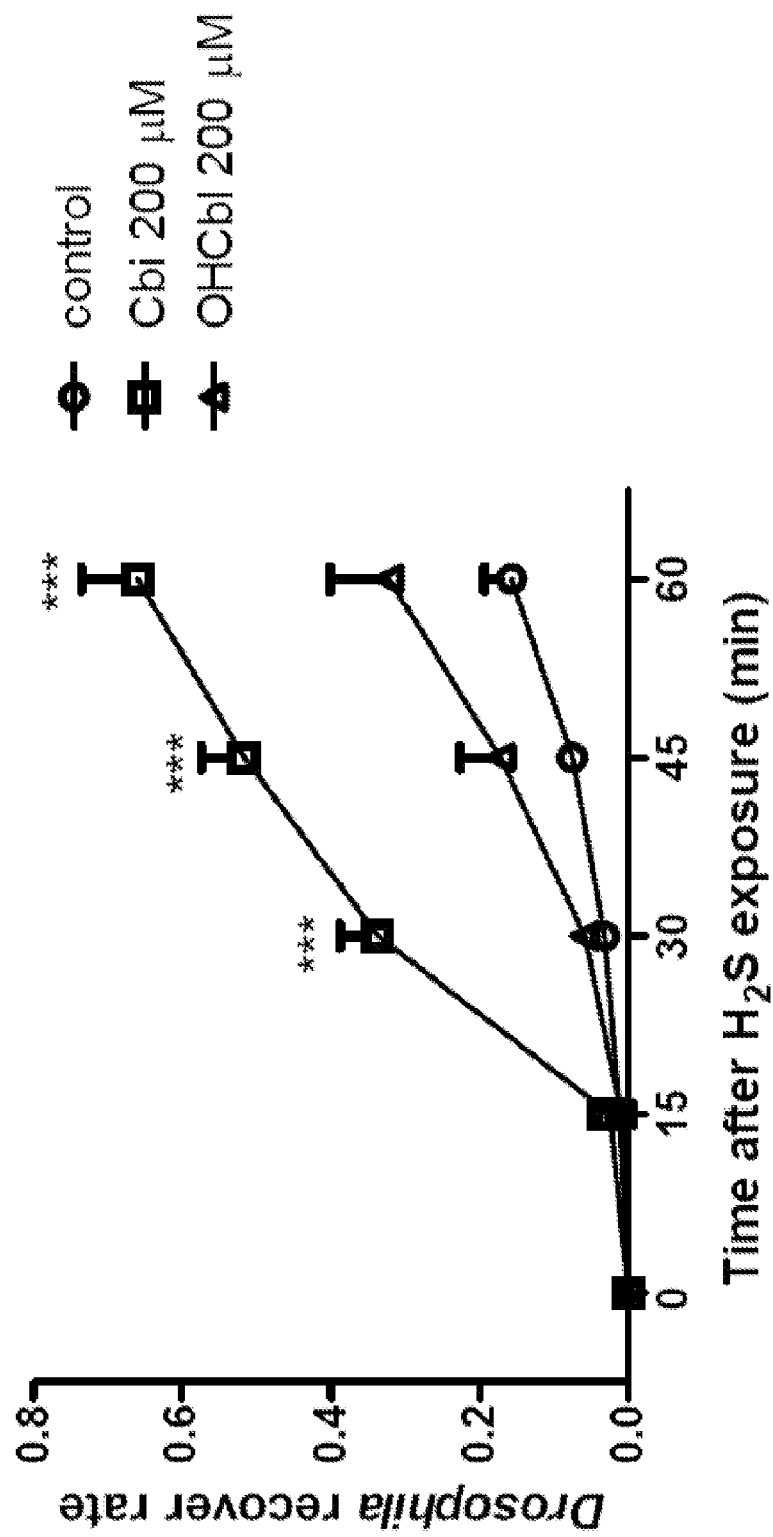
FIG. 21 illustrates fly recovery rate after exposure to $H_2S$.
Figure 22:
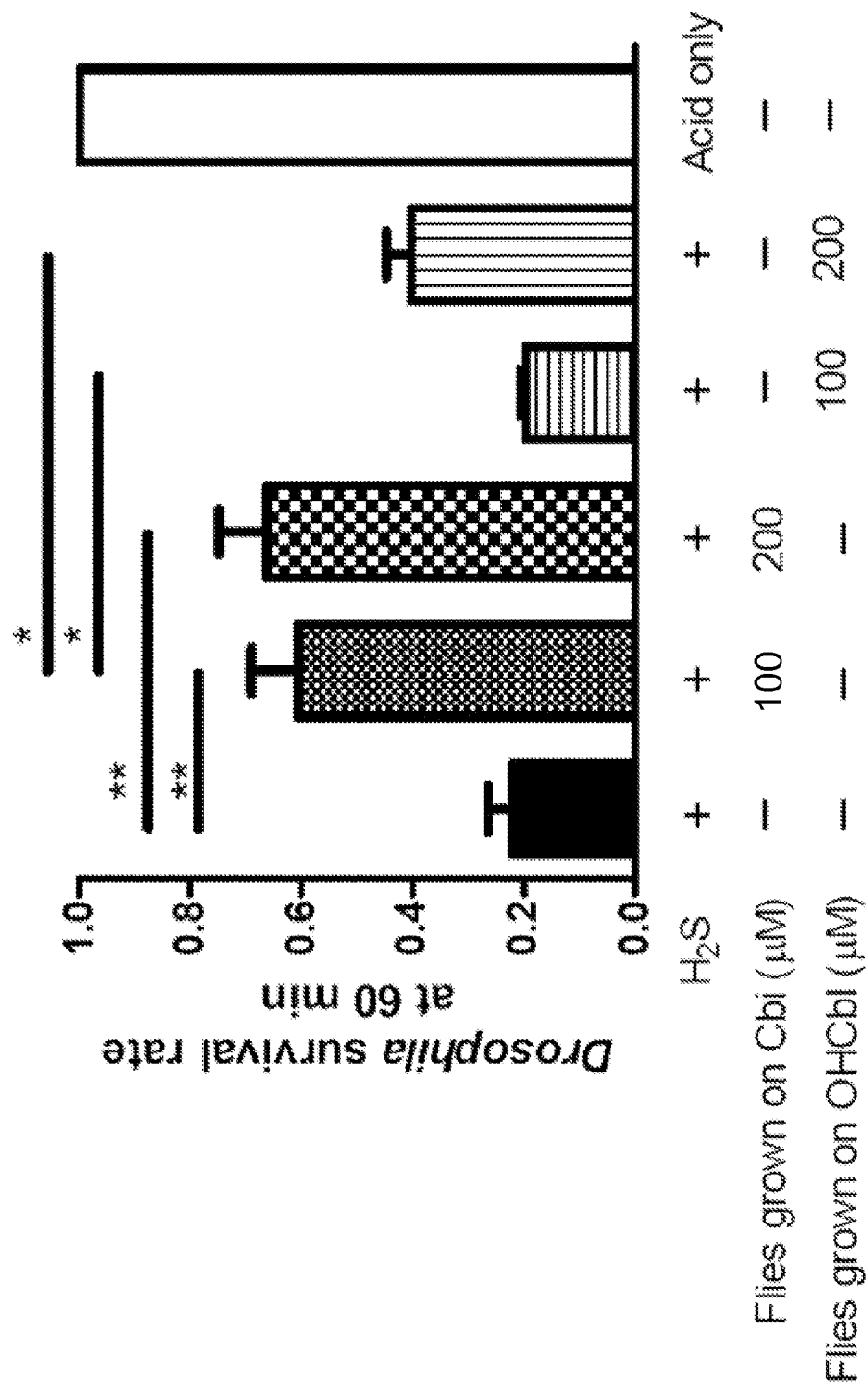
FIG. 22 illustrates fly survival rate at 60 minutes.
Figure 23:
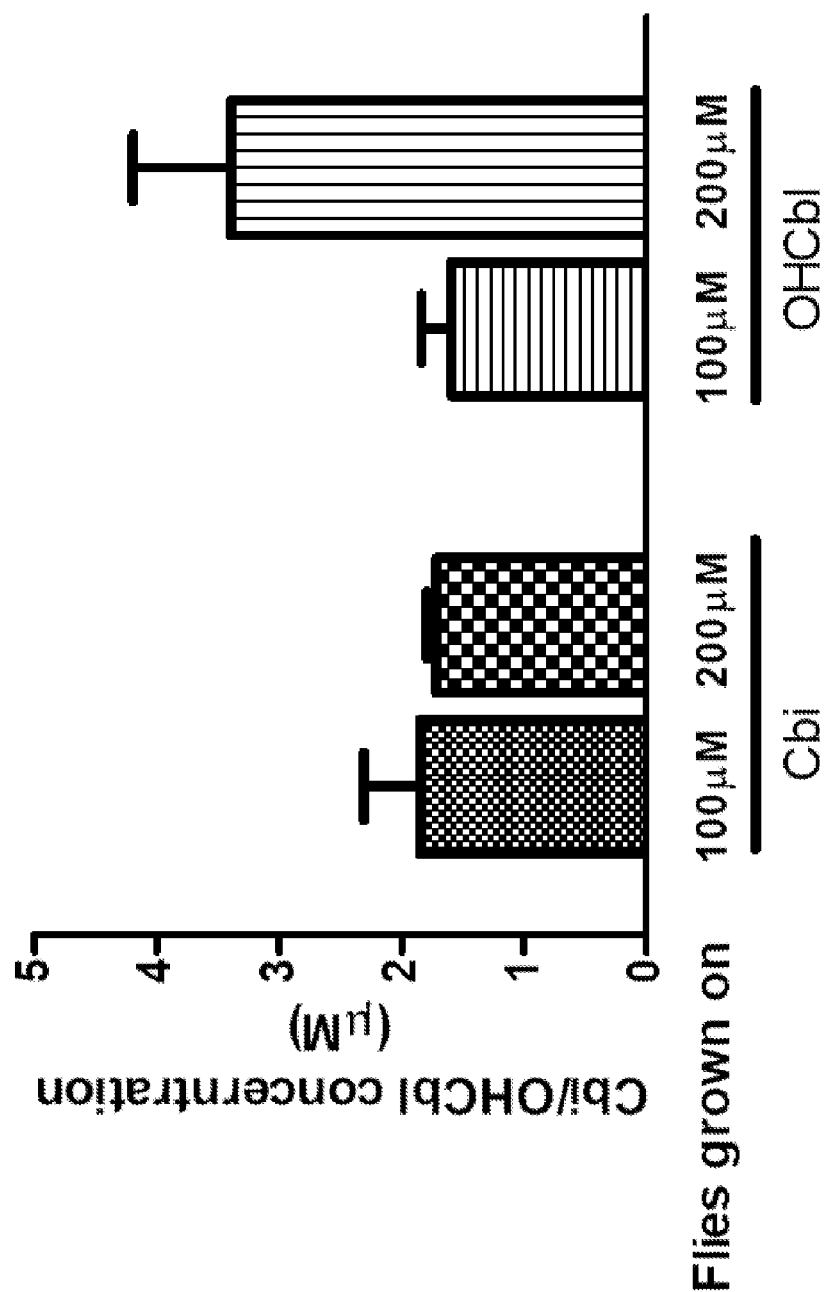
FIG. 23 illustrates the amount of cobinamide and hydroxocobalamin in flies.

FIGS. 21-23 illustrate an experiment with a 20 minute exposure to $H_2S$. Flies were exposed to $H_2S$ in then vials for 20 min before transferred to a $H_2S$ free vial. Recovery was checked every 15 min until 60 min. As shown in FIG. 21, about 40% of flies grown up on 200 μM cobinamide recover as early as 30 min post exposure, while less than 10% flies grown on 200 μM hydroxocobalamin recover at 30 min post exposure. FIG. 22 illustrates At 60 min post exposure, survival rate of 100 μM and 200 μM cobinamide fed flies are significantly higher than control flies and hydroxocobalamin fed flies. FIG. 23 illustrates the cobinamide and hydroxocobalamin content of the flies. 100 μM and 200 μM cobinamide fed flies contain similar cobinamide level, 1.85 μM and 1.72 respectively. 100 μM and 200 μM hydroxocobalamin fed flies contain 1.59 μM and 3.4 μM of hydroxocobalamin, respectively, indicating flies has taken similar amount of cobinamide and hydroxocobalamin and cobinamide is more potent in detoxifying hydrogen sulfide in flies.

Example 8

Cobinamide Rescue of Mice from Sulfide Gas Exposure

To simulate a mass casualty event an inhalational model was developed that allows mice to be exposed to sulfide gas, injected with an antidote, and then re-exposed to the gas. A chamber like that used for the cyanide experiments in Example 2 is used. Also, the 15-25 model described in Example 2 is also used. There were 5 mice in each group.

The mice are anesthetized fully throughout the sulfide exposure as required by Institutional Animal Care and Use Committee (IACUC): isofluorane is injected into the chamber to a final concentration of 2%, and due to its high volatility, it rapidly vaporizes and anesthetizes the mice.

Figure 24:
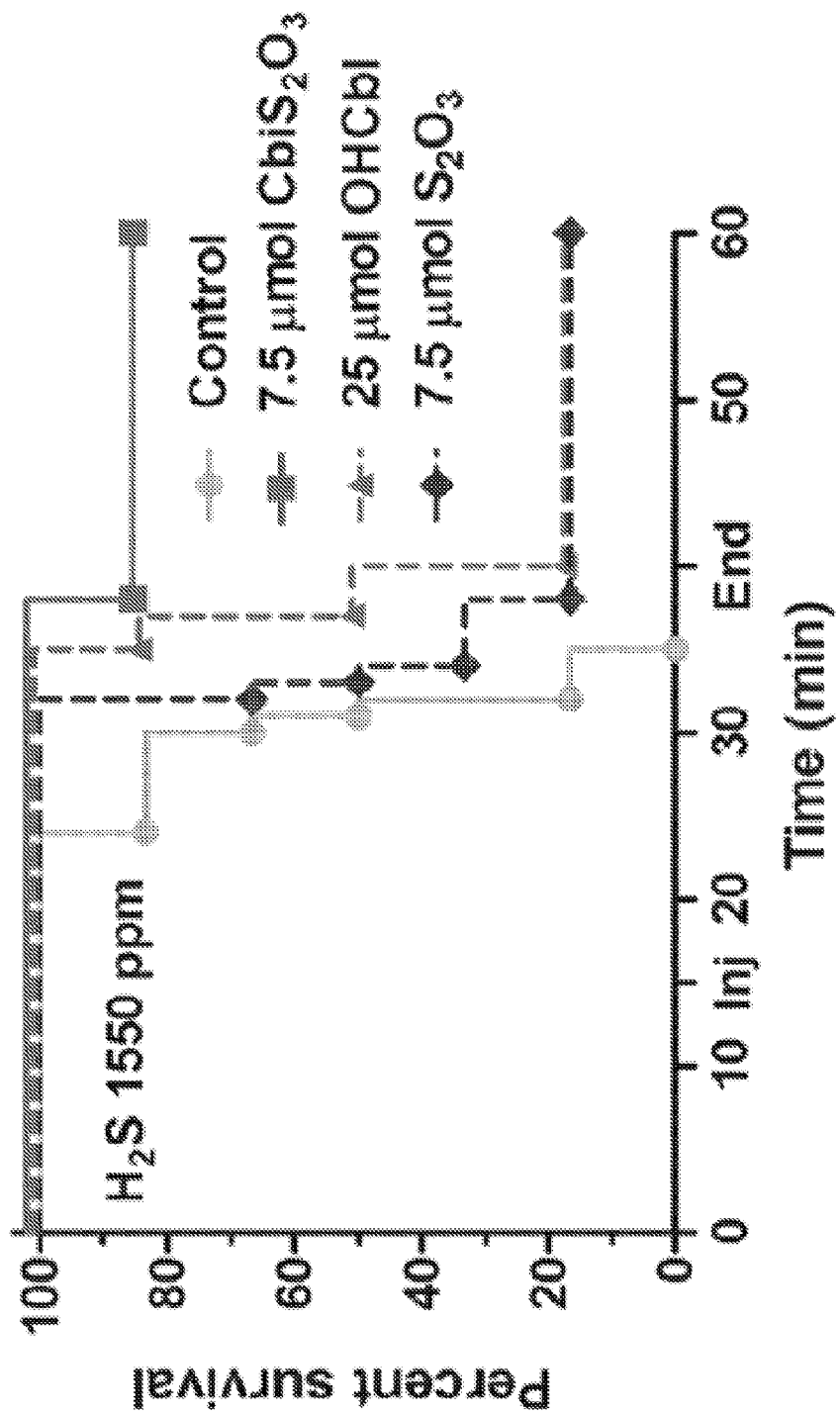
FIG. 24 illustrates cobinamide rescue of mice from sulfide gas exposure.

Control mice injected with saline all died between 25 and 35 min, i.e., starting 10 min into the second exposure period (FIG. 24). This is to be contrasted with an 80% survival rate in mice that received 7.5 μmol cobinamide (in aqueous solution such that cobalt in cobinamide is bound to a combination of water and hydroxide). The cobinamide was given by intraperitoneal injection to compare the results with cobinamide to those with hydroxocobalamin; the latter must be given in a relatively large volume (due to hydroxocobalamin's relatively low water solubility), and thus, it must be given by either intraperitoneal or intravenous injection. Cobinamide was given as the thiosulfate derivative because cobinamide thiosulfate is well absorbed after intraperitoneal injection. The equivalent thiosulfate dose had a small effect, yielding 20% survival. To observe an effect of hydroxocobalamin, 25 μmol had to be injected, and, even at that dose, achieved only 20% survival. Thus, at one-third the dose, cobinamide realized a four-fold greater survival rate than hydroxocobalamin, pointing to a large difference in potency between the two agents.

Figure 25:
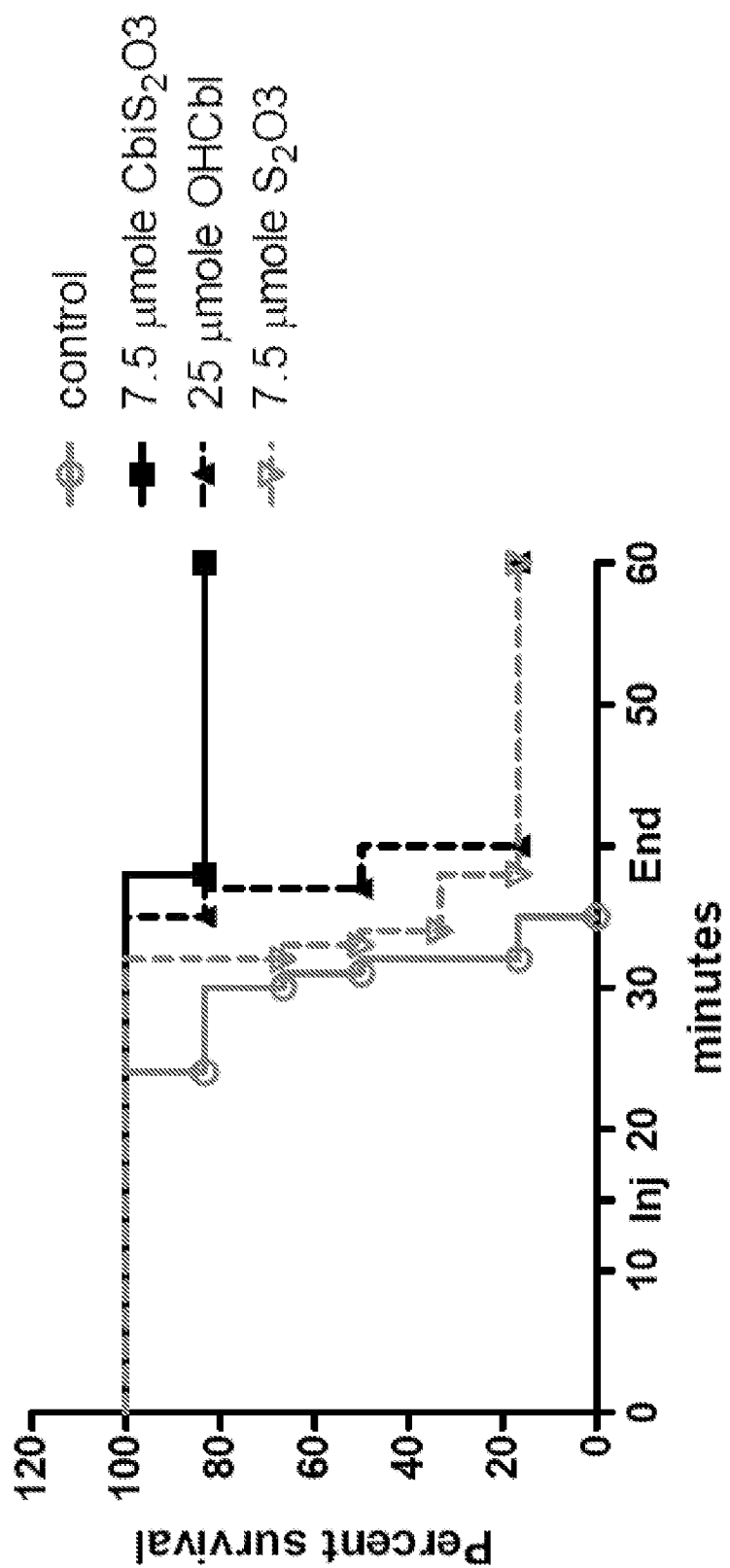
FIG. 25 illustrates results of an experiment where 2.67 ppt $H_2S$ was administered in the 15-25 model.

FIG. 25 illustrates results of an experiment where 2.67 ppt $H_2S$ was administered in the 15-25 model. Mice became apneic and die within 40 min. Intraperitoneal injection of 7.5 μmole $CbiS_2O_3$ increased the survival to 83% in hydrogen sulfide exposed mice. 25 μmole hydroxycobalamin treated mice only has a survival rate of 17%. 7.5 mole of sodium thiosulfate as $CbiS_2O_3$ control has a survival rate of 17% indicating that cobinamide contributes to the higher survival rate observed in $CbiS_2O_3$ treated mice. Total time observation was 60 min. with 6 mice per group.

Example 9

Cobinamide Rescue of Rabbits from Sulfide Poisoning

A rabbit model using diffuse optical spectroscopy (DOS) and continuous wave near infrared spectroscopy (CWNIRS) to noninvasively follow tissue oxy- and deoxy-hemoglobin concentrations and cytochrome C oxidase redox state in real time has been developed (Brenner, M., et al. *Ann. Emerg. Med.* 55:352-362(2009); Brenner, M., et al. *J. Biomed. Opt.* 15:017001 (2010); Brenner, M., et al. *J. Biomed. Opt.* 12:051701 (2007)). These novel spectroscopic methods are combined with standard hemodynamic monitoring and gas exchange analysis. Due to sulfide's inhibition of mitochondrial respiration, sulfide changes the oxygen saturation of hemoglobin circulating through tissues, and, due to sulfide-induced vasodilation, hypotension, and reflex tachycardia, sulfide affects cardiac output, blood pressure, and $CO_2$ production. All of these parameters are monitored in real time.

Figure 26:
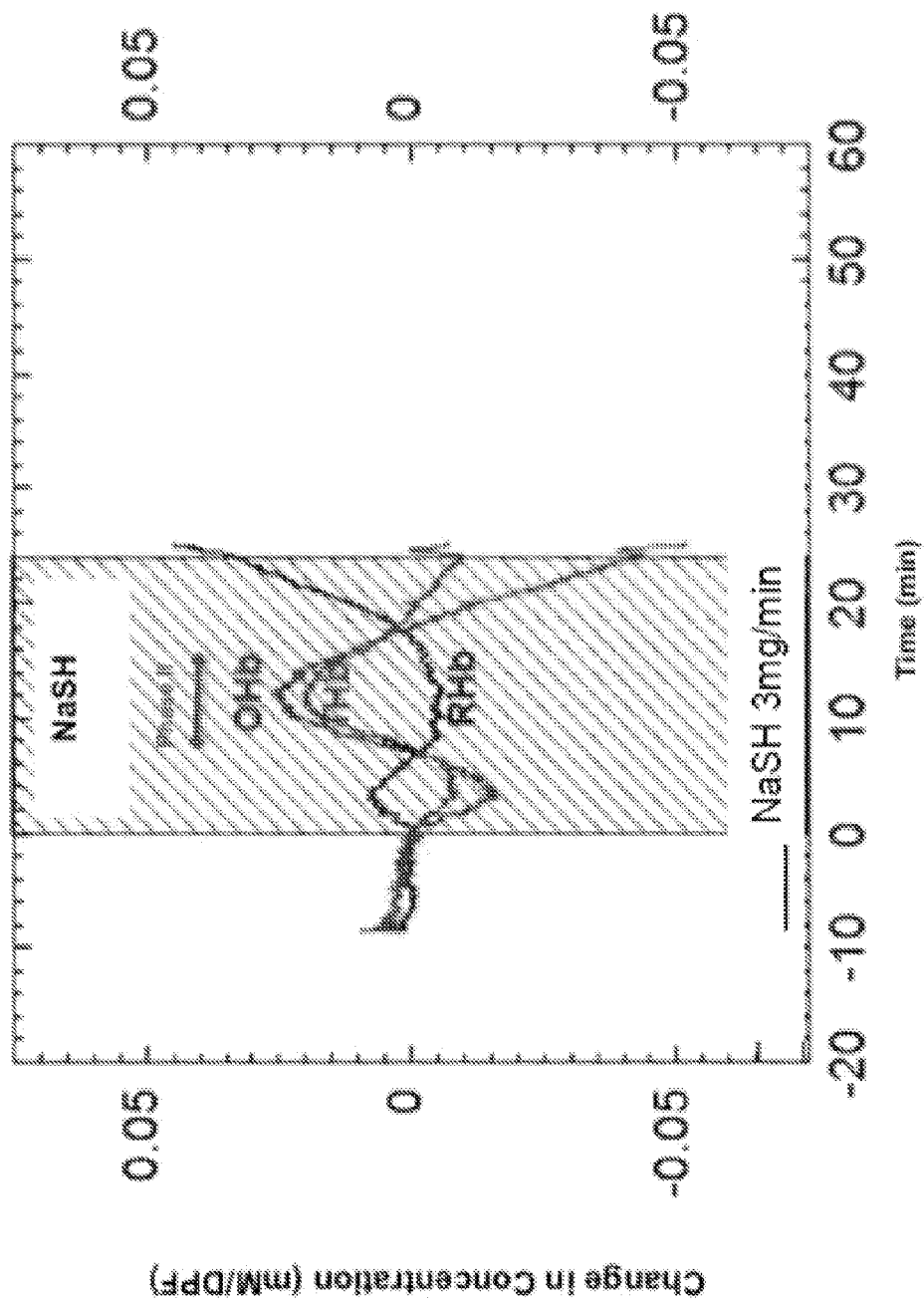
FIG. 26 illustrates the effects of sulfide on hemoglobin oxygenation.

A lethal model of sulfide poisoning has been developed using a continuous intravenous infusion of sodium hydrogen sulfide (NaSH) at 3 mg/min. The effects of sulfide on hemoglobin oxygenation are complex and tri-phasic over time (FIG. 26). Initially, tissue oxy-hemoglobin (OHb) decreases due to rapid sulfide-induced hypotension (Phase I; mean arterial blood pressure decreases by >30% during this time). A secondary reflex tachycardia increases tissue perfusion, and this, together with sulfide inhibition of cytochrome C oxidase and the resultant inability of tissues to extract oxygen from the blood, leads to increased tissue oxy-hemoglobin (Phase II). As sulfide poisoning progresses, cardiovascular collapse ensues, resulting in a precipitous fall in the oxy-hemoglobin concentration as the animal expires (Phase III; mean arterial blood pressure decreases by >70%). Opposite effects occur in the deoxy-hemoglobin (RHb) concentration.

In the above-described model, the hydrosulfide infusion is continued until the animals expire, or up to a maximum of 90 min of sulfide infusion when the animals are euthanized. For testing antidotes in the model, it was determined that the most appropriate time to give the antidote is as the animals move from Phase I (hypotension and decreased peripheral tissue oxygenation) into Phase II (tachycardia and reduced oxygen extraction with increased tissue oxy-hemoglobin). This shift occurred at an average of 13 min after start of the sulfide infusion (range 8-15 min), and hence this is a post-exposure model; moreover the sulfide infusion is continued after antidote injection. Thus, this is similar to the mouse model, and again simulates a real-life scenario of continued sulfide exposure, even after treatment.

In nine control animals that received an intravenous injection of 1 ml of saline, the average time until death was 31 min, with a range of 22-42 min (FIG. 26). In FIG. 26, tissue oxyhemoglobin (OHb, red line), deoxyhemoglobin (RHb, blue line), and total hemoglobin (THb, green line) were measured by diffuse optical spectroscopy, and are shown as a relative change in concentration. Sulfide infusion began at time zero, and continued for the time shown in the cross-hatched area. Initially, tissue oxy-hemoglobin (OHb) falls as animals become hypotensive (Phase I). Reflex tachycardia with increased perfusion, combined with inhibition of cytochrome C oxidase that leads to inability of tissues to extract oxygen from the circulating blood, increases tissue oxyhemoglobin (Phase II). As sulfide poisoning progresses, the animals develop terminal cardiovascular collapse with a precipitous drop in oxy-hemoglobin as they expire (Phase III). Equal and opposite effects are seen in deoxy-hemoglobin (RHb). In contrast, six of six animals treated with 25 mg/kg cobinamide (injected as 1 ml of a 100 mM solution) survived an average of 84 min of sulfide infusion, with five of the six animals surviving to the 90 min endpoint (p<0.0001 for difference between control and cobinamide-treated animals). Concordant with the marked survival improvement, cobinamide rapidly reversed the sulfide-induced changes in oxy- and deoxy-hemoglobin. In seven animals that received an identical hydroxocobalamin dose as the cobinamide dose, average survival time was 41 min, which was not statistically different from the control animals. Similarly, three animals that received 3.5 mg/kg sodium nitrite—on a molar basis this is twice as much nitrite as cobinamide and is similar to the nitrite dose used to treat cyanide poisoning—survived for only 37 min (again, not statistically different from controls, though the numbers are small). Thus, cobinamide rescued rabbits much more effectively from sulfide poisoning than hydroxocobalamin and sodium nitrite, similar to the results with hydroxocobalamin in mice.

Example 10

Intramuscular Administration of Cobinamide

Figure 27:
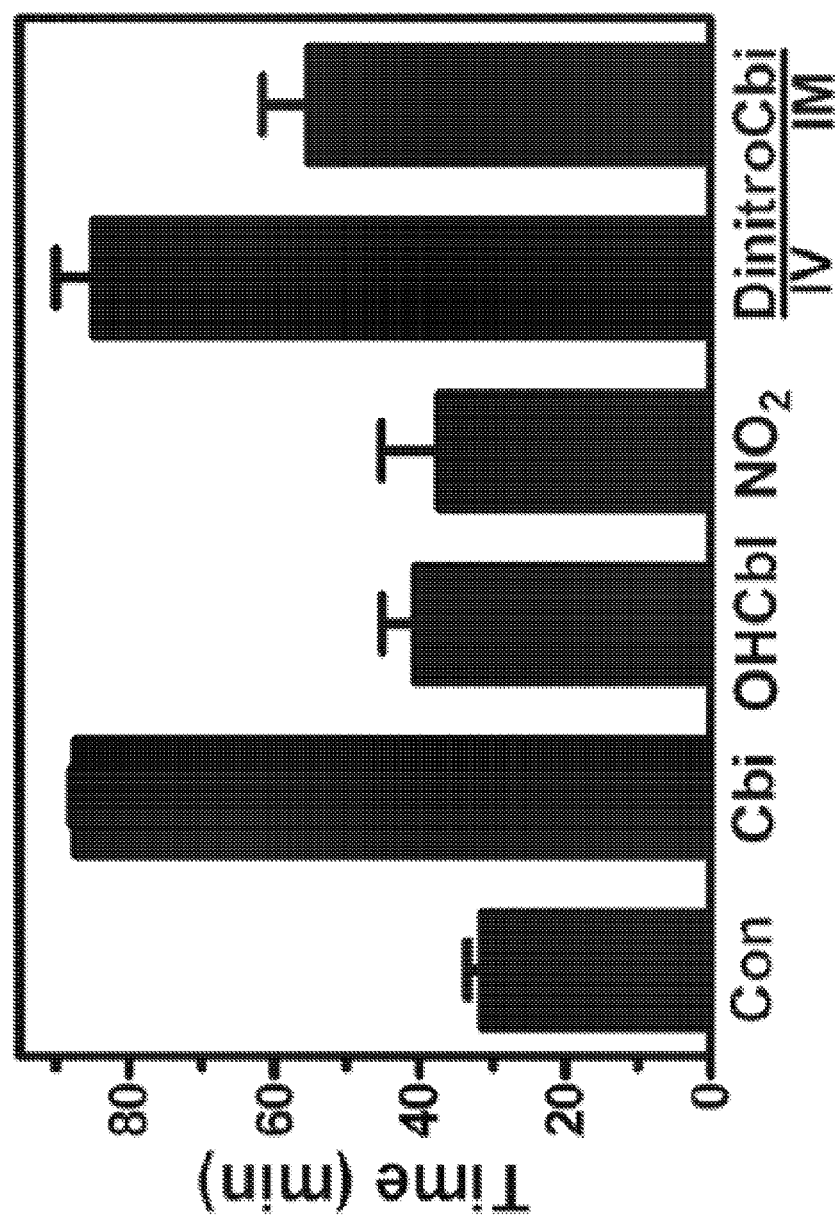
FIG. 27 illustrates survival time of sulfide-poisoned rabbits receiving intravenous sulfide.

Cobinamide derivatives that are absorbed after intramuscular injection include sulfitocobinamide and dinitrocobinamide. Sulfide reacts readily with dinitrocobinamide. Dinitrocobinamide was tested in the rabbit model, first by intravenous infusion, and it yielded similar results as aquo-hydroxocobinamide: the average survival time for three animals was 81 min, with two of the three completing the full 90 min infusion period (FIG. 27). This provided proof-of-principle of whether an intramuscular injection of an antidote could have an effect in sulfide poisoning. Of eight animals that received 25 mg/kg dinitrocobinamide by intramuscular injection, average survival time was 55 min, which was significantly better than control animals (p<0.05). Animals treated with intravenous sulfitocobinamide died at a mean dose of 170±8.8 mg SEM of NaHS (range 138-195 mg) (p<0.001 compared to controls), while animals treated with intramuscular sulfitocobinamide died at a mean dose of 133±4.4 mg SEM NaHS (P<001 compared to controls). While both delivery modes were effective against NaHS, IV administration resulted in a statistically significantly higher NaHS lethal dose compared to IM administration (p<0.01). Cobinamide can be effective against sulfide poisoning when given by intramuscular injection, with a cobinamide derivative that is absorbed more rapidly after intramuscular injection than dinitrocobinamide.

Due to the small size of mice (20-25 g), scaling to a human equivalent dose is less accurate than scaling from 4 kg rabbits. The 25 mg/kg cobinamide dose used in the rabbit experiments translate to 8.0 mg/kg for a human. For a 70 kg person, this could be given as 2.8 ml of a 200 mM solution.

Example 11

Cobinamide Stability and Safety

Aquohydroxoobinamide in aqueous solutions was kept for six months at room temperature and no degradation was found (in the pH range of 4.5-6.0). Based on accelerated degradation experiments, i.e., incubating cobinamide at temperatures as high as 60° C., it was determined that cobinamide should be stable at room temperature for at least two years. Thus, it could be packaged in pre-filled syringes. The sulfito- and dinitro-derivatives are even more stable than aquohydroxocobinamide.

Range-finding toxicity studies in mice and rats indicate cobinamide is safe to at least three four times the anticipated human dose. The dose limiting toxicity is acute transient coagulation abnormalities, and we have found that these effects are mitigated by having a ligand on the cobalt. Thus, sulfitocobinamide and dinitrocobinamide cause fewer coagulation defects and are considerably better tolerated by animals. Therefore, any new cobinamide derivative where the cobalt atom is occupied should also be well tolerated.

Example 12

Cobinamide to Treat Hydrogen Sulfide Exposure

New Zealand white rabbits and Yorkshire pigs can be used in testing. Rabbits are a good medium-sized animal that allow full hemodynamic monitoring and inhalational administration of drugs, and we used rabbits to develop excellent real-time optical monitoring of tissue oxygenation. The pigs are ~50 kg in size, approximating the size of a human; thus, minimal scaling of drug dose to human dose is needed. The cardiovascular system of pigs is very similar to that of humans, and the heart and peripheral vasculature are major sulfide targets (Hughes, H. C. Lab Anim Sci. 36:348-350 (1986)).

In experiments of screening new cobinamide derivatives for efficacy against sulfide, mice experiments will be done first using the previously-described 15/25 model, which simulates a real-life scenario of sulfide gas exposure.

Sulfide is a highly toxic chemical that must be used safely. To assure sulfide gas is not generated when making up NaSH solutions, NaSH is standardly dissolved in 1 mM NaOH (pH 11); thus, >99.99% of the NaSH will remain as NaSH and not be converted to sulfide gas ($H_2S$). The NaSH can be used either as is or diluted 100-fold and injected using a gas-tight syringe. All solutions are made in a chemical fume hood.

Example 13

Determine the Intravenous Cobinamide Dose that Rescues Rabbits and Pigs from Lethal Sulfide Poisoning In Example 9, animals were exposed to sulfide by continuous intravenous infusion and a rate of sulfide infusion that induced death at 31.3±6.2 min in control animals (mean±SD) was used. For cobinamide-treated animals, 90 min was set as the end of the sulfide infusion. People would be unlikely to be exposed to sulfide that long and thus this was an extremely rigorous test of cobinamide. Example 9 demonstrated that cobinamide was effective. Three standard deviations beyond the mean of the controls will now be used, which would mean that only 0.1% of control animals would be expected to live that long. This translates to 50 min, which is a more realistic exposure time to sulfide. Using this time of sulfide exposure, the cobinamide dose will be titrated down. As in Example 9, the cobinamide will be given by intravenous injection over 30 sec.

Similar experiments will be performed in pigs adapting a lethal cyanide model (Bebarta, V. S., et al. *Ann Emerg Med* 2012; 59:532-9; Bebarta, V. S., et al *Ann Emerg Med* 2010; 55:345-51; Bebarta, V. S., et al. *Ann. Emerg. Med.* 2012; 60:415-22) to sulfide, incorporating diffuse optical spectroscopy and continuous wave near infrared spectroscopy.

Animals will be intubated, anesthetized, and ventilated without supplemental oxygen support during the sulfide infusion. The experimental group will be administered cobinamide after optical-cardiovascular evidence of severe poisoning (development of Phase II physiologic changes described in Example 9). Survival is the primary endpoint. Secondary endpoints are quantitative stabilization of (i) oxy-, deoxy-hemoglobin, total hemoglobin, and oxidized and reduced cytochrome c oxidase as determined by diffuse optical spectroscopy and continuous wave near infrared spectroscopy over brain and muscle tissue, and (ii) respiratory exchange ratio determined by oxygen uptake and $CO_2$ elimination by inhaled and exhaled gas analysis. Blood pressure, blood chemistry, including changes in base excess and lactate levels, blood gas monitoring, and plasma cobinamide concentrations will be measured (the latter by HPLC using a well-developed assay). In addition, an optical microchip for noninvasively measuring lactate is being developed, with results validated against serum lactate. There will be 11 animals in each group, i.e., saline and cobinamide-treated groups, because this is the minimal number required to achieve statistical significance, assuming a standard deviation of 20% and at least a 50% difference between control and treated groups.

Example 14

Develop a Cobinamide Derivative that is Absorbed Rapidly after Intramuscular Injection and to Test its Efficacy Against Sulfide Cobinamide is very effective against sulfide when given by intravenous injection. However, as discussed above, an intramuscular method of administration is more flexible in mass casualty situations. Therefore other cobinamide derivatives will be generated by either adding a ligand or generating an organocobalt compound, i.e., a cobalt-carbon bond between cobinamide and an alkyl group. Derivatives will be tested first for their reaction with sulfide, then for their binding to skeletal muscle extracellular matrix, and finally for absorption and efficacy in mice. New cobinamide derivatives will be tested in the rabbit and pig models described above, but administered by intramuscular injection.

Generation of Cobinamide Derivatives. Ligands:

Most of the ligands that bind to cobinamide have either a nitrogen or sulfur group as the binding partner. The following series of candidates will be tested for binding to cobinamide, testing in the order listed to minimize potential toxicity of the released ligand: amino acids (through the amine group or the sulfur atom in the case of cysteine and methionine), glutathione and derivatives (through the amine or cysteine groups), purines and pyrimidines (through the nitrogen groups), imidazole derivatives (through one of the two nitrogen groups), and other sulfur- and nitrogen-containing compounds.

Organocobalt Complexes:

Organocobalt complexes will be generated by mixing cobinamide with an alkyl halide; halide groups are highly reactive allowing formation of the alkyl-cobinamide complex. (Hogenkamp, H. P. *Fed. Proc.* 25:1623-1627 (1966); Zagalak, B. *Acta Biochim. Pol.* 10:387-398(1963)). For the reaction to occur, cobinamide must first be reduced to the +1 valency state by, for example, zinc metal or sodium borohydride. (Hogenkamp, H. P., et al. *J. Biol. Chem.* 240:3641-

3644(1965); Barnett, R., et al. *J. Biol. Chem.* 241:1483-1486 (1966)) The resulting carbon-cobalt bond is relatively labile, and can be weakened further by placing an electron withdrawing group on the alkyl group. Thus, the carbon-cobalt bond of trimethylaminoethyl-cobinamide (bound via the ethyl group) is very labile—because of the electron withdrawing effect of the quaternary ammonium group—and sulfide can readily displace the alkyl group. Unfortunately, this compound is not well absorbed. Synthesis of cobinamide derivatives is relatively straightforward, and a series of them will be generated starting with formate and benzoic acid derivatives, because these should yield a labile carbon-cobalt bond due to the electron withdrawing properties of the complexed group. The active forms of vitamin B12/cobalamin are methyl-cobalamin and deoxyadenosyl-cobalamin, and the methyl and deoxadenosyl groups are easily removed during enzymatic reactions (Gaudemer, A., et al. *Eur. J. Biochem.* 119:279-285 (1981)). For both binding of ligands and generation of organocobalt compounds, formation of the derivative is confirmed by UV-vis spectral analyses, and the purity of the derivative is assessed by HPLC.

Reaction of Cobinamide Derivative with Sulfide:

As mentioned earlier, sulfide reduces cobinamide to the +2 valency state, and the final reaction product is cobinamide(II) with the bound anion-radical $SSH_2^-$. This cobinamide(II)-$SSH_2^-$ complex has a very distinctive spectrum, and thus we can readily determine if it has been formed. By testing a range of sulfide concentrations, sulfide's affinity for the derivative can be determined. Derivatives that have a relatively high sulfide affinity, i.e., $K_A > 10^8$, will be selected.

Binding of Cobinamide Derivative to Skeletal Muscle Extracellular Matrix:

Studies described in Example 4 will be performed. Specifically, we will incubate the cobinamide derivative with freshly prepared extracellular matrix from porcine skeletal muscle, and measure binding to the matrix. Only those derivatives that exhibit low matrix binding will be tested in mice.

Testing Cobinamide Derivatives in Mice:

The 15/25 sulfide gas inhalation model described in Example 8 will be used. To rescue animals, the cobinamide derivative must be absorbed rapidly and react rapidly with sulfide; thus this model will be a good means to assess the potential efficacy of the cobinamide derivatives against sulfide. Surviving animals will be observed closely for at least a week, providing a rough assessment of how well the animal tolerated the cobinamide derivative.

Example 15

Determine the Cobinamide Dose that Rescues Rabbits and Pigs from Lethal Sulfide Poisoning when Administered by Intraosseous Injection Cobinamide has been administered by intraosseous injection to both rabbits and pigs using the commercially available bone injection gun (BIG). The pharmacokinetics of cobinamide were almost identical to those obtained by intravenous injection.

The same pig and rabbit models of sulfide poisoning described in Example 13 will be used, but cobinamide will be administered by intraosseous injection instead of intravenous injection. Starting from opening the BIG package, the needle is inserted into the tibia and cobinamide injected in less than one minute. Thus, this route of administration could be used to treat a reasonably large number of sulfide-poisoned victims.

Example 16

Determine the Cobinamide Dose that Rescues Rabbits and Pigs from Lethal Sulfide Poisoning when Delivered by Inhalation Sulfide exposure almost always occurs through inhalation and the lungs are a major target of sulfide. Inhaling cobinamide could reduce sulfide's pulmonary toxicity by providing a high localized drug concentration that would neutralize sulfide before it could damage pneumocytes. Moreover, inhalational delivery is simple, does not involve needles, and patients can self-administer drugs. Absorption is very rapid, because the surface area of the lungs approximates that of a tennis court.

Figure 28:
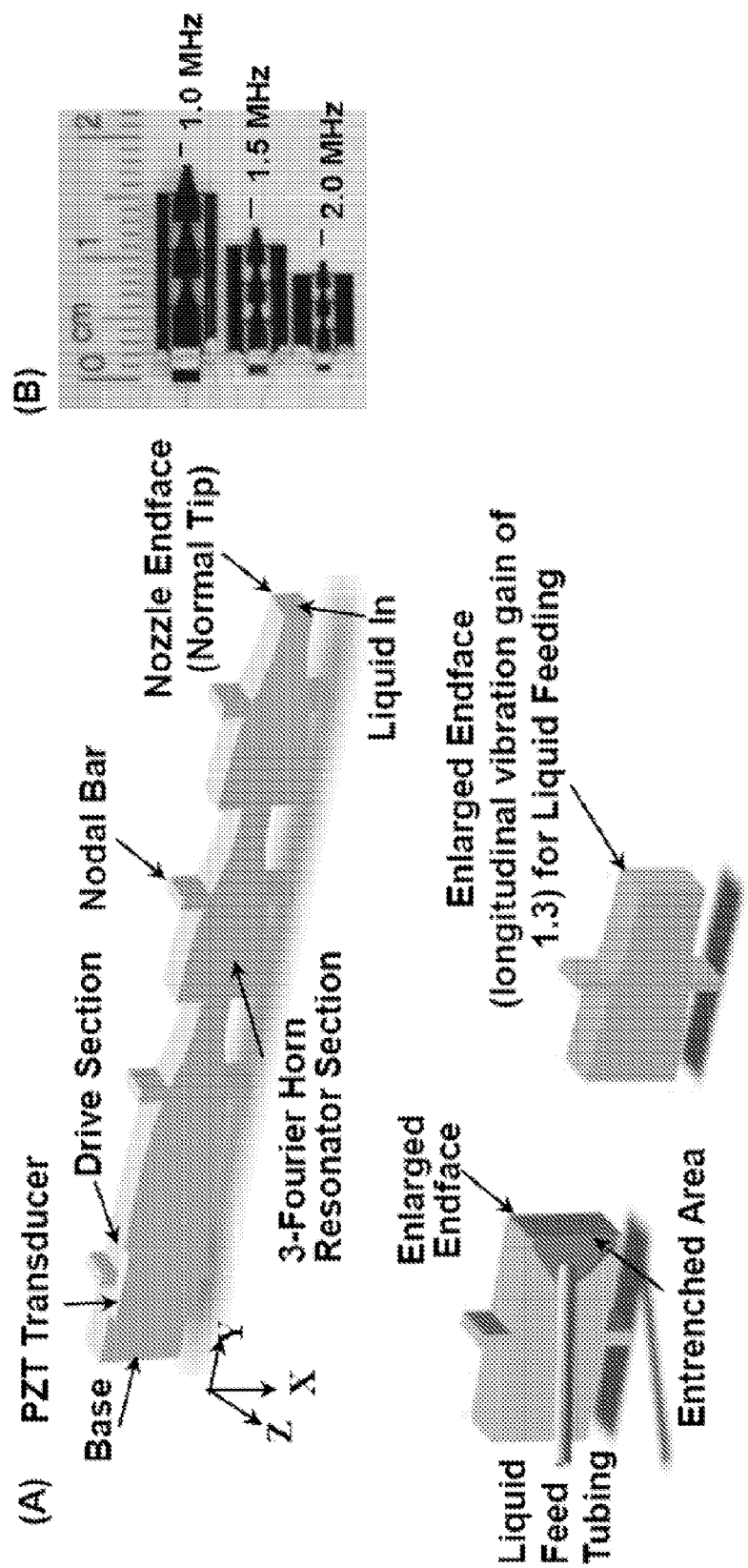
FIG. 28 illustrates a nebulizer for administering inhaled cobinamide according to one embodiment.

A novel ultrasonic nebulizer that can deliver several hundred milligrams of drug, as opposed to the microgram amounts delivered by current metered-dose inhalers is being developed. (Tsai, S. C., et al., *IEEE Trans. Ultrason. Ferroelectr. Freq. Control* 51:277-285 (2004); Tsai, S. C., et al., *Lab Chip.* 10:2733-2740 (2010); Tsai, S. C., et al., US Patent Publication No. US-2010-0327072; Tsai, S. C., et al., U.S. Pat. No. 6,669,103) The device comprises a silicon-based ultrasonic nozzle which consists of a twin-array of single-nozzles arranged in parallel (FIG. 28). Each single-nozzle consists of three Fourier horns in resonance with an enlarged endface, and employs external feeding of the liquid to be aerosolized. A single-nozzle nebulized a 150 mM cobinamide solution at 0.65 ml/min, and a twin-nozzle array device with enlarged endface should increase throughput to >1 ml/min, allowing 500 mg to 1 g of drug to be nebulized in less than 3 min. The whole device will be battery-powered and hand-held.

Cobinamide will be administered to rabbits and pigs using the nebulizer. It has been shown that the nebulizer delivers cobinamide rapidly to the alveoli, with minimal loss in the upper airways. The droplet size is quite uniform at 2.5-5 µm.

Pharmaceutical Compositions

The compounds employed in the methods of the present invention can be administered by any means that results in the contact of the active agents with the agents' site or site(s) of action in the body of a patient. The compounds can be administered by any conventional means available for use in conjunction with pharmaceuticals, either as individual therapeutic agents or in a combination of therapeutic agents. For example, they can be administered as the sole active agents in a pharmaceutical composition, or they can be used in combination with other therapeutically active ingredients.

The compounds are preferably combined with a pharmaceutical carrier selected on the basis of the chosen route of administration and standard pharmaceutical practice as described, for example, in the latest edition of Remington's Pharmaceutical Science, Mack Publishing Company, Easton, Pa. ("Remington's"), the disclosure of which is incorporated by reference in its entirety.

Compounds of the present invention can be administered to a mammalian host in a variety of forms adapted to the chosen route of administration, e.g., orally. Other acceptable routes of administration are parenteral including intravenous; intraosseous injection; intramuscular injection; subcutaneous injection; transepithelial including transdermal, transnasal, ophthalmic, sublingual and buccal; topical including ophthalmic, dermal, ocular, and rectal; nasal or pulmonary inhalation via insufflation or aerosol; and rectal systemic. Intramuscular injection is most typically performed in the arm, shoulder, or leg muscles.

The active compound can be orally administered, for example, with an inert diluent or with an assimilable edible carrier, it can be enclosed in hard or soft shell gelatin capsules, it can be compressed into tablets, or it can be incorporated directly with the food of the diet. For oral therapeutic administration, the active compound can be incorporated with excipient and used in the form of ingestible tablets, buccal tablets, troches, capsules, elixirs, suspensions, syrups, wafers, and the like. The amount of active compound(s) in such therapeutically useful compositions is from about 10 mg/day to about 1000 mg/day of active compound.

In certain aspects of the invention, cobinamide, or biologically active derivative or analog thereof, stereoisomer, prodrug, pharmaceutically acceptable salt, hydrate, solvate, acid salt hydrate, N-oxide or isomorphic crystalline form thereof is administered at a level of at least about 10 mg/day, more preferably at a level of at least about 100 mg/day, even more preferably at a level of at least about 500 mg/day, and yet even more preferably at a level of at least about 1000 mg/day.

In certain aspects of the invention, cobinamide, or biologically active derivative or analog thereof, stereoisomer, prodrug, pharmaceutically acceptable salt, hydrate, solvate, acid salt hydrate, N-oxide or isomorphic crystalline form thereof is administered at a level of at a level of less than about 100 mg/day, more preferably at a level of less than about 500 mg/day, even more preferably at a level of less than about 1000 mg/day, and yet even more preferably at a level of less than about 2000 mg/day.

In accordance with the methods of the present invention, the cobinamide compounds can be administered to a patient in a dosage range of from about 1 mg/day to about 1000 mg/day (and all combinations and subcombinations of dosage ranges and specific dosages therein).

The tablets, troches, pills, capsules and the like can also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound can be incorporated into sustained-release preparations and formulations.

The compound(s) of the invention, or a biologically active derivative(s) or analog(s) thereof can also be administered in sustained delivery or sustained release mechanisms, which can deliver the formulation internally. For example, biodegradeable microspheres or capsules or other biodegradeable polymer configurations capable of sustained delivery of a peptide can be included in the formulations of the invention. (See, e.g., Putney, *Nat. Biotechnol.* 16: 153-157, 1998).

The active compound can also be administered parenterally. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols and mixtures thereof and in oils. Under ordinary conditions of storage and use, these preparations can contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms can be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be achieved by the use of agents delaying absorption, for example, aluminum monostearate and gelatin.

Sterile injectable solutions can be prepared by incorporating the active compounds in the required amounts, in the appropriate solvent, with various of the other ingredients enumerated above, as required, followed by filtered sterilization. Generally, dispersions can be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation can include vacuum drying and the freeze-drying technique that yield a powder of the active ingredient, plus any additional desired ingredient from the previously sterile-filtered solution thereof.

The therapeutic compounds of this invention can be administered to a patient alone or in combination with a pharmaceutically acceptable carrier. As noted above, the relative proportions of active ingredient and carrier can be determined, for example, by the solubility and chemical nature of the compounds, chosen route of administration and standard pharmaceutical practice.

Systemic administration can also be by transmucosal or transdermal means. For transmucosal or transdermal administration, penetrants appropriate to the barrier to be permeated can be used in the formulation. Such penetrants are generally known in the art, and include, e.g., for transmucosal administration, bile salts and fusidic acid derivatives. In addition, detergents can be used to facilitate permeation. Transmucosal administration can be through nasal sprays or using suppositories. (See, e.g., Sayani, *Crit. Rev. Ther. Drug Carrier Syst.* 13: 85-184, 1996.) For topical, transdermal administration, the agents are formulated into ointments, creams, salves, powders and gels. Transdermal delivery systems can also include, e.g., patches.

For inhalation, the compounds of the invention can be delivered using any system known in the art, including dry powder aerosols, liquid delivery systems, air jet nebulizers, propellant systems, and the like. See, e.g., Patton, *Biotechniques* 16: 141-143, 1998; product and inhalation delivery systems for polypeptide macromolecules by, e.g., Dura Pharmaceuticals (San Diego, Calif.), Aradigm (Hayward, Calif.), Aerogen (Santa Clara, Calif.), Inhale Therapeutic Systems (San Carlos, Calif.), and the like. For example, the pharmaceutical formulation can be administered in the form of an aerosol or mist. For aerosol administration, the formulation can be supplied in finely divided form along with a surfactant and propellant. In another aspect, the device for delivering the formulation to respiratory tissue is an inhaler in which the formulation vaporizes. Other liquid delivery systems include, e.g., air jet nebulizers.

In preparing pharmaceuticals of the present invention, a variety of formulation modifications can be used and manipulated to alter pharmacokinetics and biodistribution. A number of methods for altering pharmacokinetics and biodistribution are known to one of ordinary skill in the art. Examples of such methods include protection of the compositions of the invention in vesicles composed of substances such as proteins, lipids (for example, liposomes, see below), carbohydrates, or synthetic polymers (discussed above). For a general discussion of pharmacokinetics, see, e.g., Remington's.

The pharmaceutical compositions are generally formulated as sterile, substantially isotonic, and in full compliance with all Good Manufacturing Practice (GMP) regulations of the U.S. Food and Drug Administration.

The pharmaceutical compositions of the invention can be administered in a variety of unit dosage forms depending upon the method of administration. Dosages are well known to those of skill in the art. Such dosages are typically advisory in nature and are adjusted depending on the particular therapeutic context, patient tolerance, and the like. The amount of a compound of the invention adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age, pharmaceutical formulation and concentration of active agent, and the like. In calculating the dosage regimen for a patient, the mode of administration also is taken into consideration. The dosage regimen must also take into consideration the pharmacokinetics, i.e., the pharmaceutical composition's rate of absorption, bioavailability, metabolism, clearance, and the like. See, e.g., the latest Remington's; Egleton, *Peptides* 18: 1431-1439, 1997; Langer Science 249: 1527-1533, 1990.

In some embodiments, cobinamide is administered at a dose of 1 to 500 mg. In other methods, the cobinamide is administered at a dose of 100 mg to 1 g. In some methods, the cobinamide is administered at a dose of 500 mg to 5 g. In some embodiments, the cobinamide is administered at a dosage of 2 mg/kg to 25 mg/kg, 2 mg/kg to 17 mg/kg, 2 mg/kg to 15 mg/kg or 15 mg/kg to 17 mg/kg. When dinitrocobinamide is used in a solution with 2 molar equivalents of nitrite (in addition to the nitrites bound to the cobinamide), a lower dose may be used.

In therapeutic applications, compositions are administered to a patient suffering from a disease state caused or exacerbated by the presence of excess hydrogen sulfide or excess cyanide to at least partially arrest the condition or a disease and/or its complications. For example, in one aspect, a soluble pharmaceutical composition dosage for intravenous (IV) administration would be about 10 mg/hr to about 500 mg/hr administered over several hours (typically 1, 3, or 6 hours), which can be repeated for weeks with intermittent cycles. Considerably higher dosages (e.g., ranging up to about 1000 mg/hr) can be used, particularly when the drug is administered to a secluded site and not into the blood stream, such as into a body cavity or into a lumen of an organ, e.g., the cerebrospinal fluid (CSF) or a joint space or structure.

The invention provides pharmaceutical compositions comprising one or a combination of compounds, such as cobinamide and cobalamin, formulated together with a pharmaceutically acceptable carrier.

In prophylactic applications, pharmaceutical compositions or medicaments are administered to a patient susceptible to, or otherwise at risk of a disease or condition (e.g., caused by excess hydrogen sulfide, sepsis, chronic liver failure, cirrhosis, hepatic encephalopathy, hepatorenal syndrome, hepatopulmonary syndrome, cirrhotic cardiomyopathy, hemodialysis-related hypotension, cardiogenic shock, ischemia-reperfusion injury, hypoxia, trauma cyanide toxicity, caused by excess cyanide, the patient is a cigarette smoker, hemodialysis, cystic fibrosis, nitroprusside, or excess cyanide brought about by weapons of mass destruction) in an amount sufficient to eliminate or reduce the risk, lessen the severity, or delay the onset of the disease, including biochemical, histologic and/or behavioral symptoms of the disease, its complications, and intermediate pathological manifestations presenting during development of the disease. In therapeutic applications, compositions or medicants are administered to a patient suspected of, or already suffering from such a disease in an amount sufficient to cure, or at least partially arrest, the symptoms of the disease (biochemical, histologic, and/or behavioral), including its complications and intermediate pathological manifestations in development of the disease. An amount adequate to accomplish therapeutic or prophylactic treatment is defined as a therapeutically- or prophylactically-effective dose. In both prophylactic and therapeutic regimes, agents are usually administered in several dosages until a sufficient response has been achieved. Typically, any response is monitored and repeated dosages are given if the response starts to wane.

The dosage of the compounds of the present invention that will be most suitable for prophylaxis or treatment will vary with the form of administration, the particular compound chosen and the physiological characteristics of the particular patient under treatment. Generally, small dosages can be used initially and, if necessary, increased by small increments until the desired effect under the circumstances is reached. Generally speaking, oral administration can require higher dosages.

The combination products useful in the methods of this invention, such as pharmaceutical compositions comprising cobinamide, or a biologically active derivatives or analogs thereof, with additional active ingredients (e.g., cobalamin) can be in any dosage form, such as those described herein, and can also be administered in various ways, as described herein. In a preferred embodiment, the combination products of the invention are formulated together, in a single dosage form (that is, combined together in one capsule, tablet, powder, or liquid, and the like). When the combination products are not formulated together in a single dosage form, the cobinamide, or a biologically active derivatives or analogs thereof, and additional active ingredient (e.g., cobalamin) can be administered at the same time or simultaneously (that is, together), or in any order.

A pre-filled syringe or autoinjector-syringe is useful for mass casualty events. As described in Example 11, it was determined that cobinamide should be stable for at least 2 years and certain forms of cobinamide, namely sulfite- and dinitrocobinamide are more stable than aquohydroxocobinamide.

Decellularized skeletal muscle ECM can be used as an in vitro model for interactions between a drug and ECM. The nature of the interaction can be elucidated using compounds that alter binding, and our data indicate that cobinamide is binding to the ECM via the cobalt ion. improved formulation of drugs intended for IM injection.

REFERENCES

Reiffenstein, R. J., Hulbert, W. C., and Roth, S. H. 1992. Toxicology of hydrogen sulfide. *Annu. Rev. Pharmacol. Toxicol.* 32:109-134.

Smith, R. P., and Gosselin, R. E. 1979. Hydrogen sulfide poisoning. *J. Occup. Med.* 21:93-97.

Maebashi, K., Iwadate, K., Sakai, K., Takatsu, A., Fukui, K., Aoyagi, M., Ochiai, E., and Nagai, T. 2010. Toxicological analysis of 17 autopsy cases of hydrogen sulfide poisoning resulting from the inhalation of intentionally generated hydrogen sulfide gas. *Forensic Sci. Int.*

Sams, R. N., Carver, H. W., Catanese, C., and Gilson, T. 2013. Suicide with hydrogen sulfide. *Am. J. Forensic Med. Pathol.* 34:81-82.

Reedy, S. J., Schwartz, M. D., and Morgan, B. W. 2011. Suicide fads: frequency and characteristics of hydrogen sulfide suicides in the United States. *West J. Emerg. Med.* 12:300-304.

Kamijo, Y., Takai, M., Fujita, Y., Hirose, Y., Iwasaki, Y., and Ishihara, S. 2013. A multicenter retrospective survey on a suicide trend using hydrogen sulfide in Japan. *Clin. Toxicol. (Phila)* 51:425-428.

Hydrogen Sulfide. Agency for Toxic Substances and Disease Registry. Center for Disease Control. http://www.atsdr.cdc.gov/substances/toxsubstance.asp?toxid=67

Cooper, C. E., and Brown, G. C. 2008. The inhibition of mitochondrial cytochrome oxidase by the gases carbon monoxide, nitric oxide, hydrogen cyanide and hydrogen sulfide: chemical mechanism and physiological significance. *J. Bioenerg. Biomembr.* 40:533-539.

Sun, Y., Tang, C. S., DU, J. B., and Jin, H. F. 2011. Hydrogen sulfide and vascular relaxation. *Chin Med. J. (Engl.)* 124:3816-3819.

Shibuya, N., Mikami, Y., Kimura, Y., Nagahara, N., and Kimura, H. 2009. Vascular endothelium expresses 3-mercaptopyruvate sulfurtransferase and produces hydrogen sulfide. *J. Biochem.* 146:623-626.

Yong, Q. C., Pan, T. T., Hu, L. F., and Bian, J. S. 2008. Negative regulation of beta-adrenergic function by hydrogen sulphide in the rat hearts. *J. Mol. Cell Cardiol.* 44:701-710.

Toohey, J. I. 1993. Hydrosulfide derivatives of Cobalamins. *J. Inorg. Biochem.* 49:189-199.

Guidotti, T. L. 1996. Hydrogen sulphide. *Occup. Med. (Lond)* 46:367-371.

Truong, D. H., Mihajlovic, A., Gunness, P., Hindmarsh, W., and O'Brien, P. J. 2007. Prevention of hydrogen sulfide (H2S)-induced mouse lethality and cytotoxicity by hydroxocobalamin (vitamin B(12a)). *Toxicology* 242:16-22.

Smith, R. P. 1969. Cobalt salts: effects in cyanide and sulfide poisoning and on methemoglobinemia. *Toxicol. Appl. Pharmacol.* 15:505-516.

Smith, R. P., Kruszyna, R., and Kruszyna, H. 1976. Management of acute sulfide poisoning. Effects of oxygen, thiosulfate, and nitrite. *Arch. Environ. Health* 31:166-169.

Fujita, Y., Fujino, Y., Onodera, M., Kikuchi, S., Kikkawa, T., Inoue, Y., Niitsu, H., Takahashi, K., and Endo, S. 2011. A fatal case of acute hydrogen sulfide poisoning caused by hydrogen sulfide: hydroxocobalamin therapy for acute hydrogen sulfide poisoning. *J. Anal. Toxicol.* 35:119-123.

Hall, A. H., and Rumack, B. H. 1997. Hydrogen sulfide poisoning: an antidotal role for sodium nitrite? *Vet. Hum. Toxicol.* 39:152-154.

Hoidal, C. R., Hall, A. H., Robinson, M. D., Kulig, K., and Rumack, B. H. 1986. Hydrogen sulfide poisoning from toxic inhalations of roofing asphalt fumes. *Ann. Emerg. Med.* 15:826-830.

Stine, R. J., Slosberg, B., and Beacham, B. E. 1976. Hydrogen sulfide intoxication. A case report and discussion of treatment. *Ann. Intern. Med.* 85:756-758.

Van de, L. A., and Haouzi, P. 2013. Ferric Iron and Cobalt (III) compounds to safely decrease hydrogen sulfide in the body? *Antioxid. Redox. Signal.* 19:510-516.

Hayward, G. C., Hill, H. A. O., Pratt, J. M., Vanston, N. J., and Williams, A. R. W. 1965. The chemistry of vitamin B(12). Part IV.1 The thermodynamic trans-effect. *J. Chem. Soc.* 6485-6493.

Sharma, V. S., Pilz, R. B., Boss, G. B., and Magde, D. 2003. Reactions of nitric oxide with vitamin B12 and its precursor, cobinamide. *Biochemistry* 42:8900-8908.

Broderick, K. E., Singh, V., Zhuang, S., Kambo, A., Chen, J. C., Sharma, V. S., Pilz, R. B., and Boss, G. R. 2005. Nitric oxide scavenging by the cobalamin precursor cobinamide. *J. Biol. Chem.* 280:8678-8685.

Broderick, K. E., Potluri, P., Zhuang, S., Scheffler, I. E., Sharma, V. S., Pilz, R. B., and Boss, G. R. 2006. Cyanide detoxification by the cobalamin precursor cobinamide. *Exp. Biol. Med.* 231:641-651.

Chan, A., Balasubramanian, M., Blackledge, W., Mohammad, O. M., Alvarez, L., Boss, G. R., and Bigby, T. D. 2010. Cobinamide is superior to other treatments in a mouse model of cyanide poisoning. *Clin. Toxicol. (Phila)* 48:709-717.

Brenner, M., Kim, J. G., Mahon, S. B., Lee, J., Kreuter, K. A., Blackledge, W., Mukai, D., Patterson, S., Mohammad, O., Sharma, V. S. et al 2009. Intramuscular Cobinamide Sulfite in a Rabbit Model of Sublethal Cyanide Toxicity. *Ann. Emerg. Med.* 55:352-362.

Brenner, M., Mahon, S. B., Lee, J., Kim, J., Mukai, D., Goodman, S., Kreuter, K. A., Ahdout, R., Mohammad, O., Sharma, V. S. et al 2010. Comparison of cobinamide to hydroxocobalamin in reversing cyanide physiologic effects in rabbits using diffuse optical spectroscopy monitoring. *J. Biomed. Opt.* 15:017001.

Tickoo, S., and Russell, S. 2002. *Drosophila melanogaster* as a model system for drug discovery and pathway screening. *Curr. Opin. Pharmacol.* 2:555-560.

Brenner, M., Kreuter, K., Mukai, D., Burney, T., Guo, S., Su, J., Mahon, S., Tran, A., Tseng, L., Ju, J. et al 2007. Detection of acute smoke-induced airway injury in a New Zealand white rabbit model using optical coherence tomography. *J. Biomed. Opt.* 12:051701.

DeQuach, J. A., Mezzano, V., Miglani, A., Lange, S., Keller, G. M., Sheikh, F., and Christman, K. L. 2010. Simple and high yielding method for preparing tissue specific extracellular matrix coatings for cell culture. *PLoS. ONE.* 5:e13039.

Bebarta, V. S., Pitotti, R. L., Dixon, P., Lairet, J. R., Bush, A., and Tanen, D. A. 2012. Hydroxocobalamin versus sodium thiosulfate for the treatment of acute cyanide toxicity in a swine (*Sus scrofa*) model. *Ann. Emerg. Med.* 59:532-539.

Bebarta, V. S., Tanen, D. A., Lairet, J., Dixon, P. S., Valtier, S., and Bush, A. 2010. Hydroxocobalamin and sodium thiosulfate versus sodium nitrite and sodium thiosulfate in the treatment of acute cyanide toxicity in a swine (*Sus scrofa*) model. *Ann. Emerg. Med.* 55:345-351.

Bebarta, V. S., Pitotti, R. L., Dixon, P. S., Valtier, S., Esquivel, L., Bush, A., and Little, C. M. 2012. Hydroxocobalamin and epinephrine both improve survival in a swine model of cyanide-induced cardiac arrest. *Ann. Emerg. Med.* 60:415-422.

Hughes, H. C. 1986. Swine in cardiovascular research. *Lab Anim Sci.* 36:348-350.

Hogenkamp, H. P. 1966. Recent development in the chemistry of B12 coenzymes. *Fed. Proc.* 25:1623-1627.

Zagalak, B. 1963. Chemical Synthesis Of Aliphatic Analogues Of Cobinamide Coenzyme And Their Effect On Enzymic Activity. *Acta Biochim. Pol.* 10:387-398.

Hogenkamp, H. P., Rush, J. E., and Swenson, C. A. 1965. Observations on the organometallic bond of the corrinoid coenzymes. *J. Biol. Chem.* 240:3641-3644.

Barnett, R., Hogenkamp, H. P., and Abeles, R. H. 1966. Reactions of the carbon-cobalt bond of alkylcobalamins. A reversible dissociation of the carbon-cobalt bond. *J. Biol. Chem.* 241:1483-1486.

Gaudemer, A., Zylber, J., Zylber, N., Baran-Marszac, M., Hull, W. E., Fountoulakis, M., Konig, A., Wolfle, K., and Retey, J. 1981. Reversible cleavage of the cobalt-carbon bond to coenzyme B12 catalysed by methylmalonyl-CoA mutase from *Propionibacterium shermanii*. The use of coenzyme B12 stereospecifically deuterated in position 5'. *Eur. J. Biochem.* 119:279-285.

Tsai, S. C., Song, Y. L., Tseng, T. K., Chou, Y. F., Chen, W. J., and Tsai, C. S. 2004. High-frequency, silicon-based ultrasonic nozzles using multiple Fourier horns. *IEEE Trans*. Ultrason. Ferroelectr. Freq. Control 51:277-285.

Tsai, C. S., Mao, R. W., Lin, S. K., Wang, N., and Tsai, S. C. 2010. Miniaturized multiple Fourier-horn ultrasonic droplet generators for biomedical applications. *Lab Chip.* 10:2733-2740.

Tsai, C. S., and Tsai, S. C. 2010. Method for transportating a liquid for atomization and a method and devices for atomizing the same. US Patent Publication No. US-2010-0327072.

Tsai, S. C. 2003. Multiple-Horn Atomizer with High Frequency Capability. U.S. Pat. No. 6,669,103 B2

Thompson J P, Marrs T C. Hydroxocobalamin in cyanide poisoning. Clin Toxicol (Phila) 2012; 50:875-85.

Borron S W, Baud F J, Barriot P, Imbert M, Bismuth C. Prospective study of hydroxocobalamin for acute cyanide poisoning in smoke inhalation. Ann Emerg Med 2007; 49:794-801.

Jett D A, Yeung D T. The Counter ACT Research Network: basic mechanisms and practical applications. Proc Am Thorac Soc 2010; 7:254-6.

Countermeasures Against Chemical Threats (CounterACT) Exploratory/Developmental Projects in Translational Research (R21). National Institutes of Health (NIH), 2013. (Accessed 2013, at http://grants.nih.gov/grants/guide/pa-files/PAR-13-005.html.)

Djuric V, Bogic M, Popadic A P, Spiric V T, Raskovic S. Anaphylactic reaction to hydroxycobalamin with tolerance to cyanocobalamin. Ann Allergy Asthma Immunol 2012; 108:207-8.

Vidal C, Lorenzo A. Anaphylactoid reaction to hydroxycobalamin with tolerance of cyanocobalamin. Postgrad Med J 1998; 74:702.

Borron S W, Stonerook, M., Reid, F. Efficacy of hydroxocobalamin for the treatment of acute cyanide poisoning in adult beagle dogs. Clin Toxicol (Phila) 2006; 44 Suppl 1:5-15.

Hughes C, Lehner F, Dirikolu L, et al. A Simple and Highly Sensitive Spectrophotometric Method for the Determination of Cyanide in Equine Blood. Toxicology Mechanisms and Methods 2003; 13:129-38.

Schwertner H A, Valtier S, Bebarta V S. Liquid chromatographic mass spectrometric (LC/MS/MS) determination of plasma hydroxocobalamin and cyanocobalamin concentrations after hydroxocobalamin antidote treatment for cyanide poisoning. J Chromatogr B Analyt Technol Biomed Life Sci 2012; 905:10-6.

Chan A, Balasubramanian M, Blackledge W, et al. Cobinamide is superior to other treatments in a mouse model of cyanide poisoning. Clin Toxicol (Phila) 2010; 48:709-17.

Uhl, W, Nolting A, Golor G, Rost K L, Kovar A. Safety of hydroxocobalamin in healthy volunteers in a randomized, placebo-controlled study. Clin Toxicol (Phila) 2006; 44 Suppl 1:17-28.

Broderick K E, Balasubramanian M, Chan A, et al. The cobalamin precursor cobinamide detoxifies nitroprusside-generated cyanide. Exp Biol Med (Maywood) 2007; 232:789-98.

Vick J, Marino M T, von Bredow J D, Kaminskis A, Brewer T. A reproducible nonlethal animal model for studying cyanide poisoning. Mil Med 2000; 165:967-72.

Hannon J P, Bossone C A, Wade C E. Normal physiological values for conscious pigs used in biomedical research. Lab Anim Sci 1990; 40:293-8.

Idris A H, Becker L B, Ornato J P, et al. Utstein-style guidelines for uniform reporting of laboratory CPR research. A statement for healthcare professionals from a task force of the American Heart Association, the American College of Emergency Physicians, the American College of Cardiology, the European Resuscitation Council, the Heart and Stroke Foundation of Canada, the Institute of Critical Care Medicine, the Safar Center for Resuscitation Research, and the Society for Academic Emergency Medicine. Writing Group. Circulation 1996; 94:2324-36.

Baker T A, Romero J, Bach H Ht, Strom J A, Gamelli R L, Majetschak M. Systemic release of cytokines and heat shock proteins in porcine models of polytrauma and hemorrhage*. Crit Care Med 2012; 40:876-85.

Niemann J T, Rosborough J, Youngquist S, Lewis R J, Phan Q T, Filler S. The proinflammatory cytokine response following resuscitation in the swine model depends on the method of ventricular fibrillation induction. Acad Emerg Med 2008; 15:939-44.

Almeida, A. F., P. N. Nation, et al. (2008). "Mechanism and treatment of sulfide-induced coma: a rat model." *International journal of toxicology* 27(3): 287-293.

Beck, J. F., C. M. Bradbury, et al. (1981). "Nitrite as antidote for acute hydrogen sulfide intoxication?" *American Industrial Hygiene Association journal* 42(11): 805-809.

Caro, A. A., S. Thompson, et al. (2011). "Increased oxidative stress and cytotoxicity by hydrogen sulfide in HepG2 cells overexpressing cytochrome P450 2E1." *Cell biology and toxicology* 27(6): 439-453.

Chalupka, A. N. and S. Chalupka (2008). "Acute occupational exposure to hydrogen sulfide." *AAOHN journal:* official journal of the American Association of Occupational Health Nurses 56(7): 324.

Chrzanowska-Lightowlers, Z. M., D. M. Turnbull, et al. (1993). "A microtiter plate assay for cytochrome c oxidase in permeabilized whole cells." *Analytical biochemistry* 214(1): 45-49.

Cooper, C. E. and G. C. Brown (2008). "The inhibition of mitochondrial cytochrome oxidase by the gases carbon monoxide, nitric oxide, hydrogen cyanide and hydrogen sulfide: chemical mechanism and physiological significance." *Journal of bioenergetics and biomembranes* 40(5): 533-539.

Dulaney, M., Jr. and A. S. Hume (1988). "Pyruvic acid protects against the lethality of sulfide." *Research communications in chemical pathology and pharmacology* 59(1): 133-136.

Ferguson, M., R. J. Mockett, et al. (2005). "Age-associated decline in mitochondrial respiration and electron transport in *Drosophila melanogaster*." *The Biochemical journal* 390(Pt 2): 501-511.

Fujino, Y., Y. Inoue, et al. (2010). "[Case followed by delayed loss of consciousness after exposure to hydrogen sulfide that was treated with intermittent administration of sodium nitrite]." *Chudoku kenkyu: Chudoku Kenkyukai jun kikanshi=The Japanese journal of toxicology* 23(4): 297-302.

Gee, S. J., C. E. Green, et al. (1990). "Cyanide-induced cytotoxicity to isolated hepatocytes." *Toxicology in vitro: an international journal published in association with BIBRA* 4(1): 37-45.

Gerasimon, G., S. Bennett, et al. (2007). "Acute hydrogen sulfide poisoning in a dairy farmer." *Clinical toxicology* 45(4): 420-423.

Gunn, B. and R. Wong (2001). "Noxious gas exposure in the outback: two cases of hydrogen sulfide toxicity." *Emergency medicine* 13(2): 240-246.

Hannas, B. R., P. C. Das, et al. (2010). "Intracellular conversion of environmental nitrate and nitrite to nitric oxide with resulting developmental toxicity to the crustacean *Daphnia magna*." *PloS one* 5(8): e12453.

Hayward, G. C., Hill H. A. O., Pratt, J. M., Vanston, N. J., and WIlliams, A. R. W. (1965). The chemistry of vitamin B12. Part VI. 1. The thermodynamic trans-effect. *J. Chem. Soc.*: 8.

Hildebrandt, T. M. (2011). "Modulation of sulfide oxidation and toxicity in rat mitochondria by dehydroascorbic acid." *Biochimica et biophysica acta* 1807(9): 1206-1213.

Huang, C. C. and N. S. Chu (1987). "A case of acute hydrogen sulfide (H2S) intoxication successfully treated with nitrites." *Taiwan yi xue hui za zhi. Journal of the Formosan Medical Association* 86(9): 1018-1020.

Jappinen, P. and R. Tenhunen (1990). "Hydrogen sulphide poisoning: blood sulphide concentration and changes in haem metabolism." *British journal of industrial medicine* 47(4): 283-285.

Kapoor, A. and C. Thiemermann (2010). "Hydrogen sulfide, neurogenic inflammation, and cardioprotection: a tale of rotten eggs and vanilloid receptors." *Critical care medicine* 38(2): 728-730.

Kimura, H. (2013). "Production and Physiological Effects of Hydrogen Sulfide." *Antioxidants & redox signaling*.

Kohn, M. C., R. L. Melnick, et al. (2002). "Pharmacokinetics of sodium nitrite-induced methemoglobinemia in the rat." *Drug metabolism and disposition: the biological fate of chemicals* 30(6): 676-683.

Kuroki, Y. (2008). "[Hydroxocobalamin]." *Chudoku kenkyu: Chudoku Kenkyukai jun kikanshi=The Japanese journal of toxicology* 21(4): 353-359.

Leavesley, H. B., L. Li, et al. (2010). "Nitrite-mediated antagonism of cyanide inhibition of cytochrome c oxidase in dopamine neurons." *Toxicological sciences: an official journal of the Society of Toxicology* 115(2): 569-576.

Leavesley, H. B., L. Li, et al. (2008). "Interaction of cyanide and nitric oxide with cytochrome c oxidase: implications for acute cyanide toxicity." *Toxicological sciences: an official journal of the Society of Toxicology* 101(1): 101-111.

Lee, Z. W., J. Zhou, et al. (2011). "The slow-releasing hydrogen sulfide donor, GYY4137, exhibits novel anti-cancer effects in vitro and in vivo." *PloS one* 6(6): e21077.

Linden, D. R. (2013). "Hydrogen Sulfide Signaling in the Gastrointestinal Tract." *Antioxidants & redox signaling*.

Liu, Y. H., M. Lu, et al. (2012). "Hydrogen sulfide in the mammalian cardiovascular system." *Antioxidants & redox signaling* 17(1): 141-185.

Mack, R. B. (1987). "World enough and time-hydrogen sulfide poisoning." *North Carolina medical journal* 48(1): 33-34.

Majstoravich, J., Jr. (1987). "Hydrogen sulfide poisoning." *North Carolina medical journal* 48(4): 225.

Mohanakrishnan, J., O. Gutierrez, et al. (2008). "Nitrite effectively inhibits sulfide and methane production in a laboratory scale sewer reactor." *Water research* 42(14): 3961-3971.

Nicholls, P. and J. K. Kim (1981). "Oxidation of sulphide by cytochrome aa3." *Biochimica et biophysica acta* 637(2): 312-320.

Nicholls, P. and J. K. Kim (1982). "Sulphide as an inhibitor and electron donor for the cytochrome c oxidase system." *Canadian journal of biochemistry* 60(6): 613-623.

Olson, K. R. (2011). "Hydrogen sulfide oxidation and the arterial chemoreflex: effect of methemoglobin" by Haouzi et al. [Respir. Physiol. Neurobiol. (2011)]." *Respiratory physiology & neurobiology* 179(2-3): 121; author reply 119-120.

P, R. (1971). "Some intermediates in the biosynthesis of vitamin B12." *Methods in Enzymology* 18(Part C): 10.

Partlo, L. A., R. S. Sainsbury, et al. (2001). "Effects of repeated hydrogen sulphide (H2S) exposure on learning and memory in the adult rat." *Neurotoxicology* 22(2): 177-189.

Peters, J. W. (1981). "Hydrogen sulfide poisoning in a hospital setting." *JAMA: the journal of the American Medical Association* 246(14): 1588-1589.

Picton, R., M. C. Eggo, et al. (2002). "Mucosal protection against sulphide: importance of the enzyme rhodanese." *Gut* 50(2): 201-205.

Predicala, B., M. Nemati, et al. (2008). "Control of $H_2S$ emission from swine manure using Na-nitrite and Na-molybdate." *Journal of hazardous materials* 154(1-3): 300-309.

Ravizza, A. G., D. Carugo, et al. (1982). "The treatment of hydrogen sulfide intoxication: oxygen versus nitrites." *Veterinary and human toxicology* 24(4): 241-242.

Reedy, S. J., M. D. Schwartz, et al. (2011). "Suicide fads: frequency and characteristics of hydrogen sulfide suicides in the United States." *The western journal of emergency medicine* 12(3): 300-304.

Reiffenstein, R. J., W. C. Hulbert, et al. (1992). "Toxicology of hydrogen sulfide." *Annual review of pharmacology and toxicology* 32: 109-134.

Ren, J. C., I. Rebrin, et al. (2010). "Cytochrome c oxidase loses catalytic activity and structural integrity during the aging process in *Drosophila melanogaster.*" *Biochemical and biophysical research communications* 401(1): 64-68.

Sarikaya, R. and S. Cakir (2005). "Genotoxicity testing of four food preservatives and their combinations in the Drosophila wing spot test." *Environmental toxicology and pharmacology* 20(3): 424-430.

Shaparenko, B. A., V. M. Foderman, et al. (1972). "[Use of antidote hydrogen sulfide prophylactic inhalations in persons exposed to metallic mercury vapor]." *Zhurnal ushnykh, nosovykh i gorlovykh boleznei=The journal of otology, rhinology, and laryngologie [sic]* 32(4): 1-3.

Silva, A. M. and P. J. Oliveira (2012). "Evaluation of respiration with clark type electrode in isolated mitochondria and permeabilized animal cells." *Methods in molecular biology* 810: 7-24.

Smilkstein, M. J., A. C. Bronstein, et al. (1985). "Hyperbaric oxygen therapy for severe hydrogen sulfide poisoning." *The Journal of emergency medicine* 3(1): 27-30.

Smith, R. P. (1969). "Cobalt salts: effects in cyanide and sulfide poisoning and on methemoglobinemia." *Toxicol Appl Pharmacol* 15(3): 505-516.

Smith, R. P. (1981). "Nitrite treatment for hydrogen sulfide poisoning." *Annals of internal medicine* 95(6): 782.

Smith, R. P. and R. A. Abbanat (1966). "Protective effect of oxidized glutathione in acute sulfide poisoning." *Toxicology and applied pharmacology* 9(2): 209-217.

Smith, R. P. and R. E. Gosselin (1964). "The Influence of Methemoglobinemia on the Lethality of Some Toxic Anions. Ii. Sulfide." *Toxicology and applied pharmacology* 6: 584-592.

Smith, R. P. and R. E. Gosselin (1966). "On the mechanism of sulfide inactivation by methemoglobin." *Toxicology and applied pharmacology* 8(1): 159-172.

Smith, R. P. and R. E. Gosselin (1979). "Hydrogen sulfide poisoning." *Journal of occupational medicine: official publication of the Industrial Medical Association* 21(2): 93-97.

Smith, R. P., R. Kruszyna, et al. (1976). "Management of acute sulfide poisoning. Effects of oxygen, thiosulfate, and nitrite." *Archives of environmental health* 31(3): 166-169.

Stine, R. J., B. Slosberg, et al. (1976). "Hydrogen sulfide intoxication. A case report and discussion of treatment." *Ann Intern Med* 85(6): 756-758.

Torrans, E. L. and H. P. Clemens (1982). "Physiological and biochemical effects of acute exposure of fish to hydrogen sulfide." *Comparative biochemistry and physiology. C: Comparative pharmacology* 71(2): 183-190.

Truong, D. H., M. A. Eghbal, et al. (2006). "Molecular mechanisms of hydrogen sulfide toxicity." *Drug metabolism reviews* 38(4): 733-744.

Truong, D. H., A. Mihajlovic, et al. (2007). "Prevention of hydrogen sulfide (H2S)-induced mouse lethality and cytotoxicity by hydroxocobalamin (vitamin B(12a))." *Toxicology* 242(1-3): 16-22.

Van de Louw, A. and P. Haouzi (2012). "Ferric Iron and Cobalt (III) Compounds to Safely Decrease Hydrogen Sulfide in the Body?" *Antioxidants & redox signaling.*

Warenycia, M. W., L. R. Goodwin, et al. (1990). "Dithiothreitol liberates non-acid labile sulfide from brain tissue of H2S-poisoned animals" *Archives of toxicology* 64(8): 650-655.

Westley, J. (1981). "Thiosulfate: cyanide sulfurtransferase (rhodanese)." *Methods in enzymology* 77: 285-291.

Whitcraft, D. D., 3rd, T. D. Bailey, et al. (1985). "Hydrogen sulfide poisoning treated with hyperbaric oxygen." *The Journal of emergency medicine* 3(1): 23-25.

Xu, Z. S., X. Y. Wang, et al. (2011). "Hydrogen sulfide protects MC3T3-E1 osteoblastic cells against H2O2-induced oxidative damage-implications for the treatment of osteoporosis." *Free radical biology & medicine* 50(10): 1314-1323.

Yang, G., X. Sun, et al. (2004). "Hydrogen sulfide-induced apoptosis of human aorta smooth muscle cells via the activation of mitogen-activated protein kinases and caspase-3." *The FASEB journal: official publication of the Federation of American Societies for Experimental Biology* 18(14): 1782-1784.

Zhong, J. F., S. P. Wang, et al. (2010). "Hydrogen sulfide exposure increases desiccation tolerance in *Drosophila melanogaster.*" *Journal of insect physiology* 56(12): 1777-1782.

The invention claimed is:

1. A compound having the formula:

[Chemical structure diagram of a cobinamide compound with cobalt center, corrin ring, and various substituents including $NH_2$, $NO_2$, $CH_3$, $CH_2$, and amide groups]

or pharmaceutically acceptable salts thereof.

2. A pharmaceutical composition comprising the compound of claim 1.

3. A composition comprising the compound of claim 1 and nitrite ion.

4. The composition of claim 3 wherein a molar ratio of the compound of claim 1 to the nitrite ion is between 1:1 and 1:2.

5. A method for treating sulfide poisoning or cyanide exposure in a subject comprising administering a therapeutically effective amount of a cobinamide to the subject, wherein the cobinamide is aquohydroxocobinamide, dinitrocobinamide or sulfitocobinamide.

6. The method of claim 5 wherein the subject is a human.

7. The method of claim 5 wherein the cobinamide is dinitrocobinamide.

8. The method of claim 5 wherein the cobinamide is administered intravenously.

9. The method of claim 5 wherein the cobinamide is administered intramuscularly.

10. The method of claim 5 wherein the cobinamide is administered at a dose of between 2 mg/kg and 25 mg/kg.

11. The method of claim 10 wherein the dose is between 2 mg/kg and 17 mg/kg.

12. The method of claim 10 wherein the dose is between 2 mg/kg and 15 mg/kg.

13. The method of claim 10 wherein the dose is between 15 mg/kg and 17 mg/kg.

14. A method of determining an extent of binding of an agent to extracellular matrix, the method comprising:
   providing a sample of mammalian extracellular matrix;
   contacting the sample with a solution comprising a known concentration of the agent;
   allowing binding to occur; and
   determining a second concentration of the agent remaining in the solution.

15. The method of claim 14 wherein the extracellular matrix is from muscle tissue.

16. The method of claim 14 wherein the extracellular matrix comprises decellularized skeletal muscle extracellular matrix.

17. The method of claim 14 wherein the agent is a cobinamide.

18. The method of claim 14 wherein determining a second concentration of the agent comprises a spectrophotometric method.

19. The method of claim 5, wherein the cobinamide is dinitrocobinamide, the dinitrocobinamide is administered intramuscularly, the dinitrocobinamide is administered as a pharmaceutical composition comprising the dinitrocobinamide and nitrite ions, and the molar ratio of the dinitrocobinamide to the nitrite ions is between 1:1 and 1:2.

\* \* \* \* \*

UNITED STATES PATENT AND TRADEMARK OFFICE
CERTIFICATE OF CORRECTION

PATENT NO. : 9,534,007 B2  
APPLICATION NO. : 14/654438  
DATED : January 3, 2017  
INVENTOR(S) : Gerry Boss et al.

Page 1 of 1

It is certified that error appears in the above-identified patent and that said Letters Patent is hereby corrected as shown below:

On the Title Page

Item (71) Applicants:
Delete "The United States of America as represented by The Secretary of the Air Force" and insert
--The Government of the United States of America as represented by The Secretary of the Air Force--

Item (73) Assignees:
Delete "THE UNITED STATES OF AMERICA as represented by THE SECRETARY OF THE AIR FORCE" and insert --THE GOVERNMENT OF THE UNITED STATES OF AMERICA as represented by THE SECRETARY OF THE AIR FORCE--

Signed and Sealed this
Twenty-first Day of March, 2017

Michelle K. Lee
*Director of the United States Patent and Trademark Office*